US008586826B2

(12) United States Patent
Mori et al.

(10) Patent No.: US 8,586,826 B2
(45) Date of Patent: Nov. 19, 2013

(54) VIRUS VECTOR AND USE THEREOF

(75) Inventors: Masashi Mori, Ishikawa (JP); Koji Dohi, Habikino (JP)

(73) Assignee: Japan Science and Technology Agency, Saitama (JP)

( * ) Notice: Subject to any disclaimer, the term of this patent is extended or adjusted under 35 U.S.C. 154(b) by 516 days.

(21) Appl. No.: 12/450,999

(22) PCT Filed: Apr. 11, 2008

(86) PCT No.: PCT/JP2008/057170
§ 371 (c)(1), (2), (4) Date: Dec. 14, 2010

(87) PCT Pub. No.: WO2008/136253
PCT Pub. Date: Nov. 13, 2008

(65) Prior Publication Data

US 2011/0107466 A1 May 5, 2011

(30) Foreign Application Priority Data

Apr. 27, 2007 (JP) ................................ 2007-120181

(51) Int. Cl.
*C07K 14/005* (2006.01)
*C12N 15/67* (2006.01)
*C12N 15/40* (2006.01)

(52) U.S. Cl.
USPC ............... 800/280; 435/5; 435/69.7; 435/6.1; 435/475; 435/320.1; 536/23.72

(58) Field of Classification Search
None
See application file for complete search history.

(56) References Cited

U.S. PATENT DOCUMENTS

2003/0036641 A1 * 2/2003 Padgett et al. ............... 536/23.1
2009/0017490 A1 1/2009 Mori et al.

FOREIGN PATENT DOCUMENTS

WO WO 0206501 A2 * 1/2002
WO WO 2005/049839 6/2005
WO WO 2006/003018 1/2006

OTHER PUBLICATIONS

Marillonnet et al. (Nature Biotechnology, vol. 23 No. 6 (2005) p. 718-723).*

T. Gillespie et al., "Functional Analysis of a DNA-Shuffled Movement Protein . . . ", The Plant Cell, 2002, vol. 14, No. 6, pp. 1207-1222.

R.L. Toth et al., "Improvement of the movement and host range . . . ", The Plant Journal, 2002, vol. 30, No. 5, pp. 593-600.

K. Dohi et al., "Inducible Virus-Mediated Expression . . . ", Archives of Virology, 2006, vol. 151, pp. 1075-1084.

S. Marillonnet et al., "In planta engineering of viral RNA replicons . . . ", PNAS, 2004, vol. 101, No. 18, pp. 6852-6857.

I.E. Johansen, "Intron insertion facilitates amplification of cloned . . . ", Proc. Natl. Acad. Sci., USA, 1996, vol. 93, pp. 12400-12405.

S.J. Yang et al., "Construction of full-length . . . ", Archives of Virology, 1998, vol. 143, pp. 2443-2451.

Search Report dated Sep. 23, 2010 for corresponding European Patent Application No. 08740267.3.

Koji Dohi, et al., "Insertion in the coding region of the movement protein improves stability of the plasmid encoding a tomato mosaic virus-based expression vector", Archives of Virology; Official Journal of the Virology Division of the International Union of Microbiological Societies, Springer-Verlag, VI, vol. 153, No. 9, Jul. 25, 2008, pp. 1667-1675, XP019634121 ISSN: 1432-8798, the whole document.

T. Satyanarayana, et al., "Frameshift mutations in infectious cDNA clones of *Citrus tristeza* virus: a strategy to minimize the toxicity of viral sequences to *Escherichia coli*", Virology, Academic Press, Orlando, US LNKD-DOI: 10.1016/S0042-6822 (03)00387-8, vol. 313, No. 2, Sep. 1, 2003, pp. 481-491, XP004452427 ISSN: 0042-6822, the whole document.

J. Yamaya, et al., "Expression of Tobacco Mosaic Virus RNA in Transgenic Plants" Molecular and General Genetics, Springer Verlag, Berlin, DE LNKD-DOI:10.1007/BF00425710, vol. 211, No. 3, Jan. 1, 1988, pp. 520-525, XP008024750 ISSN: 0026-8925, abstract.

* cited by examiner

*Primary Examiner* — David T Fox
*Assistant Examiner* — Jared Shapiro
(74) *Attorney, Agent, or Firm* — Harness, Dickey & Pierce, P.L.C.

(57) ABSTRACT

It is intended to provide a polynucleotide comprising a viral base sequence, the viral base sequence containing: a first base sequence encoding a viral replication protein, and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition. By using this, a vector containing a viral base sequence is constructed, and a protein is efficiently produced without worsening growth of a host cell containing the vector.

21 Claims, 5 Drawing Sheets

SEQUENCE LISTING

```
<160> NUMBER OF SEQ ID NOS: 39

<210> SEQ ID NO 1
<211> LENGTH: 1116
<212> TYPE: PRT
<213> ORGANISM: Tomato mosaic virus

<400> SEQUENCE: 1

Met Ala Tyr Thr Gln Thr Ala Thr Ser Ser Ala Leu Leu Glu Thr Val
1               5                   10                  15

Arg Gly Asn Asn Thr Leu Val Asn Asp Leu Ala Lys Arg Arg Leu Tyr
```

-continued

```
            20                  25                  30

Asp Thr Ala Val Asp Glu Phe Asn Ala Arg Asp Arg Arg Pro Lys Val
        35                  40                  45

Asn Phe Ser Lys Val Val Ser Glu Glu Gln Thr Leu Ile Ala Thr Lys
    50                  55                  60

Ala Tyr Pro Glu Phe Gln Ile Thr Phe Tyr Asn Thr Gln Asn Ala Val
65                  70                  75                  80

His Ser Leu Ala Gly Gly Leu Arg Ser Leu Glu Leu Glu Tyr Leu Met
                85                  90                  95

Met Gln Ile Pro Tyr Gly Ser Leu Thr Tyr Asp Ile Gly Gly Asn Phe
            100                 105                 110

Ala Ser His Leu Phe Lys Gly Arg Ala Tyr Val His Cys Cys Met Pro
        115                 120                 125

Asn Leu Asp Val Arg Asp Ile Met Arg His Glu Gly Gln Lys Asp Ser
    130                 135                 140

Ile Glu Leu Tyr Leu Ser Arg Leu Glu Arg Gly Asn Lys His Val Pro
145                 150                 155                 160

Asn Phe Gln Lys Glu Ala Phe Asp Arg Tyr Ala Glu Met Pro Asn Glu
                165                 170                 175

Val Val Cys His Asp Thr Phe Gln Thr Cys Arg His Ser Gln Glu Cys
            180                 185                 190

Tyr Thr Gly Arg Val Tyr Ala Ile Ala Leu His Ser Ile Tyr Asp Ile
        195                 200                 205

Pro Ala Asp Glu Phe Gly Ala Ala Leu Leu Arg Lys Asn Val His Val
    210                 215                 220

Cys Tyr Ala Ala Phe His Phe Ser Glu Asn Leu Leu Leu Glu Asp Ser
225                 230                 235                 240

His Val Asn Leu Asp Glu Ile Asn Ala Cys Phe Gln Arg Asp Gly Asp
                245                 250                 255

Arg Leu Thr Phe Ser Phe Ala Ser Glu Ser Thr Leu Asn Tyr Ser His
            260                 265                 270

Ser Tyr Ser Asn Ile Leu Lys Tyr Val Cys Lys Thr Tyr Phe Pro Ala
        275                 280                 285

Ser Asn Arg Glu Val Tyr Met Lys Glu Phe Leu Val Thr Arg Val Asn
    290                 295                 300

Thr Trp Phe Cys Lys Phe Ser Arg Ile Asp Thr Phe Leu Leu Tyr Lys
305                 310                 315                 320

Gly Val Ala His Lys Gly Val Asp Ser Glu Gln Phe Tyr Lys Ala Met
                325                 330                 335

Glu Asp Ala Trp His Tyr Lys Lys Thr Leu Ala Met Cys Asn Ser Glu
            340                 345                 350

Arg Ile Leu Leu Glu Asp Ser Ser Ser Val Asn Tyr Trp Phe Pro Lys
        355                 360                 365

Met Arg Asp Met Val Ile Val Pro Leu Phe Asp Ile Ser Leu Glu Thr
    370                 375                 380

Ser Lys Arg Thr Arg Lys Glu Val Leu Val Ser Lys Asp Phe Val Tyr
385                 390                 395                 400

Thr Val Leu Asn His Ile Arg Thr Tyr Gln Ala Lys Ala Leu Thr Tyr
                405                 410                 415

Ser Asn Val Leu Ser Phe Val Glu Ser Ile Arg Ser Arg Val Ile Ile
            420                 425                 430

Asn Gly Val Thr Ala Arg Ser Glu Trp Asp Val Asp Lys Ser Leu Leu
        435                 440                 445
```

-continued

```
Gln Ser Leu Ser Met Thr Phe Phe Leu His Thr Lys Leu Ala Val Leu
    450                 455                 460

Lys Asp Asp Leu Leu Ile Ser Lys Phe Ala Leu Gly Pro Lys Thr Val
465                 470                 475                 480

Ser Gln His Val Trp Asp Glu Ile Ser Leu Ala Phe Gly Asn Ala Phe
                485                 490                 495

Pro Ser Ile Lys Glu Arg Leu Ile Asn Arg Lys Leu Ile Lys Ile Thr
            500                 505                 510

Glu Asn Ala Leu Glu Ile Arg Val Pro Asp Leu Tyr Val Thr Phe His
        515                 520                 525

Asp Arg Leu Val Ser Glu Tyr Lys Met Ser Val Asp Met Pro Val Leu
    530                 535                 540

Asp Ile Arg Lys Lys Met Glu Glu Thr Glu Glu Met Tyr Asn Ala Leu
545                 550                 555                 560

Ser Glu Leu Ser Val Leu Lys Asn Ser Asp Lys Phe Asp Val Asp Val
                565                 570                 575

Phe Ser Gln Met Cys Gln Ser Leu Glu Val Asp Pro Met Thr Ala Ala
            580                 585                 590

Lys Val Ile Val Ala Val Met Ser Asn Glu Ser Gly Leu Thr Leu Thr
        595                 600                 605

Phe Glu Gln Pro Thr Glu Ala Asn Val Ala Leu Ala Leu Gln Asp Ser
    610                 615                 620

Glu Lys Ala Ser Asp Gly Ala Leu Val Val Thr Ser Arg Asp Val Glu
625                 630                 635                 640

Glu Pro Ser Ile Lys Gly Ser Met Ala Arg Gly Glu Leu Gln Leu Ala
                645                 650                 655

Gly Leu Ser Gly Asp Val Pro Glu Ser Ser Tyr Thr Arg Ser Glu Glu
            660                 665                 670

Ile Glu Ser Leu Glu Gln Phe His Met Ala Thr Ala Ser Ser Leu Ile
        675                 680                 685

His Lys Gln Met Cys Ser Ile Val Tyr Thr Gly Pro Leu Lys Val Gln
    690                 695                 700

Gln Met Lys Asn Phe Ile Asp Ser Leu Val Ala Ser Leu Ser Ala Ala
705                 710                 715                 720

Val Ser Asn Leu Val Lys Ile Leu Lys Asp Thr Ala Ala Ile Asp Leu
                725                 730                 735

Glu Thr Arg Gln Lys Phe Gly Val Leu Asp Val Ala Ser Lys Arg Trp
            740                 745                 750

Leu Val Lys Pro Ser Ala Lys Asn His Ala Trp Gly Val Val Glu Thr
        755                 760                 765

His Ala Arg Lys Tyr His Val Ala Leu Leu Glu His Asp Glu Phe Gly
    770                 775                 780

Ile Ile Thr Cys Asp Asn Trp Arg Arg Val Ala Val Ser Ser Glu Ser
785                 790                 795                 800

Val Val Tyr Ser Asp Met Ala Lys Leu Arg Thr Leu Arg Arg Leu Leu
                805                 810                 815

Lys Asp Gly Glu Pro His Val Ser Ser Ala Lys Val Val Leu Val Asp
            820                 825                 830

Gly Val Pro Gly Cys Gly Lys Thr Lys Glu Ile Leu Ser Arg Val Asn
        835                 840                 845

Phe Glu Glu Asp Leu Ile Leu Val Pro Gly Arg Gln Ala Ala Glu Met
    850                 855                 860

Ile Arg Arg Arg Ala Asn Ala Ser Gly Ile Ile Val Ala Thr Lys Asp
865                 870                 875                 880
```

```
Asn Val Arg Thr Val Asp Ser Phe Leu Met Asn Tyr Gly Lys Gly Ala
                885                 890                 895

Arg Cys Gln Phe Lys Arg Leu Phe Ile Asp Glu Gly Leu Met Leu His
            900                 905                 910

Thr Gly Cys Val Asn Phe Leu Val Glu Met Ser Leu Cys Asp Ile Ala
        915                 920                 925

Tyr Val Tyr Gly Asp Thr Gln Gln Ile Pro Tyr Ile Asn Arg Val Thr
    930                 935                 940

Gly Phe Pro Tyr Pro Ala His Phe Ala Lys Leu Glu Val Asp Glu Val
945                 950                 955                 960

Glu Thr Arg Arg Thr Thr Leu Arg Cys Pro Ala Asp Val Thr His Phe
                965                 970                 975

Leu Asn Gln Arg Tyr Glu Gly His Val Met Cys Thr Ser Ser Glu Lys
            980                 985                 990

Lys Ser Val Ser Gln Glu Met Val  Ser Gly Ala Ala Ser  Ile Asn Pro
        995                 1000                1005

Val Ser  Lys Pro Leu Lys Gly  Lys Ile Leu Thr Phe  Thr Gln Ser
    1010                1015                1020

Asp Lys  Glu Ala Leu Leu Ser  Arg Gly Tyr Ala Asp  Val His Thr
    1025                1030                1035

Val His  Glu Val Gln Gly Glu  Thr Tyr Ala Asp Val  Ser Leu Val
    1040                1045                1050

Arg Leu  Thr Pro Thr Pro Val  Ser Ile Ile Ala Arg  Asp Ser Pro
    1055                1060                1065

His Val  Leu Val Ser Leu Ser  Arg His Thr Lys Ser  Leu Lys Tyr
    1070                1075                1080

Tyr Thr  Val Val Met Asp Pro  Leu Val Ser Ile Ile  Arg Asp Leu
    1085                1090                1095

Glu Arg  Val Ser Ser Tyr Leu  Leu Asp Met Tyr Lys  Val Asp Ala
    1100                1105                1110

Gly Thr  Gln
    1115


<210> SEQ ID NO 2
<211> LENGTH: 1616
<212> TYPE: PRT
<213> ORGANISM: Tomato mosaic virus

<400> SEQUENCE: 2

Met Ala Tyr Thr Gln Thr Ala Thr Ser Ser Ala Leu Leu Glu Thr Val
1               5                   10                  15

Arg Gly Asn Asn Thr Leu Val Asn Asp Leu Ala Lys Arg Arg Leu Tyr
            20                  25                  30

Asp Thr Ala Val Asp Glu Phe Asn Ala Arg Asp Arg Arg Pro Lys Val
        35                  40                  45

Asn Phe Ser Lys Val Val Ser Glu Glu Gln Thr Leu Ile Ala Thr Lys
    50                  55                  60

Ala Tyr Pro Glu Phe Gln Ile Thr Phe Tyr Asn Thr Gln Asn Ala Val
65                  70                  75                  80

His Ser Leu Ala Gly Gly Leu Arg Ser Leu Glu Leu Glu Tyr Leu Met
                85                  90                  95

Met Gln Ile Pro Tyr Gly Ser Leu Thr Tyr Asp Ile Gly Gly Asn Phe
            100                 105                 110

Ala Ser His Leu Phe Lys Gly Arg Ala Tyr Val His Cys Cys Met Pro
        115                 120                 125
```

-continued

```
Asn Leu Asp Val Arg Asp Ile Met Arg His Glu Gly Gln Lys Asp Ser
    130                 135                 140

Ile Glu Leu Tyr Leu Ser Arg Leu Glu Arg Gly Asn Lys His Val Pro
145                 150                 155                 160

Asn Phe Gln Lys Glu Ala Phe Asp Arg Tyr Ala Glu Met Pro Asn Glu
                165                 170                 175

Val Val Cys His Asp Thr Phe Gln Thr Cys Arg His Ser Gln Glu Cys
            180                 185                 190

Tyr Thr Gly Arg Val Tyr Ala Ile Ala Leu His Ser Ile Tyr Asp Ile
        195                 200                 205

Pro Ala Asp Glu Phe Gly Ala Ala Leu Leu Arg Lys Asn Val His Val
    210                 215                 220

Cys Tyr Ala Ala Phe His Phe Ser Glu Asn Leu Leu Leu Glu Asp Ser
225                 230                 235                 240

His Val Asn Leu Asp Glu Ile Asn Ala Cys Phe Gln Arg Asp Gly Asp
                245                 250                 255

Arg Leu Thr Phe Ser Phe Ala Ser Glu Ser Thr Leu Asn Tyr Ser His
            260                 265                 270

Ser Tyr Ser Asn Ile Leu Lys Tyr Val Cys Lys Thr Tyr Phe Pro Ala
        275                 280                 285

Ser Asn Arg Glu Val Tyr Met Lys Glu Phe Leu Val Thr Arg Val Asn
    290                 295                 300

Thr Trp Phe Cys Lys Phe Ser Arg Ile Asp Thr Phe Leu Leu Tyr Lys
305                 310                 315                 320

Gly Val Ala His Lys Gly Val Asp Ser Glu Gln Phe Tyr Lys Ala Met
                325                 330                 335

Glu Asp Ala Trp His Tyr Lys Lys Thr Leu Ala Met Cys Asn Ser Glu
            340                 345                 350

Arg Ile Leu Leu Glu Asp Ser Ser Ser Val Asn Tyr Trp Phe Pro Lys
        355                 360                 365

Met Arg Asp Met Val Ile Val Pro Leu Phe Asp Ile Ser Leu Glu Thr
    370                 375                 380

Ser Lys Arg Thr Arg Lys Glu Val Leu Val Ser Lys Asp Phe Val Tyr
385                 390                 395                 400

Thr Val Leu Asn His Ile Arg Thr Tyr Gln Ala Lys Ala Leu Thr Tyr
                405                 410                 415

Ser Asn Val Leu Ser Phe Val Glu Ser Ile Arg Ser Arg Val Ile Ile
            420                 425                 430

Asn Gly Val Thr Ala Arg Ser Glu Trp Asp Val Asp Lys Ser Leu Leu
        435                 440                 445

Gln Ser Leu Ser Met Thr Phe Phe Leu His Thr Lys Leu Ala Val Leu
    450                 455                 460

Lys Asp Asp Leu Leu Ile Ser Lys Phe Ala Leu Gly Pro Lys Thr Val
465                 470                 475                 480

Ser Gln His Val Trp Asp Glu Ile Ser Leu Ala Phe Gly Asn Ala Phe
                485                 490                 495

Pro Ser Ile Lys Glu Arg Leu Ile Asn Arg Lys Leu Ile Lys Ile Thr
            500                 505                 510

Glu Asn Ala Leu Glu Ile Arg Val Pro Asp Leu Tyr Val Thr Phe His
        515                 520                 525

Asp Arg Leu Val Ser Glu Tyr Lys Met Ser Val Asp Met Pro Val Leu
    530                 535                 540

Asp Ile Arg Lys Lys Met Glu Glu Thr Glu Glu Met Tyr Asn Ala Leu
```

-continued

```
545                 550                 555                 560

Ser Glu Leu Ser Val Leu Lys Asn Ser Asp Lys Phe Asp Val Asp Val
                565                 570                 575

Phe Ser Gln Met Cys Gln Ser Leu Glu Val Asp Pro Met Thr Ala Ala
            580                 585                 590

Lys Val Ile Val Ala Val Met Ser Asn Glu Ser Gly Leu Thr Leu Thr
        595                 600                 605

Phe Glu Gln Pro Thr Glu Ala Asn Val Ala Leu Ala Leu Gln Asp Ser
    610                 615                 620

Glu Lys Ala Ser Asp Gly Ala Leu Val Val Thr Ser Arg Asp Val Glu
625                 630                 635                 640

Glu Pro Ser Ile Lys Gly Ser Met Ala Arg Gly Glu Leu Gln Leu Ala
                645                 650                 655

Gly Leu Ser Gly Asp Val Pro Glu Ser Ser Tyr Thr Arg Ser Glu Glu
            660                 665                 670

Ile Glu Ser Leu Glu Gln Phe His Met Ala Thr Ala Ser Ser Leu Ile
        675                 680                 685

His Lys Gln Met Cys Ser Ile Val Tyr Thr Gly Pro Leu Lys Val Gln
    690                 695                 700

Gln Met Lys Asn Phe Ile Asp Ser Leu Val Ala Ser Leu Ser Ala Ala
705                 710                 715                 720

Val Ser Asn Leu Val Lys Ile Leu Lys Asp Thr Ala Ala Ile Asp Leu
                725                 730                 735

Glu Thr Arg Gln Lys Phe Gly Val Leu Asp Val Ala Ser Lys Arg Trp
            740                 745                 750

Leu Val Lys Pro Ser Ala Lys Asn His Ala Trp Gly Val Val Glu Thr
        755                 760                 765

His Ala Arg Lys Tyr His Val Ala Leu Leu Glu His Asp Glu Phe Gly
    770                 775                 780

Ile Ile Thr Cys Asp Asn Trp Arg Arg Val Ala Val Ser Ser Glu Ser
785                 790                 795                 800

Val Val Tyr Ser Asp Met Ala Lys Leu Arg Thr Leu Arg Arg Leu Leu
                805                 810                 815

Lys Asp Gly Glu Pro His Val Ser Ser Ala Lys Val Val Leu Val Asp
            820                 825                 830

Gly Val Pro Gly Cys Gly Lys Thr Lys Glu Ile Leu Ser Arg Val Asn
        835                 840                 845

Phe Glu Glu Asp Leu Ile Leu Val Pro Gly Arg Gln Ala Ala Glu Met
    850                 855                 860

Ile Arg Arg Arg Ala Asn Ala Ser Gly Ile Ile Val Ala Thr Lys Asp
865                 870                 875                 880

Asn Val Arg Thr Val Asp Ser Phe Leu Met Asn Tyr Gly Lys Gly Ala
                885                 890                 895

Arg Cys Gln Phe Lys Arg Leu Phe Ile Asp Glu Gly Leu Met Leu His
            900                 905                 910

Thr Gly Cys Val Asn Phe Leu Val Glu Met Ser Leu Cys Asp Ile Ala
        915                 920                 925

Tyr Val Tyr Gly Asp Thr Gln Gln Ile Pro Tyr Ile Asn Arg Val Thr
    930                 935                 940

Gly Phe Pro Tyr Pro Ala His Phe Ala Lys Leu Glu Val Asp Glu Val
945                 950                 955                 960

Glu Thr Arg Arg Thr Thr Leu Arg Cys Pro Ala Asp Val Thr His Phe
                965                 970                 975
```

-continued

```
Leu Asn Gln Arg Tyr Glu Gly His Val Met Cys Thr Ser Ser Glu Lys
            980                 985                 990

Lys Ser Val Ser Gln Glu Met Val  Ser Gly Ala Ala Ser  Ile Asn Pro
        995                 1000                 1005

Val Ser  Lys Pro Leu Lys Gly  Lys Ile Leu Thr Phe  Thr Gln Ser
    1010                 1015                 1020

Asp Lys  Glu Ala Leu Leu Ser  Arg Gly Tyr Ala Asp  Val His Thr
    1025                 1030                 1035

Val His  Glu Val Gln Gly Glu  Thr Tyr Ala Asp Val  Ser Leu Val
    1040                 1045                 1050

Arg Leu  Thr Pro Thr Pro Val  Ser Ile Ile Ala Arg  Asp Ser Pro
    1055                 1060                 1065

His Val  Leu Val Ser Leu Ser  Arg His Thr Lys Ser  Leu Lys Tyr
    1070                 1075                 1080

Tyr Thr  Val Val Met Asp Pro  Leu Val Ser Ile Ile  Arg Asp Leu
    1085                 1090                 1095

Glu Arg  Val Ser Ser Tyr Leu  Leu Asp Met Tyr Lys  Val Asp Ala
    1100                 1105                 1110

Gly Thr  Gln Tyr Gln Leu Gln  Val Asp Ser Val Phe  Lys Asn Phe
    1115                 1120                 1125

Asn Leu  Phe Val Ala Ala Pro  Lys Thr Gly Asp Ile  Ser Asp Met
    1130                 1135                 1140

Gln Phe  Tyr Tyr Asp Lys Cys  Leu Pro Gly Asn Ser  Thr Leu Leu
    1145                 1150                 1155

Asn Asn  Tyr Asp Ala Val Thr  Met Lys Leu Thr Asp  Ile Ser Leu
    1160                 1165                 1170

Asn Val  Lys Asp Cys Ile Leu  Asp Met Ser Lys Ser  Val Ala Ala
    1175                 1180                 1185

Pro Lys  Asp Val Lys Pro Thr  Leu Ile Pro Met Val  Arg Thr Ala
    1190                 1195                 1200

Ala Glu  Met Pro Arg Gln Thr  Gly Leu Leu Glu Asn  Leu Val Ala
    1205                 1210                 1215

Met Ile  Lys Arg Asn Phe Asn  Ser Pro Glu Leu Ser  Gly Val Val
    1220                 1225                 1230

Asp Ile  Glu Asn Thr Ala Ser  Leu Val Val Asp Lys  Phe Phe Asp
    1235                 1240                 1245

Ser Tyr  Leu Leu Lys Glu Lys  Arg Lys Pro Asn Lys  Asn Phe Ser
    1250                 1255                 1260

Leu Phe  Ser Arg Glu Ser Leu  Asn Arg Trp Ile Ala  Lys Gln Glu
    1265                 1270                 1275

Gln Val  Thr Ile Gly Gln Leu  Ala Asp Phe Asp Phe  Val Asp Leu
    1280                 1285                 1290

Pro Ala  Val Asp Gln Tyr Arg  His Met Ile Lys Ala  Gln Pro Lys
    1295                 1300                 1305

Gln Lys  Leu Asp Leu Ser Ile  Gln Thr Glu Tyr Pro  Ala Leu Gln
    1310                 1315                 1320

Thr Ile  Val Tyr His Ser Lys  Lys Ile Asn Ala Ile  Phe Gly Pro
    1325                 1330                 1335

Leu Phe  Ser Glu Leu Thr Arg  Gln Leu Leu Asp Ser  Ile Asp Ser
    1340                 1345                 1350

Ser Arg  Phe Leu Phe Phe Thr  Arg Lys Thr Pro Ala  Gln Ile Glu
    1355                 1360                 1365

Asp Phe  Phe Gly Asp Leu Asp  Ser His Val Pro Met  Asp Val Leu
    1370                 1375                 1380
```

```
Glu Leu  Asp Val Ser Lys Tyr  Asp Lys Ser Gln Asn  Glu Phe His
    1385                 1390                 1395

Cys Ala  Val Glu Tyr Glu Ile  Trp Arg Arg Leu Gly  Leu Glu Asp
    1400                 1405                 1410

Phe Leu  Ala Glu Val Trp Lys  Gln Gly His Arg Lys  Thr Thr Leu
    1415                 1420                 1425

Lys Asp  Tyr Thr Ala Gly Ile  Lys Thr Cys Leu Trp  Tyr Gln Arg
    1430                 1435                 1440

Lys Ser  Gly Asp Val Thr Thr  Phe Ile Gly Asn Thr  Val Ile Ile
    1445                 1450                 1455

Ala Ser  Cys Leu Ala Ser Met  Leu Pro Met Glu Lys  Leu Ile Lys
    1460                 1465                 1470

Gly Ala  Phe Cys Gly Asp Asp  Ser Leu Leu Tyr Phe  Pro Lys Gly
    1475                 1480                 1485

Cys Glu  Tyr Pro Asp Ile Gln  Gln Ala Ala Asn Leu  Met Trp Asn
    1490                 1495                 1500

Phe Glu  Ala Lys Leu Phe Lys  Lys Gln Tyr Gly Tyr  Phe Cys Gly
    1505                 1510                 1515

Arg Tyr  Val Ile His His Asp  Arg Gly Cys Ile Val  Tyr Tyr Asp
    1520                 1525                 1530

Pro Leu  Lys Leu Ile Ser Lys  Leu Gly Ala Lys His  Ile Lys Asp
    1535                 1540                 1545

Trp Asp  His Leu Glu Glu Phe  Arg Arg Ser Leu Cys  Asp Val Ala
    1550                 1555                 1560

Glu Ser  Leu Asn Asn Cys Ala  Tyr Tyr Thr Gln Leu  Asp Asp Ala
    1565                 1570                 1575

Val Gly  Glu Val His Lys Thr  Ala Pro Pro Gly Ser  Phe Val Tyr
    1580                 1585                 1590

Lys Ser  Leu Val Lys Tyr Leu  Ser Asp Lys Val Leu  Phe Arg Ser
    1595                 1600                 1605

Leu Phe  Leu Asp Gly Ser Ser  Cys
    1610                 1615


<210> SEQ ID NO 3
<211> LENGTH: 264
<212> TYPE: PRT
<213> ORGANISM: Tomato mosaic virus

<400> SEQUENCE: 3

Met Ala Leu Val Val Lys Gly Lys Val Asn Ile Asn Glu Phe Ile Asp
1               5                   10                  15

Leu Ser Lys Ser Glu Lys Leu Leu Pro Ser Met Phe Thr Pro Val Lys
            20                  25                  30

Ser Val Met Val Ser Lys Val Asp Lys Ile Met Val His Glu Asn Glu
        35                  40                  45

Ser Leu Ser Glu Val Asn Leu Leu Lys Gly Val Lys Leu Ile Glu Gly
    50                  55                  60

Gly Tyr Val Cys Leu Val Gly Leu Val Val Ser Gly Glu Trp Asn Leu
65                  70                  75                  80

Pro Asp Asn Cys Arg Gly Gly Val Ser Val Cys Met Val Asp Lys Arg
                85                  90                  95

Met Glu Arg Ala Asp Glu Ala Thr Leu Gly Ser Tyr Tyr Thr Ala Ala
            100                 105                 110

Ala Lys Lys Arg Phe Gln Phe Lys Val Val Pro Asn Tyr Gly Ile Thr
        115                 120                 125
```

-continued

```
Thr Lys Asp Ala Glu Lys Asn Ile Trp Gln Val Leu Val Asn Ile Lys
    130                 135                 140

Asn Val Lys Met Ser Ala Gly Tyr Cys Pro Leu Ser Leu Glu Phe Val
145                 150                 155                 160

Ser Val Cys Ile Val Tyr Lys Asn Asn Ile Lys Leu Gly Leu Arg Glu
                165                 170                 175

Lys Val Thr Ser Val Asn Asp Gly Gly Pro Met Glu Leu Ser Glu Glu
            180                 185                 190

Val Val Asp Glu Phe Met Glu Asn Val Pro Met Ser Val Arg Leu Ala
        195                 200                 205

Lys Phe Arg Thr Lys Ser Ser Lys Arg Gly Pro Lys Asn Asn Asn Asn
   210                 215                 220

Leu Gly Lys Gly Arg Ser Gly Gly Arg Pro Lys Pro Lys Ser Phe Asp
225                 230                 235                 240

Glu Val Glu Lys Glu Phe Asp Asn Leu Ile Glu Asp Glu Ala Glu Thr
                245                 250                 255

Ser Val Ala Asp Ser Asp Ser Tyr
            260


<210> SEQ ID NO 4
<211> LENGTH: 2131
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4

atggctctag ttgttaaagg taaggtaaat attaatgagt ttatcgatct gtcaaagtct      60

gagaaacttc tcccgtcgat gttcacgcct gtaaagagtg ttatggtttc aaaggttgat     120

aagattatgg tccatgaaaa tgaatcattg tctgaagtaa atctcttaaa aggtgtaaaa     180

cttatagaag gtgggtatgt ttgcttagtc ggtcttgttg tgtccggtga gtggaattta     240

ccagataatt gccgtggtgg tgtgagtgga tttgccccta tatttccaga catctgttat     300

cacttaaccc attacaagcc cgctgccgca gatattcccg tggcgagcga taacccagcg     360

cactatgcgg atgccattcg ttataatgct cgaacgcctc tgcaaggttc tttgctgccg     420

ttaacccgtc tggtttgggc atgatactga tgtagtcacg ctttatcgtt ttcacgaagc     480

tctctgctat tccgttactc tccggactcc gcaccgccgt gttcttcggt tcaagtccca     540

acatccgggc gaactggcgt gtttcattag cccggtagca tgaaccatta tccgtcagcc     600

actccactgg agacgacgga agatcgttgc cgaagcggcg ttccaccgct cccagcatga     660

cgtcctgtac tgtttcactg ttgaagccgc cggtagtgac cgcccagtgc agtgcctcac     720

gatcacagca gtccagcgcg aacgtgacac gcagtctctc tccgttatca cagcagaact     780

cgaacccgtc agagcaccat cgctgattgc tttctttcac ggccactctg cctgtatgtg     840

cccgtttcga tggcggtaca gcaggttttc gctcaagcaa cagcgcattc tggcgcatga     900

tccggtaaac acgtttggca ttgatcgcag gcataccatc aagttctgcc tgtctgcgaa     960

gcagcgccca tacccgacga taaccatacg ttggcagctc tccgataaca tggtgtatac    1020

ggagaagcac atccgtatca tcagtgtgac gactgcggcg gccatccatc cagtcatcgg    1080

ttcgtctgag aatgacgtgc aactgcgcac gcgacacccg gagacaacgg ctgactaagc    1140

ttactcccca tccccgggca ataagggcgc gtgcgctatc cacttttttg cccgtccata    1200

ttcaacggct tctttgagga gttcattttc catcgttttc ttgccgagca ggcgctggag    1260
```

ttctttaatc tgcttcatgg cggcagcaag ttcagaggca ggaacaacct gttctccggc 1320
ggcgacagca gtaagacttc cttcctggta ttgcttacgc cagagaaata actggctggc 1380
tgctacacca tgttgccggg caacgaggga gaccgtcatc cccggttcaa agctctgctg 1440
aacaattgcg atcttttcct gtgtggtacg ccgtctgcgt ttctccggcc ctaagacatc 1500
aatcatctgt tctccaatga ctagtctaaa aactagtatt aagactatca cttatttaag 1560
tgatattggt tgtctggaga ttcagggggc cagtctagtg agtgtctgca tggttgacaa 1620
gagaatggaa agagcggacg aagccacact ggggtcatat tacactgctg ctgctaaaaa 1680
gcggtttcag tttaaagtgg tcccaaatta cggtattaca acaaaggatg cagaaaagaa 1740
catatggcag gtcttagtaa atattaaaaa tgtaaaaatg agtgcgggct actgcccttt 1800
gtcattagaa tttgtgtctg tgtgtattgt ttataaaaat aatataaaat tgggtttgag 1860
ggagaaagta acgagtgtga acgatggagg acccatggaa ctttcggaag aagttgttga 1920
tgagttcatg gagaatgttc caatgtcggt tagactcgca aagtttcgaa ccaaatcctc 1980
aaaaagaggt ccgaaaaata ataataattt aggtaagggg cgttcaggcg gaaggcctaa 2040
accaaaaagt tttgatgaag ttgaaaaaga gtttgataat ttgattgaag atgaagccga 2100
gacgtcggtc gcggattctg attcgtatta a 2131

<210> SEQ ID NO 5
<211> LENGTH: 2053
<212> TYPE: DNA
<213> ORGANISM: Artificial Sequence
<220> FEATURE:
<223> OTHER INFORMATION: Description of Artificial Sequence: Synthetic DNA

<400> SEQUENCE: 5
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg tgtgagtgga tttgccccta tatttccaga catctgttat 300
cacttaaccc attacaagcc cgctgccgca gatattcccg tggcgagcga taacccagcg 360
cactatgcgg atgccattcg ttataatgct cgaacgcctc tgcaaggttc tttgctgccg 420
ttaacccgtc tggtttgggc atgatactga tgtagtcacg ctttatcgtt ttcacgaagc 480
tctctgctat tccgttactc tccggactcc gcaccgccgt gttcttcggt tcaagtccca 540
acatccgggc gaactggcgt gtttcattag cccggtagca tgaaccatta tccgtcagcc 600
actccactgg agacgacgga agatcgttgc cgaagcggcg ttccaccgct cccagcatga 660
cgtcctgtac tgtttcactg ttgaagccgc cggtagtgac cgcccagtgc agtgcctcac 720
gatcacagca gtccagcgcg aacgtgacac gcagtctctc tccgttatca cagcagaact 780
cgaacccgtc agagcaccat cgctgattgc tttctttcac ggccactctg cctgtatgtg 840
cccgtttcga tggcggtaca gcaggttttc gctcaagcaa cagcgcattc tggcgcatga 900
tccggtaaac acgtttggca ttgatcgcag gcataccatc aagttctgcc tgtctgcgaa 960
gcagcgccca tacccgacga taaccatacg ttggcagctc tccgataaca tggtgtatac 1020
ggagaagcac atccgtatca tcagtgtgac gactgcggcg gccatccatc cagtcatcgg 1080
ttcgtctgag aatgacgtgc aactgcgcac gcgacacccg gagacaacgg ctgactaagc 1140

-continued ttactcccca tccccgggca ataagggcgc gtgcgctatc cactttttttg cccgtccata 1200 ttcaacggct tctttgagga gttcattttc catcgttttc ttgccgagca ggcgctggag 1260
ttctttaatc tgcttcatgg cggcagcaag ttcagaggca ggaacaacct gttctccggc 1320
ggcgacagca gtaagacttc cttcctggta ttgcttacgc cagagaaata actggctggc 1380
tgctacacca tgttgccggg caacgaggga gaccgtcatc cccggttcaa agctctgctg 1440
aacaattgcg atcttttcct gtgtggtacg ccgtctgcgt ttctccggcc ctaagacatc 1500
aatcatctgt tctccaatgg tgagtgtctg catggttgac aagagaatgg aaagagcgga 1560
cgaagccaca ctggggtcat attacactgc tgctgctaaa aagcggtttc agtttaaagt 1620
ggtcccaaat tacggtatta caacaaagga tgcagaaaag aacatatggc aggtcttagt 1680
aaatattaaa aatgtaaaaa tgagtgcggg ctactgccct ttgtcattag aatttgtgtc 1740
tgtgtgtatt gtttataaaa ataatataaa attgggtttg agggagaaag taacgagtgt 1800
gaacgatgga ggacccatgg aactttcgga agaagttgtt gatgagttca tggagaatgt 1860
tccaatgtcg gttagactcg caaagtttcg aaccaaatcc tcaaaaagag gtccgaaaaa 1920
taataataat ttaggtaagg ggcgttcagg cggaaggcct aaaccaaaaa gttttgatga 1980
agttgaaaaa gagtttgata atttgattga agatgaagcc gagacgtcgg tcgcggattc 2040
tgattcgtat taa 2053

<210> SEQ ID NO 6
<211> LENGTH: 2128
<212> TYPE: DNA
<213> ORGANISM: Artificial Sequence
<220> FEATURE:
<223> OTHER INFORMATION: Description of Artificial Sequence: Synthetic DNA

<400> SEQUENCE: 6
atggctctag ttgttaataa cggttcaggc acagcacatc aaagagatcg ctgatggtat 60
cggtgtgagc gtcgcagaac attacattga cgcaggtgat cggacgcgtc gggtcgagtt 120
tacgcgttgc ttccgccagt ggcgcgaaat attcccgtgc accttgcgga cgggtatccg 180
gttcgttggc aatactccac atcaccacgc ttgggtggtt tttgtcacgc gctatcagct 240
ctttaatcgc ctgtaagtgc gcttgctgag tttccccgtt gactgcctct tcgctgtaca 300
gttctttcgg cttgttgccc gcttcgaaac caatgcctaa agagaggtta aagccgacag 360
cagcagtttc atcaatcacc acgatgccat gttcatctgc ccagtcgagc atctcttcag 420
cgtaagggta atgcgaggta cggtaggagt tggccccaat ccagtccatt aatgcgtggt 480
cgtgcaccat cagcacgtta tcgaatcctt tgccacgcaa gtccgcatct tcatgacgac 540
caaagccagt aaagtagaac ggtttgtggt taatcaggaa ctgttcgccc ttcactgcca 600
ctgaccggat gccgacgcga agcgggtaga tatcacactc tgtctggctt ttggctgtga 660
cgcacagttc atagagataa ccttcacccg gttgccagag gtgcggattc accacttgca 720
aagtcccgct agtgccttgt ccagttgcaa ccacctgttg atccgcatca cgcagttcaa 780
cgctgacatc accattggcc accacctgcc agtcaacaga cgcgtggtta cagtcttgcg 840
cgacatgcgt caccacggtg atatcgtcca cccaggtgtt cggcgtggtg tagagcatta 900
cgctgcgatg gattccggca tagttaaaga aatcatggaa gtaagactgc tttttcttgc 960
cgttttcgtc ggtaatcacc attcccggcg ggatagtctg ccagttcagt tcgttgttca 1020
cacaaacggt gatacgtaca cttttcccgg caataacata cggcgtgaca tcggcttcaa 1080
atggcgtata gccgccctga tgctccatca cttcctgatt attgacccac actttgccgt 1140

-continued

```
aatgagtgac cgcatcgaaa cgcagcacga tacgctggcc tgcccaacct ttcggtataa   1200

agacttcgcg ctgataccag acgttgcccg cataattacg aatatctgca tcggcgaact   1260

gatcgttaaa actgcctggc acagcaattg cccggctttc ttgtaacgcg ctttcccacc   1320

aacgctgatc aattccacag ttttcgcgat aggtaaggta aatattaatg agtttatcga   1380

tctgtcaaag tctgagaaac ttctcccgtc gatgttcacg cctgtaaaga gtgttatggt   1440

ttcaaaggtt gataagatta tggtccatga aaatgaatca ttgtctgaag taaatctctt   1500

aaaaggtgta aaacttatag aaggtgggta tgtttgctta gtcggtcttg ttgtgtccgg   1560

tgagtggaat ttaccagata attgccgtgg tggtgtgagt gtctgcatgg ttgacaagag   1620

aatggaaaga gcggacgaag ccacactggg gtcatattac actgctgctg ctaaaaagcg   1680

gtttcagttt aaagtggtcc caaattacgg tattacaaca aaggatgcag aaaagaacat   1740

atggcaggtc ttagtaaata ttaaaaatgt aaaaatgagt gcgggctact gccctttgtc   1800

attagaattt gtgtctgtgt gtattgttta taaaaataat ataaaattgg gtttgaggga   1860

gaaagtaacg agtgtgaacg atggaggacc catggaactt tcggaagaag ttgttgatga   1920

gttcatggag aatgttccaa tgtcggttag actcgcaaag tttcgaacca aatcctcaaa   1980

aagaggtccg aaaaataata ataatttagg taaggggcgt tcaggcggaa ggcctaaacc   2040

aaaaagtttt gatgaagttg aaaaagagtt tgataatttg attgaagatg aagccgagac   2100

gtcggtcgcg gattctgatt cgtattaa                                      2128
```

<210> SEQ ID NO 7
<211> LENGTH: 2128
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa ttaacggttc aggcacagca catcaaagag atcgctgatg    180

gtatcggtgt gagcgtcgca gaacattaca ttgacgcagg tgatcggacg cgtcgggtcg    240

agtttacgcg ttgcttccgc cagtggcgcg aaatattccc gtgcaccttg cggacgggta    300

tccggttcgt tggcaatact ccacatcacc acgcttgggt ggtttttgtc acgcgctatc    360

agctctttaa tcgcctgtaa gtgcgcttgc tgagtttccc cgttgactgc ctcttcgctg    420

tacagttctt tcggcttgtt gcccgcttcg aaaccaatgc ctaaagagag gttaaagccg    480

acagcagcag tttcatcaat caccacgatg ccatgttcat ctgcccagtc gagcatctct    540

tcagcgtaag ggtaatgcga ggtacggtag gagttggccc caatccagtc cattaatgcg    600

tggtcgtgca ccatcagcac gttatcgaat cctttgccac gcaagtccgc atcttcatga    660

cgaccaaagc cagtaaagta gaacggtttg tggttaatca ggaactgttc gcccttcact    720

gccactgacc ggatgccgac gcgaagcggg tagatatcac actctgtctg gcttttggct    780

gtgacgcaca gttcatagag ataaccttca cccggttgcc agaggtgcgg attcaccact    840

tgcaaagtcc cgctagtgcc ttgtccagtt gcaaccacct gttgatccgc atcacgcagt    900

tcaacgctga catcaccatt ggccaccacc tgccagtcaa cagacgcgtg gttacagtct    960

tgcgcgacat gcgtcaccac ggtgatatcg tccacccagg tgttcggcgt ggtgtagagc   1020
```

-continued attacgctgc gatggattcc ggcatagtta aagaaatcat ggaagtaaga ctgcttttc 1080 ttgccgtttt cgtcggtaat caccattccc ggcgggatag tctgccagtt cagttcgttg 1140
ttcacacaaa cggtgatacg tacacttttc ccggcaataa catacggcgt gacatcggct 1200
tcaaatggcg tatagccgcc ctgatgctcc atcacttcct gattattgac ccacactttg 1260
ccgtaatgag tgaccgcatc gaaacgcagc acgatacgct ggcctgccca acctttcggt 1320
ataaagactt cgcgctgata ccagacgttg cccgcataat tacgaatatc tgcatcggcg 1380
aactgatcgt taaaactgcc tggcacagca attgcccggc tttcttgtaa cgcgctttcc 1440
caccaacgct gatcaattcc acagttttcg cgatgaatca ttgtctgaag taaatctctt 1500
aaaaggtgta aaacttatag aaggtgggta tgtttgctta gtcggtcttg ttgtgtccgg 1560
tgagtggaat ttaccagata attgccgtgg tggtgtgagt gtctgcatgg ttgacaagag 1620
aatggaaaga gcggacgaag ccacactggg gtcatattac actgctgctg ctaaaaagcg 1680
gtttcagttt aaagtggtcc caaattacgg tattacaaca aaggatgcag aaaagaacat 1740
atggcaggtc ttagtaaata ttaaaaatgt aaaaatgagt gcgggctact gccctttgtc 1800
attagaattt gtgtctgtgt gtattgttta taaaaataat ataaaattgg gtttgaggga 1860
gaaagtaacg agtgtgaacg atggaggacc catggaactt tcggaagaag ttgttgatga 1920
gttcatggag aatgttccaa tgtcggttag actcgcaaag tttcgaacca aatcctcaaa 1980
aagaggtccg aaaaataata ataatttagg taaggggcgt tcaggcggaa ggcctaaacc 2040
aaaaagtttt gatgaagttg aaaaagagtt tgataatttg attgaagatg aagccgagac 2100
gtcggtcgcg gattctgatt cgtattaa 2128

<210> SEQ ID NO 8
<211> LENGTH: 2133
<212> TYPE: DNA
<213> ORGANISM: Artificial Sequence
<220> FEATURE:
<223> OTHER INFORMATION: Description of Artificial Sequence: Synthetic DNA

<400> SEQUENCE: 8
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg tgtgagtaac ggttcaggca cagcacatca aagagatcgc 300
tgatggtatc ggtgtgagcg tcgcagaaca ttacattgac gcaggtgatc ggacgcgtcg 360
ggtcgagttt acgcgttgct tccgccagtg gcgcgaaata ttcccgtgca ccttgcggac 420
gggtatccgg ttcgttggca atactccaca tcaccacgct tgggtggttt ttgtcacgcg 480
ctatcagctc tttaatcgcc tgtaagtgcg cttgctgagt ttccccgttg actgcctctt 540
cgctgtacag ttctttcggc ttgttgcccg cttcgaaacc aatgcctaaa gagaggttaa 600
agccgacagc agcagtttca tcaatcacca cgatgccatg ttcatctgcc cagtcgagca 660
tctcttcagc gtaagggtaa tgcgaggtac ggtaggagtt ggccccaatc cagtccatta 720
atgcgtggtc gtgcaccatc agcacgttat cgaatccttt gccacgcaag tccgcatctt 780
catgacgacc aaagccagta aagtagaacg gtttgtggtt aatcaggaac tgttcgccct 840
tcactgccac tgaccggatg ccgacgcgaa gcgggtagat atcacactct gtctggcttt 900
tggctgtgac gcacagttca tagagataac cttcacccgg ttgccagagg tgcggattca 960
ccacttgcaa agtcccgcta gtgccttgtc cagttgcaac cacctgttga tccgcatcac 1020
gcagttcaac gctgacatca ccattggcca ccacctgcca gtcaacagac gcgtggttac 1080
agtcttgcgc gacatgcgtc accacggtga tatcgtccac ccaggtgttc ggcgtggtgt 1140
agagcattac gctgcgatgg attccggcat agttaaagaa atcatggaag taagactgct 1200
ttttcttgcc gttttcgtcg gtaatcacca ttcccggcgg gatagtctgc cagttcagtt 1260
cgttgttcac acaaacggtg atacgtacac ttttcccggc aataacatac ggcgtgacat 1320
cggcttcaaa tggcgtatag ccgccctgat gctccatcac ttcctgatta ttgacccaca 1380
ctttgccgta atgagtgacc gcatcgaaac gcagcacgat acgctggcct gcccaacctt 1440
tcggtataaa gacttcgcgc tgataccaga cgttgcccgc ataattacga atatctgcat 1500
cggcgaactg atcgttaaaa ctgcctggca cagcaattgc ccggctttct tgtaacgcgc 1560
tttcccacca acgctgatca attccacagt tttcgcgatg tgagtgtctg catggttgac 1620
aagagaatgg aaagagcgga cgaagccaca ctggggtcat attacactgc tgctgctaaa 1680
aagcggtttc agtttaaagt ggtcccaaat tacggtatta caacaaagga tgcagaaaag 1740
aacatatggc aggtcttagt aaatattaaa aatgtaaaaa tgagtgcggg ctactgccct 1800
ttgtcattag aatttgtgtc tgtgtgtatt gtttataaaa ataatataaa attgggtttg 1860
agggagaaag taacgagtgt gaacgatgga ggacccatgg aactttcgga agaagttgtt 1920
gatgagttca tggagaatgt tccaatgtcg gttagactcg caaagtttcg aaccaaatcc 1980
tcaaaaagag gtccgaaaaa taataataat ttaggtaagg ggcgttcagg cggaaggcct 2040
aaaccaaaaa gttttgatga agttgaaaaa gagtttgata atttgattga agatgaagcc 2100
gagacgtcgg tcgcggattc tgattcgtat taa 2133

<210> SEQ ID NO 9
<211> LENGTH: 2128
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg tgtgagtgtc tgcatggttg acaagagaat ggaaagagcg 300
gacgaagcca cactggggtc atattacact gctgctgcta aaaagcggtt tcagtttaaa 360
gtggtcccaa attacggtat tacaacaaag gatgcagaaa agaacatatg gcaggtctta 420
gtaaatatta aaaatgtaaa aatgagtgcg ggctactgcc ctttgtcatt agaatttgtg 480
tctgtgtgta ttgtttataa aaataatata aaattgggtt tgagggagaa agtaacgagt 540
gtgaacgatg gaggacccat ggaactttcg gaagaagttg ttgatgagtt catggagaat 600
gttccaatgt cggttagact taacggttca ggcacagcac atcaaagaga tcgctgatgg 660
tatcggtgtg agcgtcgcag aacattacat tgacgcaggt gatcggacgc gtcgggtcga 720
gtttacgcgt tgcttccgcc agtggcgcga aatattcccg tgcaccttgc ggacgggtat 780
ccggttcgtt ggcaatactc cacatcacca cgcttgggtg gtttttgtca cgcgctatca 840

```
gctctttaat cgcctgtaag tgcgcttgct gagtttcccc gttgactgcc tcttcgctgt    900

acagttcttt cggcttgttg cccgcttcga aaccaatgcc taaagagagg ttaaagccga    960

cagcagcagt ttcatcaatc accacgatgc catgttcatc tgcccagtcg agcatctctt   1020

cagcgtaagg gtaatgcgag gtacggtagg agttggcccc aatccagtcc attaatgcgt   1080

ggtcgtgcac catcagcacg ttatcgaatc ctttgccacg caagtccgca tcttcatgac   1140

gaccaaagcc agtaaagtag aacggtttgt ggttaatcag gaactgttcg cccttcactg   1200

ccactgaccg gatgccgacg cgaagcgggt agatatcaca ctctgtctgg cttttggctg   1260

tgacgcacag ttcatagaga taaccttcac ccggttgcca gaggtgcgga ttcaccactt   1320

gcaaagtccc gctagtgcct tgtccagttg caaccacctg ttgatccgca tcacgcagtt   1380

caacgctgac atcaccattg gccaccacct gccagtcaac agacgcgtgg ttacagtctt   1440

gcgcgacatg cgtcaccacg gtgatatcgt ccacccaggt gttcggcgtg gtgtagagca   1500

ttacgctgcg atggattccg gcatagttaa agaaatcatg gaagtaagac tgctttttct   1560

tgccgttttc gtcggtaatc accattcccg gcgggatagt ctgccagttc agttcgttgt   1620

tcacacaaac ggtgatacgt acacttttcc cggcaataac atacggcgtg acatcggctt   1680

caaatggcgt atagccgccc tgatgctcca tcacttcctg attattgacc cacactttgc   1740

cgtaatgagt gaccgcatcg aaacgcagca cgatacgctg gcctgcccaa cctttcggta   1800

taaagacttc gcgctgatac cagacgttgc ccgcataatt acgaatatct gcatcggcga   1860

actgatcgtt aaaactgcct ggcacagcaa ttgcccggct ttcttgtaac gcgctttccc   1920

accaacgctg atcaattcca cagttttcgc gatcgcaaag tttcgaacca aatcctcaaa   1980

aagaggtccg aaaaataata ataatttagg taaggggcgt tcaggcggaa ggcctaaacc   2040

aaaaagtttt gatgaagttg aaaaagagtt tgataatttg attgaagatg aagccgagac   2100

gtcggtcgcg gattctgatt cgtattaa                                      2128
```

<210> SEQ ID NO 10
<211> LENGTH: 2128
<212> TYPE: DNA
<213> ORGANISM: Artificial Sequence
<220> FEATURE:
<223> OTHER INFORMATION: Description of Artificial Sequence: Synthetic DNA

<400> SEQUENCE: 10

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtc ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagtttaaa    360

gtggtcccaa attacggtat tacaacaaag gatgcagaaa agaacatatg gcaggtctta    420

gtaaatatta aaaatgtaaa aatgagtgcg ggctactgcc ctttgtcatt agaatttgtg    480

tctgtgtgta ttgtttataa aaataatata aaattgggtt tgagggagaa agtaacgagt    540

gtgaacgatg gaggacccat ggaactttcg gaagaagttg ttgatgagtt catggagaat    600

gttccaatgt cggttagact cgcaaagttt cgaaccaaat cctcaaaaag aggtccgaaa    660

aataataata atttaggtaa ggggcgttca ggcggaaggc ctaaaccaaa aagttttgat    720

gaagttgaaa aagagtttga taatttgatt gaagatgaag ccgagacgtc ggtcgcggat    780
```

-continued tctgattcta acggttcagg cacagcacat caaagagatc gctgatggta tcggtgtgag 840
cgtcgcagaa cattacattg acgcaggtga tcggacgcgt cgggtcgagt ttacgcgttg 900
cttccgccag tggcgcgaaa tattcccgtg caccttgcgg acgggtatcc ggttcgttgg 960
caatactcca catcaccacg cttgggtggt ttttgtcacg cgctatcagc tctttaatcg 1020
cctgtaagtg cgcttgctga gtttccccgt tgactgcctc ttcgctgtac agttctttcg 1080
gcttgttgcc cgcttcgaaa ccaatgccta aagagaggtt aaagccgaca gcagcagttt 1140
catcaatcac cacgatgcca tgttcatctg cccagtcgag catctcttca gcgtaagggt 1200
aatgcgaggt acggtaggag ttggccccaa tccagtccat taatgcgtgg tcgtgcacca 1260
tcagcacgtt atcgaatcct ttgccacgca agtccgcatc ttcatgacga ccaaagccag 1320
taaagtagaa cggtttgtgg ttaatcagga actgttcgcc cttcactgcc actgaccgga 1380
tgccgacgcg aagcgggtag atatcacact ctgtctggct tttggctgtg acgcacagtt 1440
catagagata accttcaccc ggttgccaga ggtgcggatt caccacttgc aaagtcccgc 1500
tagtgccttg tccagttgca accacctgtt gatccgcatc acgcagttca acgctgacat 1560
caccattggc caccacctgc cagtcaacag acgcgtggtt acagtcttgc gcgacatgcg 1620
tcaccacggt gatatcgtcc acccaggtgt tcggcgtggt gtagagcatt acgctgcgat 1680
ggattccggc atagttaaag aaatcatgga agtaagactg ctttttcttg ccgttttcgt 1740
cggtaatcac cattcccggc gggatagtct gccagttcag ttcgttgttc acacaaacgg 1800
tgatacgtac acttttcccg gcaataacat acggcgtgac atcggcttca aatggcgtat 1860
agccgccctg atgctccatc acttcctgat tattgaccca cactttgccg taatgagtga 1920
ccgcatcgaa acgcagcacg atacgctggc ctgcccaacc tttcggtata aagacttcgc 1980
gctgatacca gacgttgccc gcataattac gaatatctgc atcggcgaac tgatcgttaa 2040
aactgcctgg cacagcaatt gcccggcttt cttgtaacgc gctttcccac caacgctgat 2100
caattccaca gttttcgcga tgtattaa 2128

<210> SEQ ID NO 11
<211> LENGTH: 2134
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 11
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg tgtgagtgtc tgcatggttg acaagagaat ggaaagagcg 300
gacgaagcca cactggggtc atattacact gctgctgcta aaaagcggtt tcagtttaaa 360
gtggtcccaa attacggtat tacaacaaag gatgcagaaa agaacatatg gcaggtctta 420
gtaaatatta aaaatgtaaa aatgagtgcg ggctactgcc ctttgtcatt agaatttgtg 480
tctgtgtgta ttgtttataa aaataatata aaattgggtt tgagggagaa agtaacgagt 540
gtgaacgatg gaggacccat ggaactttcg gaagaagttg ttgatgagtt catggagaat 600
gttccaatgt cggttagact cgcaaagttt cgaaccaaat cctcaaaaag aggtccgaaa 660

-continued

```
aataataata atttaggtaa ggggcgttca ggcggaaggc ctaaaccaaa aagttttgat    720

gaagttgaaa aagagtttga taatttgatt gaagatgaag ccgagacgtc ggtcgcggat    780

tctgattcgt attaaatcgg ataacggttc aggcacagca catcaaagag atcgctgatg    840

gtatcggtgt gagcgtcgca gaacattaca ttgacgcagg tgatcggacg cgtcgggtcg    900

agtttacgcg ttgcttccgc cagtggcgcg aaatattccc gtgcaccttg cggacgggta    960

tccggttcgt tggcaatact ccacatcacc acgcttgggt ggtttttgtc acgcgctatc   1020

agctctttaa tcgcctgtaa gtgcgcttgc tgagtttccc cgttgactgc ctcttcgctg   1080

tacagttctt tcggcttgtt gcccgcttcg aaaccaatgc ctaaagagag gttaaagccg   1140

acagcagcag tttcatcaat caccacgatg ccatgttcat ctgcccagtc gagcatctct   1200

tcagcgtaag ggtaatgcga ggtacggtag gagttggccc caatccagtc cattaatgcg   1260

tggtcgtgca ccatcagcac gttatcgaat cctttgccac gcaagtccgc atcttcatga   1320

cgaccaaagc cagtaaagta gaacggtttg tggttaatca ggaactgttc gcccttcact   1380

gccactgacc ggatgccgac gcgaagcggg tagatatcac actctgtctg gcttttggct   1440

gtgacgcaca gttcatagag ataaccttca cccggttgcc agaggtgcgg attcaccact   1500

tgcaaagtcc cgctagtgcc ttgtccagtt gcaaccacct gttgatccgc atcacgcagt   1560

tcaacgctga catcaccatt ggccaccacc tgccagtcaa cagacgcgtg gttacagtct   1620

tgcgcgacat gcgtcaccac ggtgatatcg tccacccagg tgttcggcgt ggtgtagagc   1680

attacgctgc gatggattcc ggcatagtta aagaaatcat ggaagtaaga ctgctttttc   1740

ttgccgtttt cgtcggtaat caccattccc ggcgggatag tctgccagtt cagttcgttg   1800

ttcacacaaa cggtgatacg tacacttttc ccggcaataa catacggcgt gacatcggct   1860

tcaaatggcg tatagccgcc ctgatgctcc atcacttcct gattattgac ccacactttg   1920

ccgtaatgag tgaccgcatc gaaacgcagc acgatacgct ggcctgccca acctttcggt   1980

ataaagactt cgcgctgata ccagacgttg cccgcataat tacgaatatc tgcatcggcg   2040

aactgatcgt taaaactgcc tggcacagca attgcccggc tttcttgtaa cgcgctttcc   2100

caccaacgct gatcaattcc acagttttcg cgat                                2134
```

<210> SEQ ID NO 12
<211> LENGTH: 1395
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtc ggtcttgttg tgtccggtga gtggaattta    240

ccagataatt gccgtggtgg tccacctgtt gatccgcatc acgcagttca acgctgacat    300

caccattggc caccacctgc cagtcaacag acgcgtggtt acagtcttgc gcgacatgcg    360

tcaccacggt gatatcgtcc acccaggtgt tcggcgtggt gtagagcatt acgctgcgat    420

ggattccggc atagttaaag aaatcatgga agtaagactg ctttttcttg ccgttttcgt    480

cggtaatcac cattcccggc gggatagtct gccagttcag ttcgttgttc acacaaacgg    540

tgatacgtac acttttcccg gcaataacat acggcgtgac atcggcttca aatggcgtat    600
```

-continued agccgccctg atgctccatc acttcctgat tattgaccca cactttgccg taatgagtga 660
ccgcatcgaa acgcagcacg atacgctggc ctgcccaacc tttcggtata aagacttcgc 720
gctgatacca gacgttgccc gcataattac gaatatctgc atcggcgaac tgatcgttaa 780
aactgcctgg cacagcaatt gcccggcttt cttgtaacgc gctttcccac caacgctgat 840
caattccaca gttttcgcga tgtgagtgtc tgcatggttg acaagagaat ggaaagagcg 900
gacgaagcca cactggggtc atattacact gctgctgcta aaaagcggtt tcagtttaaa 960
gtggtcccaa attacggtat tacaacaaag gatgcagaaa agaacatatg gcaggtctta 1020
gtaaatatta aaaatgtaaa aatgagtgcg ggctactgcc ctttgtcatt agaatttgtg 1080
tctgtgtgta ttgtttataa aaataatata aaattgggtt tgagggagaa agtaacgagt 1140
gtgaacgatg gaggacccat ggaactttcg gaagaagttg ttgatgagtt catggagaat 1200
gttccaatgt cggttagact cgcaaagttt cgaaccaaat cctcaaaaag aggtccgaaa 1260
aataataata atttaggtaa ggggcgttca ggcggaaggc ctaaaccaaa aagttttgat 1320
gaagttgaaa aagagtttga taatttgatt gaagatgaag ccgagacgtc ggtcgcggat 1380
tctgattcgt attaa 1395

<210> SEQ ID NO 13
<211> LENGTH: 1095
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 13
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg tcaataacat acggcgtgac atcggcttca aatggcgtat 300
agccgccctg atgctccatc acttcctgat tattgaccca cactttgccg taatgagtga 360
ccgcatcgaa acgcagcacg atacgctggc ctgcccaacc tttcggtata aagacttcgc 420
gctgatacca gacgttgccc gcataattac gaatatctgc atcggcgaac tgatcgttaa 480
aactgcctgg cacagcaatt gcccggcttt cttgtaacgc gctttcccac caacgctgat 540
caattccaca gttttcgcga tgtgagtgtc tgcatggttg acaagagaat ggaaagagcg 600
gacgaagcca cactggggtc atattacact gctgctgcta aaaagcggtt tcagtttaaa 660
gtggtcccaa attacggtat tacaacaaag gatgcagaaa agaacatatg gcaggtctta 720
gtaaatatta aaaatgtaaa aatgagtgcg ggctactgcc ctttgtcatt agaatttgtg 780
tctgtgtgta ttgtttataa aaataatata aaattgggtt tgagggagaa agtaacgagt 840
gtgaacgatg gaggacccat ggaactttcg gaagaagttg ttgatgagtt catggagaat 900
gttccaatgt cggttagact cgcaaagttt cgaaccaaat cctcaaaaag aggtccgaaa 960
aataataata atttaggtaa ggggcgttca ggcggaaggc ctaaaccaaa aagttttgat 1020
gaagttgaaa aagagtttga taatttgatt gaagatgaag ccgagacgtc ggtcgcggat 1080
tctgattcgt attaa 1095

<210> SEQ ID NO 14

<211> LENGTH: 895
<212> TYPE: DNA
<213> ORGANISM: Artificial Sequence
<220> FEATURE:
<223> OTHER INFORMATION: Description of Artificial Sequence: Synthetic DNA

<400> SEQUENCE: 14
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg ttcggcgaac tgatcgttaa aactgcctgg cacagcaatt 300
gcccggcttt cttgtaacgc gctttcccac caacgctgat caattccaca gttttcgcga 360
tgtgagtgtc tgcatggttg acaagagaat ggaaagagcg gacgaagcca cactggggtc 420
atattacact gctgctgcta aaaagcggtt tcagtttaaa gtggtcccaa attacggtat 480
tacaacaaag gatgcagaaa agaacatatg gcaggtctta gtaaatatta aaaatgtaaa 540
aatgagtgcg ggctactgcc ctttgtcatt agaatttgtg tctgtgtgta ttgtttataa 600
aaataatata aaattgggtt tgagggagaa agtaacgagt gtgaacgatg gaggacccat 660
ggaactttcg gaagaagttg ttgatgagtt catggagaat gttccaatgt cggttagact 720
cgcaaagttt cgaaccaaat cctcaaaaag aggtccgaaa aataataata atttaggtaa 780
ggggcgttca ggcggaaggc ctaaaccaaa aagttttgat gaagttgaaa aagagtttga 840
taatttgatt gaagatgaag ccgagacgtc ggtcgcggat tctgattcgt attaa 895

<210> SEQ ID NO 15
<211> LENGTH: 2399
<212> TYPE: DNA
<213> ORGANISM: Artificial Sequence
<220> FEATURE:
<223> OTHER INFORMATION: Description of Artificial Sequence: Synthetic DNA

<400> SEQUENCE: 15
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa tgaatcattg tctgaagtaa atctcttaaa aggtgtaaaa 180
cttatagaag gtgggtatgt ttgcttagtc ggtcttgttg tgtccggtga gtggaattta 240
ccagataatt gccgtggtgg ttcattgttt gcctccctgc tgcggttttt caccgaagtt 300
catgccagtc cagcgttttt gcagcagaaa agccgccgac ttcggtttgc ggtcgcgagt 360
gaagatccct ttcttgttac cgccaacgcg caatatgcct tgcgaggtcg caaaatcggc 420
gaaattccat acctgttcac cgacgacggc gctgacgcga tcaaagacgc ggtgatacat 480
atccagccat gcacactgat actcttcact ccacatgtcg gtgtacattg agtgcagccc 540
ggctaacgta tccacgccgt attcggtgat gataatcggc tgatgcagtt tctcctgcca 600
ggccagaagt tctttttcca gtaccttctc tgccgtttcc aaatcgccgc tttggacata 660
ccatccgtaa taacggttca ggcacagcac atcaaagaga tcgctgatgg tatcggtgtg 720
agcgtcgcag aacattacat tgacgcaggt gatcggacgc gtcgggtcga gtttacgcgt 780
tgcttccgcc agtggcgcga aatattcccg tgcaccttgc ggacgggtat ccggttcgtt 840
ggcaatactc cacatcacca cgcttgggtg gtttttgtca cgcgctatca gctctttaat 900

-continued

```
cgcctgtaag tgcgcttgct gagtttcccc gttgactgcc tcttcgctgt acagttcttt    960

cggcttgttg cccgcttcga aaccaatgcc taaagagagg ttaaagccga cagcagcagt   1020

ttcatcaatc accacgatgc catgttcatc tgcccagtcg agcatctctt cagcgtaagg   1080

gtaatgcgag gtacggtagg agttggcccc aatccagtcc attaatgcgt ggtcgtgcac   1140

catcagcacg ttatcgaatc ctttgccacg caagtccgca tcttcatgac gaccaaagcc   1200

agtaaagtag aacggtttgt ggttaatcag gaactgttcg cccttcactg ccactgaccg   1260

gatgccgacg cgaagcgggt agatatcaca ctctgtctgg cttttggctg tgacgcacag   1320

ttcatagaga taaccttcac ccggttgcca gaggtgcgga ttcaccactt gcaaagtccc   1380

gctagtgcct tgtccagttg caaccacctg ttgatccgca tcacgcagtt caacgctgac   1440

atcaccattg gccaccacct gccagtcaac agacgcgtgg ttacagtctt gcgcgacatg   1500

cgtcaccacg gtgatatcgt ccacccaggt gttcggcgtg gtgtagagca ttacgctgcg   1560

atggattccg gcatagttaa agaaatcatg gaagtaagac tgctttttct tgccgttttc   1620

gtcggtaatc accattcccg gcgggatagt ctgccagttc agttcgttgt tcacacaaac   1680

ggtgatacgt acacttttcc cggcaataac atacggcgtg acatcggctt caaatggcgt   1740

atagccgccc tgatgctcca tcacttcctg attattgacc cacactttgc cgtaatgagt   1800

gaccgcatcg aaacgcagca cgatacgctg gcctgcccaa ccccccaaag atgtcctgca   1860

ttgtagtgag tgtctgcatg gttgacaaga gaatggaaag agcggacgaa gccacactgg   1920

ggtcatatta cactgctgct gctaaaaagc ggtttcagtt taaagtggtc ccaaattacg   1980

gtattacaac aaaggatgca gaaaagaaca tatggcaggt cttagtaaat attaaaaatg   2040

taaaaatgag tgcgggctac tgccctttgt cattagaatt tgtgtctgtg tgtattgttt   2100

ataaaaataa tataaaattg ggtttgaggg agaaagtaac gagtgtgaac gatggaggac   2160

ccatggaact ttcggaagaa gttgttgatg agttcatgga gaatgttcca atgtcggtta   2220

gactcgcaaa gtttcgaacc aaatcctcaa aaagaggtcc gaaaaataat aataatttag   2280

gtaaggggcg ttcaggcgga aggcctaaac caaaaagttt tgatgaagtt gaaaaagagt   2340

ttgataattt gattgaagat gaagccgaga cgtcggtcgc ggattctgat tcgtattaa    2399
```

<210> SEQ ID NO 16
<211> LENGTH: 796
<212> TYPE: DNA
<213> ORGANISM: Artificial Sequence
<220> FEATURE:
<223> OTHER INFORMATION: Description of Artificial Sequence: Synthetic DNA

<400> SEQUENCE: 16

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tcccaggtgt tcggcgtggt gtagagcatt acgctgcgat    180

ggattccggc atagttaaag aaatcatgga agtaagactg ctttttcttg ccgttttcgt    240

cggtaatcac cattcccggc gggatagtct gccagttcag ttcgttgttc acacaaacgg    300

tgatacgtac acttttcccg gcaataacat acggcgtgac atcggcttca aatggcgtat    360

agccgccctg atgctccatc acttcctgat tattgaccca cactttgccg taatgagtga    420

ccgcatcgaa acgcagcacg atacgctggc ctgcccaacc tttcggtata aagacttcgc    480

gctgatacca gacgttgccc gcataattac gaatatctgc atcggcgaac tgatcgttaa    540

aactgcctgg cacagcaatt gcccggcttt cttgtaacgc gctttcccac caacgctgat    600
```

caattccaca gttttcgcga tcgcaaagtt tcgaaccaaa tcctcaaaaa gaggtccgaa 660
aaataataat aatttaggta aggggcgttc aggcggaagg cctaaaccaa aaagttttga 720
tgaagttgaa aaagagtttg ataatttgat tgaagatgaa gccgagacgt cggtcgcgga 780
ttctgattcg tattaa 796

<210> SEQ ID NO 17
<211> LENGTH: 1649
<212> TYPE: DNA
<213> ORGANISM: Artificial Sequence
<220> FEATURE:
<223> OTHER INFORMATION: Description of Artificial Sequence: Synthetic DNA

<400> SEQUENCE: 17
atggctctag ttgttaaagg taaggtaaat attaatgagt ttatcgatct gtcaaagtct 60
gagaaacttc tcccgtcgat gttcacgcct gtaaagagtg ttatggtttc aaaggttgat 120
aagattatgg tccatgaaaa ttaacggttc aggcacagca catcaaagag atcgctgatg 180
gtatcggtgt gagcgtcgca gaacattaca ttgacgcagg tgatcggacg cgtcgggtcg 240
agtttacgcg ttgcttccgc cagtggcgcg aaatattccc gtgcaccttg cggacgggta 300
tccggttcgt tggcaatact ccacatcacc acgcttgggt ggtttttgtc acgcgctatc 360
agctctttaa tcgcctgtaa gtgcgcttgc tgagtttccc cgttgactgc ctcttcgctg 420
tacagttctt tcggcttgtt gcccgcttcg aaaccaatgc ctaaagagag gttaaagccg 480
acagcagcag tttcatcaat caccacgatg ccatgttcat ctgcccagtc gagcatctct 540
tcagcgtaag ggtaatgcga ggtacggtag gagttggccc caatccagtc cattaatgcg 600
tggtcgtgca ccatcagcac gttatcgaat cctttgccac gcaagtccgc atcttcatga 660
cgaccaaagc cagtaaagta gaacggtttg tggttaatca ggaactgttc gcccttcact 720
gccactgacc ggatgccgac gcgaagcggg tagatatcac actctgtctg gcttttggct 780
gtgacgcaca gttcatagag ataaccttca cccggttgcc agaggtgcgg attcaccact 840
tgcaaagtcc cgctagtgcc ttgtccagtt gcaaccacct gttgatccgc atcacgcagt 900
tcaacgctga catcaccatt ggccaccacc tgccagtcaa cagacgcgtg gttacagtct 960
tgcgcgacat gcgtcaccac ggtgatatcg tccacccagg tgttcggcgt ggtgtagagc 1020
attacgctgc gatggattcc ggcatagtta aagaaatcat ggaagtaaga ctgctttttc 1080
ttgccgtttt cgtcggtaat caccattccc ggcgggatag tctgccagtt cagttcgttg 1140
ttcacacaaa cggtgatacg tacacttttc ccggcaataa catacggcgt gacatcggct 1200
tcaaatggcg tatagccgcc ctgatgctcc atcacttcct gattattgac ccacactttg 1260
ccgtaatgag tgaccgcatc gaaacgcagc acgatacgct ggcctgccca acctttcggt 1320
ataaagactt cgcgctgata ccagacgttg cccgcataat tacgaatatc tgcatcggcg 1380
aactgatcgt taaaactgcc tggcacagca attgcccggc tttcttgtaa cgcgctttcc 1440
caccaacgct gatcaattcc acagttttcg cgatcgcaaa gtttcgaacc aaatcctcaa 1500
aaagaggtcc gaaaaataat aataatttag gtaaggggcg ttcaggcgga aggcctaaac 1560
caaaaagttt tgatgaagtt gaaaaagagt ttgataattt gattgaagat gaagccgaga 1620
cgtcggtcgc ggattctgat tcgtattaa 1649

<210> SEQ ID NO 18
<211> LENGTH: 3351
<212> TYPE: DNA

<213> ORGANISM: Tomato mosaic virus

<400> SEQUENCE: 18

```
atggcataca cacaaacagc cacatcgtcc gctttgcttg agaccgtccg aggtaacaat      60
accttggtca acgatcttgc aaagcggcgt ctatatgaca cagcggtcga tgaatttaat     120
gctagggacc gcaggcctaa agtcaatttt tccaaagtag taagcgaaga acagacgctt     180
attgcaacca aagcctaccc agaattccaa attacattct acaacacgca gaatgctgtg     240
cattcccttg caggcggtct ccgatcatta gaattggaat atctgatgat gcaaattccc     300
tacggatcat tgacatatga tatcggaggt aattttgcat ctcatctgtt caaagggcga     360
gcatacgttc actgctgtat gccgaatctg gatgtccgcg acataatgcg gcacgagggc     420
caaaaggaca gtattgaact atacctttct aggctcgaga ggggcaacaa acatgtccca     480
aacttccaaa aggaagcttt cgacagatac gctgaaatgc caaacgaagt agtctgtcac     540
gatactttcc aaacgtgtag gcattctcaa gaatgttaca cgggaagagt gtatgctatt     600
gctttgcata gtatatacga tatacctgcc gacgagttcg gcgcggcact gctgagaaag     660
aatgtacatg tatgttatgc cgctttccac ttttccgaga atttacttct cgaagattca     720
cacgtcaacc tcgacgagat caatgcatgt ttccaaagag atggagacag gttgactttt     780
tcctttgcat ctgagagtac tcttaattat agtcatagtt attctaatat tcttaagtat     840
gtttgcaaaa cttacttccc agcctctaat agagaggttt acatgaagga gtttttagta     900
actagagtta atacctggtt ttgtaaattt tctagaatag atactttctt attgtacaaa     960
ggtgtagcgc ataagggtgt agatagtgag cagttttaca aggctatgga agacgcatgg    1020
cactacaaaa agactcttgc gatgtgcaac agtgaaagaa tcttgttaga ggattcttca    1080
tcagttaatt actggtttcc aaaaatgagg gatatggtga tagttccact atttgacata    1140
tctctcgaga ctagtaaaag aacacgcaaa gaggtcttag tttcaaagga ctttgtttat    1200
acagtgttaa atcacattcg tacgtaccag gccaaagcgc ttacttactc caacgtgtta    1260
tctttcgtcg aatcaattcg ttcgagagtg atcattaacg ggttactgc taggtctgag    1320
tgggatgtcg ataaatcatt attacagtcc ttgtcgatga cgttcttcct acacaccaag    1380
cttgccgttc tgaaagacga tcttttgatt agcaagtttg cacttggacc aaaaactgtc    1440
tcacaacatg tgtgggatga gatttcccta gctttcggca atgctttccc atcgatcaag    1500
gaaagattga taaaccggaa actgatcaaa attacggaga atgcgttaga gatcagggtg    1560
cccgatcttt atgtcacttt ccatgatagg ttagtttctg agtacaaaat gtcagtggac    1620
atgccggtgc tagacattag gaaaaagatg gaagaaactg aggaaatgta caatgcactg    1680
tccgaactgt ctgtacttaa aaattcagac aagttcgatg ttgacgtttt ttcccagatg    1740
tgccaatctt tagaagtcga tccaatgact gcagcaaagg taatagtagc agttatgagc    1800
aacgagagtg gtcttactct cacgtttgaa cagcccaccg aagctaatgt tgcgctagca    1860
ttgcaagatt ctgaaaaggc ttctgatggg gcgttggtag ttacctcaag agatgttgag    1920
gaaccgtcca taaagggttc gatggcccgt ggtgagttac aattggccgg attatctggc    1980
gacgttcctg aatcttcata cactaggagc gaggagattg agtctctcga gcagtttcat    2040
atggcaacag ctagttcgtt aattcataag cagatgtgtt cgatcgtgta cacgggccct    2100
cttaaagttc aacaaatgaa aaactttata gacagcctgg tagcctcgct ctctgctgcg    2160
gtgtcgaatc tagtgaagat cctaaaagat acagccgcga ttgaccttga aactcgtcaa    2220
aagttcggag ttctggatgt tgcttcgaaa aggtggctag ttaaaccatc cgcaaagaac    2280
```

-continued catgcatggg gggttgttga gactcatgcg aggaaatatc acgtcgcatt actggagcac 2340
gatgaatttg gcattattac gtgcgataac tggcgacggg tggctgtgag ttctgagtcg 2400
gtagtatatt ctgatatggc taaactcagg actctgagaa gattgctcaa agatggagaa 2460
ccacacgtta gttcagcaaa ggtggttttg gtggatggcg ttccagggtg cgggaagaca 2520
aaggaaattc tttcgagagt taatttcgaa gaagatctaa ttcttgtccc tggtcgtcaa 2580
gctgccgaga tgatcagaag aagagctaat gcgtcgggca taatagtggc tacaaaggat 2640
aatgtgcgca ccgtcgattc atttttgatg aattacggga aaggggcacg ctgtcagttc 2700
aaaagattgt tcatagacga aggtttgatg ctgcatactg gttgtgtgaa tttttttggtt 2760 gaaatgtctc tgtgcgatat tgcatatgtt tatggagaca cccaacagat tccgtacatc 2820
aacagagtaa ctggtttccc gtaccctgca cactttgcaa aattggaggt cgacgaagtc 2880
gaaacaagaa gaactactct tcgttgtccg gctgatgtca cacacttcct aaatcaaagg 2940
tatgaaggac acgtaatgtg cacgtcttct gaaaagaaat cagtttccca ggaaatggtt 3000
agtggggctg cgtctatcaa tcctgtgtcc aagccgctta agggaaaaat tttgactttc 3060
acacagtctg acaaggaggc ccttctctca aggggctacg cagatgtcca tactgtacat 3120
gaggtacaag gtgagactta tgcagacgta tcgttagttc gactaacacc tacgcctgta 3180
tctatcatcg caagagacag tccgcatgtt ctggtctcgt tgtcaagaca cacaaaatcc 3240
ctaaagtact acaccgttgt gatggatcct ttagttagta tcattagaga tttagaacgg 3300
gttagtagtt acttattaga catgtacaaa gtagatgcag gtactcaata g 3351

<210> SEQ ID NO 19
<211> LENGTH: 4851
<212> TYPE: DNA
<213> ORGANISM: Tomato mosaic virus

<400> SEQUENCE: 19
atggcataca cacaaacagc cacatcgtcc gctttgcttg agaccgtccg aggtaacaat 60
accttggtca acgatcttgc aaagcggcgt ctatatgaca cagcggtcga tgaatttaat 120
gctagggacc gcaggcctaa agtcaatttt tccaaagtag taagcgaaga acagacgctt 180
attgcaacca aagcctaccc agaattccaa attacattct acaacacgca gaatgctgtg 240
cattcccttg caggcggtct ccgatcatta gaattggaat atctgatgat gcaaattccc 300
tacggatcat tgacatatga tatcggaggt aattttgcat ctcatctgtt caaagggcga 360
gcatacgttc actgctgtat gccgaatctg gatgtccgcg acataatgcg gcacgagggc 420
caaaaggaca gtattgaact atacctttct aggctcgaga ggggcaacaa acatgtccca 480
aacttccaaa aggaagcttt cgacagatac gctgaaatgc caaacgaagt agtctgtcac 540
gatactttcc aaacgtgtag gcattctcaa gaatgttaca cgggaagagt gtatgctatt 600
gctttgcata gtatatacga tatacctgcc gacgagttcg gcgcggcact gctgagaaag 660
aatgtacatg tatgttatgc cgctttccac ttttccgaga atttacttct cgaagattca 720
cacgtcaacc tcgacgagat caatgcatgt ttccaaagag atggagacag gttgactttt 780
tcctttgcat ctgagagtac tcttaattat agtcatagtt attctaatat tcttaagtat 840
gtttgcaaaa cttacttccc agcctctaat agagaggttt acatgaagga gtttttagta 900
actagagtta atacctggtt ttgtaaattt tctagaatag atactttctt attgtacaaa 960
ggtgtagcgc ataagggtgt agatagtgag cagttttaca aggctatgga agacgcatgg 1020
cactacaaaa agactcttgc gatgtgcaac agtgaaagaa tcttgttaga ggattcttca 1080

-continued

```
tcagttaatt actggtttcc aaaaatgagg gatatggtga tagttccact atttgacata   1140
tctctcgaga ctagtaaaag aacacgcaaa gaggtcttag tttcaaagga ctttgtttat   1200
acagtgttaa atcacattcg tacgtaccag gccaaagcgc ttacttactc caacgtgtta   1260
tctttcgtcg aatcaattcg ttcgagagtg atcattaacg gggttactgc taggtctgag   1320
tgggatgtcg ataaatcatt attacagtcc ttgtcgatga cgttcttcct acacaccaag   1380
cttgccgttc tgaaagacga tcttttgatt agcaagtttg cacttggacc aaaaactgtc   1440
tcacaacatg tgtgggatga gatttcccta gctttcggca atgctttccc atcgatcaag   1500
gaaagattga taaaccggaa actgatcaaa attacggaga atgcgttaga gatcagggtg   1560
cccgatcttt atgtcacttt ccatgatagg ttagtttctg agtacaaaat gtcagtggac   1620
atgccggtgc tagacattag gaaaaagatg gaagaaactg aggaaatgta caatgcactg   1680
tccgaactgt ctgtacttaa aaattcagac aagttcgatg ttgacgtttt ttcccagatg   1740
tgccaatctt tagaagtcga tccaatgact gcagcaaagg taatagtagc agttatgagc   1800
aacgagagtg gtcttactct cacgtttgaa cagcccaccg aagctaatgt tgcgctagca   1860
ttgcaagatt ctgaaaaggc ttctgatggg gcgttggtag ttacctcaag agatgttgag   1920
gaaccgtcca taaagggttc gatggcccgt ggtgagttac aattggccgg attatctggc   1980
gacgttcctg aatcttcata cactaggagc gaggagattg agtctctcga gcagtttcat   2040
atggcaacag ctagttcgtt aattcataag cagatgtgtt cgatcgtgta cacgggccct   2100
cttaaagttc aacaaatgaa aaactttata gacagcctgg tagcctcgct ctctgctgcg   2160
gtgtcgaatc tagtgaagat cctaaaagat acagccgcga ttgaccttga aactcgtcaa   2220
aagttcggag ttctggatgt tgcttcgaaa aggtggctag ttaaaccatc cgcaaagaac   2280
catgcatggg gggttgttga gactcatgcg aggaaatatc acgtcgcatt actggagcac   2340
gatgaatttg gcattattac gtgcgataac tggcgacggg tggctgtgag ttctgagtcg   2400
gtagtatatt ctgatatggc taaactcagg actctgagaa gattgctcaa agatggagaa   2460
ccacacgtta gttcagcaaa ggtggttttg gtggatggcg ttccagggtg cgggaagaca   2520
aaggaaattc tttcgagagt taatttcgaa gaagatctaa ttcttgtccc tggtcgtcaa   2580
gctgccgaga tgatcagaag aagagctaat gcgtcgggca taatagtggc tacaaaggat   2640
aatgtgcgca ccgtcgattc atttttgatg aattacggga aaggggcacg ctgtcagttc   2700
aaaagattgt tcatagacga aggtttgatg ctgcatactg gttgtgtgaa tttttttggtt   2760
gaaatgtctc tgtgcgatat tgcatatgtt tatggagaca cccaacagat tccgtacatc   2820
aacagagtaa ctggtttccc gtaccctgca cactttgcaa aattggaggt cgacgaagtc   2880
gaaacaagaa gaactactct tcgttgtccg gctgatgtca cacacttcct aaatcaaagg   2940
tatgaaggac acgtaatgtg cacgtcttct gaaaagaaat cagtttccca ggaaatggtt   3000
agtggggctg cgtctatcaa tcctgtgtcc aagccgctta agggaaaaat tttgactttc   3060
acacagtctg acaaggaggc ccttctctca aggggctacg cagatgtcca tactgtacat   3120
gaggtacaag gtgagactta tgcagacgta tcgttagttc gactaacacc tacgcctgta   3180
tctatcatcg caagagacag tccgcatgtt ctggtctcgt tgtcaagaca cacaaaatcc   3240
ctaaagtact acaccgttgt gatggatcct ttagttagta tcattagaga tttagaacgg   3300
gttagtagtt acttattaga catgtacaaa gtagatgcag gtactcaata gcaattacag   3360
gtcgactctg tgtttaaaaa tttcaatctt tttgtagcag ctccaaagac tggagatata   3420
tctgatatgc aattttacta tgataagtgt cttcctggga acagcacgtt gttgaacaac   3480
```

```
tacgacgctg ttaccatgaa attgactgac atttctctga atgtcaaaga ttgcatatta   3540

gatatgtcta agtctgtagc tgctccgaaa gatgtcaaac caactttaat accgatggta   3600

cgaacggcgg cagaaatgcc tcgccagact ggactgttgg aaaatctagt tgcgatgatt   3660

aaaagaaatt ttaattcacc agagttgtcc ggagtagttg atattgaaaa tactgcatct   3720

ttagtggtag ataagttttt tgatagttat ttacttaagg aaaaaagaaa accaaacaaa   3780

aatttttcac tgtttagtag agagtctctc aataggtgga tagcaaagca agaacaagtc   3840

acaattggtc agttggccga ttttgatttt gtggatcttc cagccgttga tcagtacagg   3900

catatgatta aagcgcaacc gaagcagaaa ctggatctgt caattcagac agaatatcca   3960

gcgttgcaaa cgattgtgta tcattcaaag aaaatcaacg caatatttgg tcctcttttc   4020

agtgagctta caaggcaatt acttgacagt attgactcaa gcagattctt gttctttacg   4080

agaaagacac cggctcagat cgaagatttc ttcggagatc tagacagtca tgtcccaatg   4140

gacgtacttg agttggatgt ttcgaagtat gataagtctc aaaacgagtt tcattgtgct   4200

gttgagtacg aaatctggag gagactgggt ctggaggatt tcttggcaga agtgtggaaa   4260

caagggcata gaaaaaccac tctgaaagat tacactgctg gtataaaaac gtgtttatgg   4320

taccagagaa agagtggtga tgttacaact tttatcggta ataccgtcat cattgcttcg   4380

tgtctagcat caatgctccc gatggaaaaa ttgataaaag gagccttctg cggagatgac   4440

agtttgttgt actttcctaa gggttgtgag tatcccgata tacaacaagc tgctaatcta   4500

atgtggaatt ttgaggccaa actgttcaag aagcaatatg ggtacttctg cgggaggtac   4560

gtgattcatc acgatagagg ttgcatagta tactacgacc ctttgaagct gatttcgaaa   4620

cttggtgcta aacacatcaa ggattgggat catttggagg agttcagaag atccctctgt   4680

gatgttgctg agtcgttgaa caattgcgcg tattacacac aattggacga cgctgttggg   4740

gaggttcata aaaccgcccc acctggttcg tttgtttata agagtttagt taagtatttg   4800

tcagataaag ttttgtttag aagtttattt cttgatggct ctagttgtta a            4851
```

<210> SEQ ID NO 20
<211> LENGTH: 795
<212> TYPE: DNA
<213> ORGANISM: Tomato mosaic virus

<400> SEQUENCE: 20

```
atggctctag ttgttaaagg taaggtaaat attaatgagt ttatcgatct gtcaaagtct     60

gagaaacttc tcccgtcgat gttcacgcct gtaaagagtg ttatggtttc aaaggttgat    120

aagattatgg tccatgaaaa tgaatcattg tctgaagtaa atctcttaaa aggtgtaaaa    180

cttatagaag gtgggtatgt ttgcttagtc ggtcttgttg tgtccggtga gtggaattta    240

ccagataatt gccgtggtgg tgtgagtgtc tgcatggttg acaagagaat ggaaagagcg    300

gacgaagcca cactggggtc atattacact gctgctgcta aaaagcggtt tcagtttaaa    360

gtggtcccaa attacggtat tacaacaaag gatgcagaaa agaacatatg gcaggtctta    420

gtaaatatta aaaatgtaaa aatgagtgcg ggctactgcc ctttgtcatt agaatttgtg    480

tctgtgtgta ttgtttataa aaataatata aaattgggtt tgagggagaa agtaacgagt    540

gtgaacgatg gaggacccat ggaactttcg gaagaagttg ttgatgagtt catggagaat    600

gttccaatgt cggttagact cgcaaagttt cgaaccaaat cctcaaaaag aggtccgaaa    660

aataataata atttaggtaa ggggcgttca ggcggaaggc ctaaaccaaa aagttttgat    720

gaagttgaaa aagagtttga taatttgatt gaagatgaag ccgagacgtc ggtcgcggat    780
```

-continued tctgattcgt attaa 795

<210> SEQ ID NO 21
<211> LENGTH: 1336
<212> TYPE: DNA
<213> ORGANISM: Escherichia coli

<400> SEQUENCE: 21
tggatttgcc cctatatttc cagacatctg ttatcactta acccattaca agcccgctgc 60
cgcagatatt cccgtggcga gcgataaccc agcgcactat gcggatgcca ttcgttataa 120
tgctcgaacg cctctgcaag gttctttgct gccgttaacc cgtctggttt gggcatgata 180
ctgatgtagt cacgctttat cgttttcacg aagctctctg ctattccgtt actctccgga 240
ctccgcaccg ccgtgttctt cggttcaagt cccaacatcc gggcgaactg gcgtgtttca 300
ttagcccggt agcatgaacc attatccgtc agccactcca ctggagacga cggaagatcg 360
ttgccgaagc ggcgttccac cgctcccagc atgacgtcct gtactgtttc actgttgaag 420
ccgccggtag tgaccgccca gtgcagtgcc tcacgatcac agcagtccag cgcgaacgtg 480
acacgcagtc tctctccgtt atcacagcag aactcgaacc cgtcagagca ccatcgctga 540
ttgctttctt tcacggccac tctgcctgta tgtgcccgtt tcgatggcgg tacagcaggt 600
tttcgctcaa gcaacagcgc attctggcgc atgatccggt aaacacgttt ggcattgatc 660
gcaggcatac catcaagttc tgcctgtctg cgaagcagcg cccatacccg acgataacca 720
tacgttggca gctctccgat aacatggtgt atacggagaa gcacatccgt atcatcagtg 780
tgacgactgc ggcggccatc catccagtca tcggttcgtc tgagaatgac gtgcaactgc 840
gcacgcgaca cccggagaca acggctgact aagcttactc cccatccccg ggcaataagg 900
gcgcgtgcgc tatccacttt tttgcccgtc catattcaac ggcttctttg aggagttcat 960
tttccatcgt tttcttgccg agcaggcgct ggagttcttt aatctgcttc atggcggcag 1020
caagttcaga ggcaggaaca acctgttctc cggcggcgac agcagtaaga cttccttcct 1080
ggtattgctt acgccagaga aataactggc tggctgctac accatgttgc cgggcaacga 1140
gggagaccgt catccccggt tcaaagctct gctgaacaat tgcgatcttt tcctgtgtgg 1200
tacgccgtct gcgtttctcc ggccctaaga catcaatcat ctgttctcca atgactagtc 1260
taaaaactag tattaagact atcacttatt taagtgatat tggttgtctg gagattcagg 1320
gggccagtct agtgag 1336

<210> SEQ ID NO 22
<211> LENGTH: 1258
<212> TYPE: DNA
<213> ORGANISM: Escherichia coli

<400> SEQUENCE: 22
tggatttgcc cctatatttc cagacatctg ttatcactta acccattaca agcccgctgc 60
cgcagatatt cccgtggcga gcgataaccc agcgcactat gcggatgcca ttcgttataa 120
tgctcgaacg cctctgcaag gttctttgct gccgttaacc cgtctggttt gggcatgata 180
ctgatgtagt cacgctttat cgttttcacg aagctctctg ctattccgtt actctccgga 240
ctccgcaccg ccgtgttctt cggttcaagt cccaacatcc gggcgaactg gcgtgtttca 300
ttagcccggt agcatgaacc attatccgtc agccactcca ctggagacga cggaagatcg 360
ttgccgaagc ggcgttccac cgctcccagc atgacgtcct gtactgtttc actgttgaag 420
ccgccggtag tgaccgccca gtgcagtgcc tcacgatcac agcagtccag cgcgaacgtg 480

-continued

```
acacgcagtc tctctccgtt atcacagcag aactcgaacc cgtcagagca ccatcgctga    540

ttgctttctt tcacggccac tctgcctgta tgtgcccgtt tcgatggcgg tacagcaggt    600

tttcgctcaa gcaacagcgc attctggcgc atgatccggt aaacacgttt ggcattgatc    660

gcaggcatac catcaagttc tgcctgtctg cgaagcagcg cccatacccg acgataacca    720

tacgttggca gctctccgat aacatggtgt atacggagaa gcacatccgt atcatcagtg    780

tgacgactgc ggcggccatc catccagtca tcggttcgtc tgagaatgac gtgcaactgc    840

gcacgcgaca cccggagaca acggctgact aagcttactc cccatccccg ggcaataagg    900

gcgcgtgcgc tatccacttt tttgcccgtc catattcaac ggcttctttg aggagttcat    960

tttccatcgt tttcttgccg agcaggcgct ggagttcttt aatctgcttc atggcggcag   1020

caagttcaga ggcaggaaca acctgttctc cggcggcgac agcagtaaga cttccttcct   1080

ggtattgctt acgccagaga aataactggc tggctgctac accatgttgc cgggcaacga   1140

gggagaccgt catccccggt tcaaagctct gctgaacaat tgcgatcttt tcctgtgtgg   1200

tacgccgtct gcgtttctcc ggccctaaga catcaatcat ctgttctcca atggtgag     1258
```

<210> SEQ ID NO 23
<211> LENGTH: 1333
<212> TYPE: DNA
<213> ORGANISM: Escherichia coli

<400> SEQUENCE: 23

```
taacggttca ggcacagcac atcaaagaga tcgctgatgg tatcggtgtg agcgtcgcag     60

aacattacat tgacgcaggt gatcggacgc gtcgggtcga gtttacgcgt tgcttccgcc    120

agtggcgcga aatattcccg tgcaccttgc ggacgggtat ccggttcgtt ggcaatactc    180

cacatcacca cgcttgggtg gtttttgtca cgcgctatca gctctttaat cgcctgtaag    240

tgcgcttgct gagtttcccc gttgactgcc tcttcgctgt acagttcttt cggcttgttg    300

cccgcttcga aaccaatgcc taaagagagg ttaaagccga cagcagcagt ttcatcaatc    360

accacgatgc catgttcatc tgcccagtcg agcatctctt cagcgtaagg gtaatgcgag    420

gtacggtagg agttggcccc aatccagtcc attaatgcgt ggtcgtgcac catcagcacg    480

ttatcgaatc ctttgccacg caagtccgca tcttcatgac gaccaaagcc agtaaagtag    540

aacggtttgt ggttaatcag gaactgttcg cccttcactg ccactgaccg gatgccgacg    600

cgaagcgggt agatatcaca ctctgtctgg cttttggctg tgacgcacag ttcatagaga    660

taaccttcac ccggttgcca gaggtgcgga ttcaccactt gcaaagtccc gctagtgcct    720

tgtccagttg caaccacctg ttgatccgca tcacgcagtt caacgctgac atcaccattg    780

gccaccacct gccagtcaac agacgcgtgg ttacagtctt gcgcgacatg cgtcaccacg    840

gtgatatcgt ccacccaggt gttcggcgtg gtgtagagca ttacgctgcg atggattccg    900

gcatagttaa agaaatcatg gaagtaagac tgctttttct tgccgttttc gtcggtaatc    960

accattcccg gcgggatagt ctgccagttc agttcgttgt tcacacaaac ggtgatacgt   1020

acacttttcc cggcaataac atacggcgtg acatcggctt caaatggcgt atagccgccc   1080

tgatgctcca tcacttcctg attattgacc cacactttgc cgtaatgagt gaccgcatcg   1140

aaacgcagca cgatacgctg gcctgcccaa cctttcggta taaagacttc gcgctgatac   1200

cagacgttgc ccgcataatt acgaatatct gcatcggcga actgatcgtt aaaactgcct   1260

ggcacagcaa ttgcccggct ttcttgtaac gcgctttccc accaacgctg atcaattcca   1320

cagttttcgc gat                                                      1333
```

-continued

<210> SEQ ID NO 24
<211> LENGTH: 1333
<212> TYPE: DNA
<213> ORGANISM: Escherichia coli

<400> SEQUENCE: 24
taacggttca ggcacagcac atcaaagaga tcgctgatgg tatcggtgtg agcgtcgcag 60
aacattacat tgacgcaggt gatcggacgc gtcgggtcga gtttacgcgt tgcttccgcc 120
agtggcgcga aatattcccg tgcaccttgc ggacgggtat ccggttcgtt ggcaatactc 180
cacatcacca cgcttgggtg gtttttgtca cgcgctatca gctctttaat cgcctgtaag 240
tgcgcttgct gagtttcccc gttgactgcc tcttcgctgt acagttcttt cggcttgttg 300
cccgcttcga aaccaatgcc taaagagagg ttaaagccga cagcagcagt ttcatcaatc 360
accacgatgc catgttcatc tgcccagtcg agcatctctt cagcgtaagg gtaatgcgag 420
gtacggtagg agttggcccc aatccagtcc attaatgcgt ggtcgtgcac catcagcacg 480
ttatcgaatc ctttgccacg caagtccgca tcttcatgac gaccaaagcc agtaaagtag 540
aacggtttgt ggttaatcag gaactgttcg cccttcactg ccactgaccg gatgccgacg 600
cgaagcgggt agatatcaca ctctgtctgg cttttggctg tgacgcacag ttcatagaga 660
taaccttcac ccggttgcca gaggtgcgga ttcaccactt gcaaagtccc gctagtgcct 720
tgtccagttg caaccacctg ttgatccgca tcacgcagtt caacgctgac atcaccattg 780
gccaccacct gccagtcaac agacgcgtgg ttacagtctt gcgcgacatg cgtcaccacg 840
gtgatatcgt ccacccaggt gttcggcgtg gtgtagagca ttacgctgcg atggattccg 900
gcatagttaa agaaatcatg gaagtaagac tgctttttct tgccgttttc gtcggtaatc 960
accattcccg gcgggatagt ctgccagttc agttcgttgt tcacacaaac ggtgatacgt 1020
acacttttcc cggcaataac atacggcgtg acatcggctt caaatggcgt atagccgccc 1080
tgatgctcca tcacttcctg attattgacc cacactttgc cgtaatgagt gaccgcatcg 1140
aaacgcagca cgatacgctg gcctgcccaa cctttcggta taaagacttc gcgctgatac 1200
cagacgttgc ccgcataatt acgaatatct gcatcggcga actgatcgtt aaaactgcct 1260
ggcacagcaa ttgcccggct ttcttgtaac gcgctttccc accaacgctg atcaattcca 1320
cagttttcgc gat 1333

<210> SEQ ID NO 25
<211> LENGTH: 1338
<212> TYPE: DNA
<213> ORGANISM: Escherichia coli

<400> SEQUENCE: 25
taacggttca ggcacagcac atcaaagaga tcgctgatgg tatcggtgtg agcgtcgcag 60
aacattacat tgacgcaggt gatcggacgc gtcgggtcga gtttacgcgt tgcttccgcc 120
agtggcgcga aatattcccg tgcaccttgc ggacgggtat ccggttcgtt ggcaatactc 180
cacatcacca cgcttgggtg gtttttgtca cgcgctatca gctctttaat cgcctgtaag 240
tgcgcttgct gagtttcccc gttgactgcc tcttcgctgt acagttcttt cggcttgttg 300
cccgcttcga aaccaatgcc taaagagagg ttaaagccga cagcagcagt ttcatcaatc 360
accacgatgc catgttcatc tgcccagtcg agcatctctt cagcgtaagg gtaatgcgag 420
gtacggtagg agttggcccc aatccagtcc attaatgcgt ggtcgtgcac catcagcacg 480
ttatcgaatc ctttgccacg caagtccgca tcttcatgac gaccaaagcc agtaaagtag 540

```
aacggtttgt ggttaatcag gaactgttcg cccttcactg ccactgaccg gatgccgacg     600

cgaagcgggt agatatcaca ctctgtctgg cttttggctg tgacgcacag ttcatagaga     660

taaccttcac ccggttgcca gaggtgcgga ttcaccactt gcaaagtccc gctagtgcct     720

tgtccagttg caaccacctg ttgatccgca tcacgcagtt caacgctgac atcaccattg     780

gccaccacct gccagtcaac agacgcgtgg ttacagtctt gcgcgacatg cgtcaccacg     840

gtgatatcgt ccacccaggt gttcggcgtg gtgtagagca ttacgctgcg atggattccg     900

gcatagttaa agaaatcatg gaagtaagac tgctttttct tgccgttttc gtcggtaatc     960

accattcccg gcgggatagt ctgccagttc agttcgttgt tcacacaaac ggtgatacgt    1020

acacttttcc cggcaataac atacggcgtg acatcggctt caaatggcgt atagccgccc    1080

tgatgctcca tcacttcctg attattgacc cacactttgc cgtaatgagt gaccgcatcg    1140

aaacgcagca cgatacgctg gcctgcccaa cctttcggta taaagacttc gcgctgatac    1200

cagacgttgc ccgcataatt acgaatatct gcatcggcga actgatcgtt aaaactgcct    1260

ggcacagcaa ttgcccggct ttcttgtaac gcgctttccc accaacgctg atcaattcca    1320

cagttttcgc gatgtgag                                                  1338
```

```
<210> SEQ ID NO 26
<211> LENGTH: 1333
<212> TYPE: DNA
<213> ORGANISM: Escherichia coli

<400> SEQUENCE: 26

taacggttca ggcacagcac atcaaagaga tcgctgatgg tatcggtgtg agcgtcgcag      60

aacattacat tgacgcaggt gatcggacgc gtcgggtcga gtttacgcgt tgcttccgcc     120

agtggcgcga aatattcccg tgcaccttgc ggacgggtat ccggttcgtt ggcaatactc     180

cacatcacca cgcttgggtg gtttttgtca cgcgctatca gctctttaat cgcctgtaag     240

tgcgcttgct gagtttcccc gttgactgcc tcttcgctgt acagttcttt cggcttgttg     300

cccgcttcga aaccaatgcc taaagagagg ttaaagccga cagcagcagt ttcatcaatc     360

accacgatgc catgttcatc tgcccagtcg agcatctctt cagcgtaagg gtaatgcgag     420

gtacggtagg agttggcccc aatccagtcc attaatgcgt ggtcgtgcac catcagcacg     480

ttatcgaatc ctttgccacg caagtccgca tcttcatgac gaccaaagcc agtaaagtag     540

aacggtttgt ggttaatcag gaactgttcg cccttcactg ccactgaccg gatgccgacg     600

cgaagcgggt agatatcaca ctctgtctgg cttttggctg tgacgcacag ttcatagaga     660

taaccttcac ccggttgcca gaggtgcgga ttcaccactt gcaaagtccc gctagtgcct     720

tgtccagttg caaccacctg ttgatccgca tcacgcagtt caacgctgac atcaccattg     780

gccaccacct gccagtcaac agacgcgtgg ttacagtctt gcgcgacatg cgtcaccacg     840

gtgatatcgt ccacccaggt gttcggcgtg gtgtagagca ttacgctgcg atggattccg     900

gcatagttaa agaaatcatg gaagtaagac tgctttttct tgccgttttc gtcggtaatc     960

accattcccg gcgggatagt ctgccagttc agttcgttgt tcacacaaac ggtgatacgt    1020

acacttttcc cggcaataac atacggcgtg acatcggctt caaatggcgt atagccgccc    1080

tgatgctcca tcacttcctg attattgacc cacactttgc cgtaatgagt gaccgcatcg    1140

aaacgcagca cgatacgctg gcctgcccaa cctttcggta taaagacttc gcgctgatac    1200

cagacgttgc ccgcataatt acgaatatct gcatcggcga actgatcgtt aaaactgcct    1260

ggcacagcaa ttgcccggct ttcttgtaac gcgctttccc accaacgctg atcaattcca    1320
```

cagttttcgc gat 1333

<210> SEQ ID NO 27
<211> LENGTH: 1333
<212> TYPE: DNA
<213> ORGANISM: Escherichia coli

<400> SEQUENCE: 27
taacggttca ggcacagcac atcaaagaga tcgctgatgg tatcggtgtg agcgtcgcag 60
aacattacat tgacgcaggt gatcggacgc gtcgggtcga gtttacgcgt tgcttccgcc 120
agtggcgcga aatattcccg tgcaccttgc ggacgggtat ccggttcgtt ggcaatactc 180
cacatcacca cgcttgggtg gtttttgtca cgcgctatca gctctttaat cgcctgtaag 240
tgcgcttgct gagtttcccc gttgactgcc tcttcgctgt acagttcttt cggcttgttg 300
cccgcttcga aaccaatgcc taaagagagg ttaaagccga cagcagcagt ttcatcaatc 360
accacgatgc catgttcatc tgcccagtcg agcatctctt cagcgtaagg gtaatgcgag 420
gtacggtagg agttggcccc aatccagtcc attaatgcgt ggtcgtgcac catcagcacg 480
ttatcgaatc ctttgccacg caagtccgca tcttcatgac gaccaaagcc agtaaagtag 540
aacggtttgt ggttaatcag gaactgttcg cccttcactg ccactgaccg gatgccgacg 600
cgaagcgggt agatatcaca ctctgtctgg cttttggctg tgacgcacag ttcatagaga 660
taaccttcac ccggttgcca gaggtgcgga ttcaccactt gcaaagtccc gctagtgcct 720
tgtccagttg caaccacctg ttgatccgca tcacgcagtt caacgctgac atcaccattg 780
gccaccacct gccagtcaac agacgcgtgg ttacagtctt gcgcgacatg cgtcaccacg 840
gtgatatcgt ccacccaggt gttcggcgtg gtgtagagca ttacgctgcg atggattccg 900
gcatagttaa agaaatcatg gaagtaagac tgctttttct tgccgttttc gtcggtaatc 960
accattcccg gcgggatagt ctgccagttc agttcgttgt tcacacaaac ggtgatacgt 1020
acacttttcc cggcaataac atacggcgtg acatcggctt caaatggcgt atagccgccc 1080
tgatgctcca tcacttcctg attattgacc cacactttgc cgtaatgagt gaccgcatcg 1140
aaacgcagca cgatacgctg gcctgcccaa cctttcggta taaagacttc gcgctgatac 1200
cagacgttgc ccgcataatt acgaatatct gcatcggcga actgatcgtt aaaactgcct 1260
ggcacagcaa ttgcccggct ttcttgtaac gcgctttccc accaacgctg atcaattcca 1320
cagttttcgc gat 1333

<210> SEQ ID NO 28
<211> LENGTH: 1333
<212> TYPE: DNA
<213> ORGANISM: Escherichia coli

<400> SEQUENCE: 28
taacggttca ggcacagcac atcaaagaga tcgctgatgg tatcggtgtg agcgtcgcag 60
aacattacat tgacgcaggt gatcggacgc gtcgggtcga gtttacgcgt tgcttccgcc 120
agtggcgcga aatattcccg tgcaccttgc ggacgggtat ccggttcgtt ggcaatactc 180
cacatcacca cgcttgggtg gtttttgtca cgcgctatca gctctttaat cgcctgtaag 240
tgcgcttgct gagtttcccc gttgactgcc tcttcgctgt acagttcttt cggcttgttg 300
cccgcttcga aaccaatgcc taaagagagg ttaaagccga cagcagcagt ttcatcaatc 360
accacgatgc catgttcatc tgcccagtcg agcatctctt cagcgtaagg gtaatgcgag 420
gtacggtagg agttggcccc aatccagtcc attaatgcgt ggtcgtgcac catcagcacg 480
ttatcgaatc ctttgccacg caagtccgca tcttcatgac gaccaaagcc agtaaagtag 540
aacggtttgt ggttaatcag gaactgttcg cccttcactg ccactgaccg gatgccgacg 600
cgaagcgggt agatatcaca ctctgtctgg cttttggctg tgacgcacag ttcatagaga 660
taaccttcac ccggttgcca gaggtgcgga ttcaccactt gcaaagtccc gctagtgcct 720
tgtccagttg caaccacctg ttgatccgca tcacgcagtt caacgctgac atcaccattg 780
gccaccacct gccagtcaac agacgcgtgg ttacagtctt gcgcgacatg cgtcaccacg 840
gtgatatcgt ccacccaggt gttcggcgtg gtgtagagca ttacgctgcg atggattccg 900
gcatagttaa agaaatcatg gaagtaagac tgctttttct tgccgttttc gtcggtaatc 960
accattcccg gcgggatagt ctgccagttc agttcgttgt tcacacaaac ggtgatacgt 1020
acacttttcc cggcaataac atacggcgtg acatcggctt caaatggcgt atagccgccc 1080
tgatgctcca tcacttcctg attattgacc cacactttgc cgtaatgagt gaccgcatcg 1140
aaacgcagca cgatacgctg gcctgcccaa cctttcggta taaagacttc gcgctgatac 1200
cagacgttgc ccgcataatt acgaatatct gcatcggcga actgatcgtt aaaactgcct 1260
ggcacagcaa ttgcccggct ttcttgtaac gcgctttccc accaacgctg atcaattcca 1320
cagttttcgc gat 1333

<210> SEQ ID NO 29
<211> LENGTH: 600
<212> TYPE: DNA
<213> ORGANISM: Escherichia coli

<400> SEQUENCE: 29
ccacctgttg atccgcatca cgcagttcaa cgctgacatc accattggcc accacctgcc 60
agtcaacaga cgcgtggtta cagtcttgcg cgacatgcgt caccacggtg atatcgtcca 120
cccaggtgtt cggcgtggtg tagagcatta cgctgcgatg gattccggca tagttaaaga 180
aatcatggaa gtaagactgc tttttcttgc cgttttcgtc ggtaatcacc attcccggcg 240
ggatagtctg ccagttcagt tcgttgttca cacaaacggt gatacgtaca cttttcccgg 300
caataacata cggcgtgaca tcggcttcaa atggcgtata gccgccctga tgctccatca 360
cttcctgatt attgacccac actttgccgt aatgagtgac cgcatcgaaa cgcagcacga 420
tacgctggcc tgcccaacct ttcggtataa agacttcgcg ctgataccag acgttgcccg 480
cataattacg aatatctgca tcggcgaact gatcgttaaa actgcctggc acagcaattg 540
cccggctttc ttgtaacgcg ctttcccacc aacgctgatc aattccacag ttttcgcgat 600

<210> SEQ ID NO 30
<211> LENGTH: 300
<212> TYPE: DNA
<213> ORGANISM: Escherichia coli

<400> SEQUENCE: 30
caataacata cggcgtgaca tcggcttcaa atggcgtata gccgccctga tgctccatca 60
cttcctgatt attgacccac actttgccgt aatgagtgac cgcatcgaaa cgcagcacga 120
tacgctggcc tgcccaacct ttcggtataa agacttcgcg ctgataccag acgttgcccg 180
cataattacg aatatctgca tcggcgaact gatcgttaaa actgcctggc acagcaattg 240
cccggctttc ttgtaacgcg ctttcccacc aacgctgatc aattccacag ttttcgcgat 300

<210> SEQ ID NO 31
<211> LENGTH: 100
<212> TYPE: DNA

<213> ORGANISM: Escherichia coli

<400> SEQUENCE: 31
tcggcgaact gatcgttaaa actgcctggc acagcaattg cccggctttc ttgtaacgcg 60
ctttcccacc aacgctgatc aattccacag ttttcgcgat 100

<210> SEQ ID NO 32
<211> LENGTH: 1604
<212> TYPE: DNA
<213> ORGANISM: Escherichia coli

<400> SEQUENCE: 32
tcattgtttg cctccctgct gcggtttttc accgaagttc atgccagtcc agcgtttttg 60
cagcagaaaa gccgccgact tcggtttgcg gtcgcgagtg aagatccctt tcttgttacc 120
gccaacgcgc aatatgcctt gcgaggtcgc aaaatcggcg aaattccata cctgttcacc 180
gacgacggcg ctgacgcgat caaagacgcg gtgatacata tccagccatg cacactgata 240
ctcttcactc cacatgtcgg tgtacattga gtgcagcccg gctaacgtat ccacgccgta 300
ttcggtgatg ataatcggct gatgcagttt ctcctgccag gccagaagtt ctttttccag 360
taccttctct gccgtttcca aatcgccgct ttggacatac catccgtaat aacggttcag 420
gcacagcaca tcaaagagat cgctgatggt atcggtgtga gcgtcgcaga acattacatt 480
gacgcaggtg atcggacgcg tcgggtcgag tttacgcgtt gcttccgcca gtggcgcgaa 540
atattcccgt gcaccttgcg gacgggtatc cggttcgttg gcaatactcc acatcaccac 600
gcttgggtgg tttttgtcac gcgctatcag ctctttaatc gcctgtaagt gcgcttgctg 660
agtttccccg ttgactgcct cttcgctgta cagttctttc ggcttgttgc ccgcttcgaa 720
accaatgcct aaagagaggt taaagccgac agcagcagtt tcatcaatca ccacgatgcc 780
atgttcatct gcccagtcga gcatctcttc agcgtaaggg taatgcgagg tacggtagga 840
gttggcccca atccagtcca ttaatgcgtg gtcgtgcacc atcagcacgt tatcgaatcc 900
tttgccacgc aagtccgcat cttcatgacg accaaagcca gtaaagtaga acggtttgtg 960
gttaatcagg aactgttcgc ccttcactgc cactgaccgg atgccgacgc gaagcgggta 1020
gatatcacac tctgtctggc ttttggctgt gacgcacagt tcatagagat aaccttcacc 1080
cggttgccag aggtgcggat tcaccacttg caaagtcccg ctagtgcctt gtccagttgc 1140
aaccacctgt tgatccgcat cacgcagttc aacgctgaca tcaccattgg ccaccacctg 1200
ccagtcaaca gacgcgtggt tacagtcttg cgcgacatgc gtcaccacgg tgatatcgtc 1260
cacccaggtg ttcggcgtgg tgtagagcat tacgctgcga tggattccgg catagttaaa 1320
gaaatcatgg aagtaagact gctttttctt gccgttttcg tcggtaatca ccattcccgg 1380
cgggatagtc tgccagttca gttcgttgtt cacacaaacg gtgatacgta cacttttccc 1440
ggcaataaca tacggcgtga catcggcttc aaatggcgta tagccgccct gatgctccat 1500
cacttcctga ttattgaccc acactttgcc gtaatgagtg accgcatcga aacgcagcac 1560
gatacgctgg cctgcccaac cccccaaaga tgtcctgcat tgta 1604

<210> SEQ ID NO 33
<211> LENGTH: 480
<212> TYPE: DNA
<213> ORGANISM: Escherichia coli

<400> SEQUENCE: 33
ccgtggacaa caaattcaac aaagaacaac aaaacgcgtt ctatgagatc ttacatttac 60

-continued

```
ctaacttaaa cgaagaacaa cgaaacgcct tcatccaaag tttaaaagat gacccaagcc    120

aaagcgctaa ccttttagca gaagctaaaa agctaaatga tgctcaggcg ccgaaagtag    180

acaacaaatt caacaaagaa caacaaaacg cgttctatga gatcttacat ttacctaact    240

taaacgaaga acaacgaaac gccttcatcc aaagtttaaa agatgaccca agccaaagcg    300

ctaacctttt agcagaagct aaaaagctaa atggtgctca ggcgccgaaa gtagacgcga    360

attccgcggg gaagtcaacc tgaaggccta aaccaaaaag ttttgatgaa gttgaaaaag    420

agtttgataa tttgattgaa gatgaagccg agacgtcggt cgcggattct gattcgtatg    480
```

<210> SEQ ID NO 34
<211> LENGTH: 1333
<212> TYPE: DNA
<213> ORGANISM: Escherichia coli

<400> SEQUENCE: 34

```
taacggttca ggcacagcac atcaaagaga tcgctgatgg tatcggtgtg agcgtcgcag     60

aacattacat tgacgcaggt gatcggacgc gtcgggtcga gtttacgcgt tgcttccgcc    120

agtggcgcga aatattcccg tgcaccttgc ggacgggtat ccggttcgtt ggcaatactc    180

cacatcacca cgcttgggtg gtttttgtca cgcgctatca gctctttaat cgcctgtaag    240

tgcgcttgct gagtttcccc gttgactgcc tcttcgctgt acagttcttt cggcttgttg    300

cccgcttcga aaccaatgcc taaagagagg ttaaagccga cagcagcagt ttcatcaatc    360

accacgatgc catgttcatc tgcccagtcg agcatctctt cagcgtaagg gtaatgcgag    420

gtacggtagg agttggcccc aatccagtcc attaatgcgt ggtcgtgcac catcagcacg    480

ttatcgaatc ctttgccacg caagtccgca tcttcatgac gaccaaagcc agtaaagtag    540

aacggtttgt ggttaatcag gaactgttcg cccttcactg ccactgaccg gatgccgacg    600

cgaagcgggt agatatcaca ctctgtctgg cttttggctg tgacgcacag ttcatagaga    660

taaccttcac ccggttgcca gaggtgcgga ttcaccactt gcaaagtccc gctagtgcct    720

tgtccagttg caaccacctg ttgatccgca tcacgcagtt caacgctgac atcaccattg    780

gccaccacct gccagtcaac agacgcgtgg ttacagtctt gcgcgacatg cgtcaccacg    840

gtgatatcgt ccacccaggt gttcggcgtg gtgtagagca ttacgctgcg atggattccg    900

gcatagttaa agaaatcatg gaagtaagac tgctttttct tgccgttttc gtcggtaatc    960

accattcccg gcgggatagt ctgccagttc agttcgttgt tcacacaaac ggtgatacgt   1020

acacttttcc cggcaataac atacggcgtg acatcggctt caaatggcgt atagccgccc   1080

tgatgctcca tcacttcctg attattgacc cacactttgc cgtaatgagt gaccgcatcg   1140

aaacgcagca cgatacgctg gcctgcccaa cctttcggta taaagacttc gcgctgatac   1200

cagacgttgc ccgcataatt acgaatatct gcatcggcga actgatcgtt aaaactgcct   1260

ggcacagcaa ttgcccggct ttcttgtaac gcgctttccc accaacgctg atcaattcca   1320

cagttttcgc gat                                                      1333
```

<210> SEQ ID NO 35
<211> LENGTH: 6384
<212> TYPE: DNA
<213> ORGANISM: Tomato mosaic virus

<400> SEQUENCE: 35

```
gtatttttac aacaattacc aacaacaaca acaaacaaca acaacattac attttacatt     60

ctacaactac aatggcatac acacaaacag ccacatcgtc cgctttgctt gagaccgtcc    120
```

-continued

```
gaggtaacaa taccttggtc aacgatcttg caaagcggcg tctatatgac acagcggtcg    180
atgaatttaa tgctagggac cgcaggccta aagtcaattt ttccaaagta gtaagcgaag    240
aacagacgct tattgcaacc aaagcctacc cagaattcca aattacattc tacaacacgc    300
agaatgctgt gcattccctt gcaggcggtc tccgatcatt agaattggaa tatctgatga    360
tgcaaattcc ctacggatca ttgacatatg atatcggagg taattttgca tctcatctgt    420
tcaaagggcg agcatacgtt cactgctgta tgccgaatct ggatgtccgc gacataatgc    480
ggcacgaggg ccaaaaggac agtattgaac tatacctttc taggctcgag aggggcaaca    540
aacatgtccc aaacttccaa aaggaagctt tcgacagata cgctgaaatg ccaaacgaag    600
tagtctgtca cgatactttc caaacgtgta ggcattctca agaatgttac acgggaagag    660
tgtatgctat tgctttgcat agtatatacg atatacctgc cgacgagttc ggcgcggcac    720
tgctgagaaa gaatgtacat gtatgttatg ccgctttcca cttttccgag aatttacttc    780
tcgaagattc acacgtcaac ctcgacgaga tcaatgcatg tttccaaaga gatggagaca    840
ggttgacttt ttcctttgca tctgagagta ctcttaatta tagtcatagt tattctaata    900
ttcttaagta tgtttgcaaa acttacttcc cagcctctaa tagagaggtt tacatgaagg    960
agtttttagt aactagagtt aatacctggt tttgtaaatt ttctagaata gatactttct   1020
tattgtacaa aggtgtagcg cataagggtg tagatagtga gcagttttac aaggctatgg   1080
aagacgcatg gcactacaaa aagactcttg cgatgtgcaa cagtgaaaga atcttgttag   1140
aggattcttc atcagttaat tactggtttc caaaaatgag ggatatggtg atagttccac   1200
tatttgacat atctctcgag actagtaaaa gaacacgcaa agaggtctta gtttcaaagg   1260
actttgttta tacagtgtta aatcacattc gtacgtacca ggccaaagcg cttacttact   1320
ccaacgtgtt atctttcgtc gaatcaattc gttcgagagt gatcattaac ggggttactg   1380
ctaggtctga gtgggatgtc gataaatcat tattacagtc cttgtcgatg acgttcttcc   1440
tacacaccaa gcttgccgtt ctgaaagacg atcttttgat tagcaagttt gcacttggac   1500
caaaaactgt ctcacaacat gtgtgggatg agatttccct agctttcggc aatgctttcc   1560
catcgatcaa ggaaagattg ataaaccgga aactgatcaa aattacggag aatgcgttag   1620
agatcagggt gcccgatctt tatgtcactt tccatgatag gttagtttct gagtacaaaa   1680
tgtcagtgga catgccggtg ctagacatta ggaaaaagat ggaagaaact gaggaaatgt   1740
acaatgcact gtccgaactg tctgtactta aaaattcaga caagttcgat gttgacgttt   1800
tttcccagat gtgccaatct ttagaagtcg atccaatgac tgcagcaaag gtaatagtag   1860
cagttatgag caacgagagt ggtcttactc tcacgtttga acagcccacc gaagctaatg   1920
ttgcgctagc attgcaagat tctgaaaagg cttctgatgg ggcgttggta gttacctcaa   1980
gagatgttga ggaaccgtcc ataaagggtt cgatggcccg tggtgagtta caattggccg   2040
gattatctgg cgacgttcct gaatcttcat acactaggag cgaggagatt gagtctctcg   2100
agcagtttca tatggcaaca gctagttcgt taattcataa gcagatgtgt tcgatcgtgt   2160
acacgggccc tcttaaagtt caacaaatga aaaactttat agacagcctg gtagcctcgc   2220
tctctgctgc ggtgtcgaat ctagtgaaga tcctaaaaga tacagccgcg attgaccttg   2280
aaactcgtca aaagttcgga gttctggatg ttgcttcgaa aaggtggcta gttaaaccat   2340
ccgcaaagaa ccatgcatgg ggggttgttg agactcatgc gaggaaatat cacgtcgcat   2400
tactggagca cgatgaattt ggcattatta cgtgcgataa ctggcgacgg gtggctgtga   2460
gttctgagtc ggtagtatat tctgatatgg ctaaactcag gactctgaga agattgctca   2520
```

-continued

```
aagatggaga accacacgtt agttcagcaa aggtggtttt ggtggatggc gttccagggt   2580
gcgggaagac aaaggaaatt ctttcgagag ttaatttcga agaagatcta attcttgtcc   2640
ctggtcgtca agctgccgag atgatcagaa gaagagctaa tgcgtcgggc ataatagtgg   2700
ctacaaagga taatgtgcgc accgtcgatt catttttgat gaattacggg aaaggggcac   2760
gctgtcagtt caaaagattg ttcatagacg aaggtttgat gctgcatact ggttgtgtga   2820
atttttggt tgaaatgtct ctgtgcgata ttgcatatgt ttatggagac acccaacaga   2880
ttccgtacat caacagagta actggtttcc cgtaccctgc acactttgca aaattggagg   2940
tcgacgaagt cgaaacaaga agaactactc ttcgttgtcc ggctgatgtc acacacttcc   3000
taaatcaaag gtatgaagga cacgtaatgt gcacgtcttc tgaaaagaaa tcagtttccc   3060
aggaaatggt tagtggggct gcgtctatca atcctgtgtc caagccgctt aagggaaaaa   3120
ttttgacttt cacacagtct gacaaggagg cccttctctc aaggggctac gcagatgtcc   3180
atactgtaca tgaggtacaa ggtgagactt atgcagacgt atcgttagtt cgactaacac   3240
ctacgcctgt atctatcatc gcaagagaca gtccgcatgt tctggtctcg ttgtcaagac   3300
acacaaaatc cctaaagtac tacaccgttg tgatggatcc tttagttagt atcattagag   3360
atttagaacg ggttagtagt tacttattag acatgtacaa agtagatgca ggtactcaat   3420
agcaattaca ggtcgactct gtgtttaaaa atttcaatct tttgtagca gctccaaaga   3480
ctggagatat atctgatatg caattttact atgataagtg tcttcctggg aacagcacgt   3540
tgttgaacaa ctacgacgct gttaccatga aattgactga catttctctg aatgtcaaag   3600
attgcatatt agatatgtct aagtctgtag ctgctccgaa agatgtcaaa ccaactttaa   3660
taccgatggt acgaacggcg gcagaaatgc ctcgccagac tggactgttg gaaaatctag   3720
ttgcgatgat taaaagaaat tttaattcac cagagttgtc cggagtagtt gatattgaaa   3780
atactgcatc tttagtggta gataagtttt ttgatagtta tttacttaag gaaaaaagaa   3840
aaccaaacaa aaatttttca ctgtttagta gagagtctct caataggtgg atagcaaagc   3900
aagaacaagt cacaattggt cagttggccg attttgattt tgtggatctt ccagccgttg   3960
atcagtacag gcatatgatt aaagcgcaac cgaagcagaa actggatctg tcaattcaga   4020
cagaatatcc agcgttgcaa acgattgtgt atcattcaaa gaaaatcaac gcaatatttg   4080
gtcctctttt cagtgagctt acaaggcaat tacttgacag tattgactca agcagattct   4140
tgttctttac gagaaagaca ccggctcaga tcgaagattt cttcggagat ctagacagtc   4200
atgtcccaat ggacgtactt gagttggatg tttcgaagta tgataagtct caaaacgagt   4260
ttcattgtgc tgttgagtac gaaatctgga ggagactggg tctggaggat ttcttggcag   4320
aagtgtggaa acaagggcat agaaaaacca ctctgaaaga ttacactgct ggtataaaaa   4380
cgtgtttatg gtaccagaga aagagtggtg atgttacaac ttttatcggt aataccgtca   4440
tcattgcttc gtgtctagca tcaatgctcc cgatggaaaa attgataaaa ggagccttct   4500
gcggagatga cagtttgttg tactttccta agggttgtga gtatcccgat atacaacaag   4560
ctgctaatct aatgtggaat tttgaggcca aactgttcaa gaagcaatat gggtacttct   4620
gcgggaggta cgtgattcat cacgatagag gttgcatagt atactacgac cctttgaagc   4680
tgatttcgaa acttggtgct aaacacatca aggattggga tcatttggag gagttcagaa   4740
gatccctctg tgatgttgct gagtcgttga acaattgcgc gtattacaca caattggacg   4800
acgctgttgg ggaggttcat aaaaccgccc cacctggttc gtttgtttat aagagtttag   4860
ttaagtattt gtcagataaa gttttgttta gaagtttatt tcttgatggc tctagttgtt   4920
```

```
aaaggtaagg taaatattaa tgagtttatc gatctgtcaa agtctgagaa acttctcccg   4980

tcgatgttca cgcctgtaaa gagtgttatg gtttcaaagg ttgataagat tatggtccat   5040

gaaaatgaat cattgtctga agtaaatctc ttaaaaggtg taaaacttat agaaggtggg   5100

tatgtttgct tagtcggtct tgttgtgtcc ggtgagtgga atttaccaga taattgccgt   5160

ggtggtgtga gtgtctgcat ggttgacaag agaatggaaa gagcggacga agccacactg   5220

gggtcatatt acactgctgc tgctaaaaag cggtttcagt ttaaagtggt cccaaattac   5280

ggtattacaa caaaggatgc agaaaagaac atatggcagg tcttagtaaa tattaaaaat   5340

gtaaaaatga gtgcgggcta ctgccctttg tcattagaat ttgtgtctgt gtgtattgtt   5400

tataaaaata atataaaatt gggtttgagg gagaaagtaa cgagtgtgaa cgatggagga   5460

cccatggaac tttcggaaga agttgttgat gagttcatgg agaatgttcc aatgtcggtt   5520

agactcgcaa agtttcgaac caaatcctca aaaagaggtc cgaaaaataa taataattta   5580

ggtaaggggc gttcaggcgg aaggcctaaa ccaaaaagtt ttgatgaagt tgaaaaagag   5640

tttgataatt tgattgaaga tgaagccgag acgtcggtcg cggattctga ttcgtattaa   5700

atatgtctta ctcaatcact tctccatcgc aatttgtgtt tttgtcatct gtatgggctg   5760

accctataga attgttaaac gtttgtacaa attcgttagg taaccagttt caaacacagc   5820

aagcaagaac tactgttcaa cagcagttca gcgaggtgtg gaaacctttc cctcagagca   5880

ccgtcagatt tcctggcgat gtttataagg tgtacaggta caatgcagtt ttagatcctc   5940

taattactgc gttgctgggg gcttttgata ctaggaatag aataatcgaa gtagaaaacc   6000

agcagagtcc gacaacagct gaaacgttag atgctacccg cagggtagac gacgctacgg   6060

ttgcaattcg gtctgctata aataatttag ttaatgaact agtaagaggt actggactgt   6120

acaatcagaa tacttttgaa agtatgtctg ggttggtctg gacctctgca cctgcatctt   6180

aaatgcatag gtgctgaaat ataaagtttg tgtttctaaa acacacgtgg tacgtacgat   6240

aacgtacagt gtttttccct ccacttaaat cgaagggtag tgtcttggag cgcgcggagt   6300

aaacatatat ggttcatata tgtccgtagg cacgtaaaaa aagcgaggga ttcgaattcc   6360

cccggaaccc ccggttgggg ccca                                         6384
```

<210> SEQ ID NO 36
<211> LENGTH: 300
<212> TYPE: DNA
<213> ORGANISM: Escherichia coli

<400> SEQUENCE: 36

```
caataacata cggcgtgaca tcggcttcaa atggcgtata gccgccctga tgctccatca     60

cttcctgatt attgacccac actttgccgt aatgagtgac cgcatcgaaa cgcagcacga    120

tacgctggcc tgcccaacct ttcggtataa agacttcgcg ctgataccag acgttgcccg    180

cataattacg aatatctgca tcggcgaact gatcgttaaa actgcctggc acagcaattg    240

cccggctttc ttgtaacgcg ctttcccacc aacgctgatc aattccacag ttttcgcgat    300
```

<210> SEQ ID NO 37
<211> LENGTH: 100
<212> TYPE: DNA
<213> ORGANISM: Escherichia coli

<400> SEQUENCE: 37

```
tcggcgaact gatcgttaaa actgcctggc acagcaattg cccggctttc ttgtaacgcg     60

ctttcccacc aacgctgatc aattccacag ttttcgcgat                          100
```

-continued

<210> SEQ ID NO 38
<211> LENGTH: 50
<212> TYPE: DNA
<213> ORGANISM: Escherichia coli

<400> SEQUENCE: 38
ttgtaacgcg ctttcccacc aacgctgatc aattccacag ttttcgcgat 50

<210> SEQ ID NO 39
<211> LENGTH: 20
<212> TYPE: DNA
<213> ORGANISM: Escherichia coli

<400> SEQUENCE: 39
aattccacag ttttcgcgat 20

VIRUS VECTOR AND USE THEREOF

TECHNICAL FIELD

The present invention relates to a technique for producing a protein from a polynucleotide containing a viral base sequence. More specifically, the present invention relates to (i) a polynucleotide containing a modified viral base sequence, (ii) a vector containing the polynucleotide, (iii) a plant or a transformant into which the vector is introduced, and (iv) a protein producing method and a protein producing kit, each of which utilizes the polynucleotide, the vector, the plant, or the transformant.

BACKGROUND ART

Examples of a method for producing a useful protein in a plant includes a method of using a transformed plant in which a foreign gene is introduced into a cell, and a method of infecting a plant cell with a virus vector. The method using a virus vector is advantageous since it provides higher expression efficiency than the method using a transformed plant.

Non Patent Document 1 discloses a method for expressing a foreign gene in a plant cell by infecting the plant cell with at least two agrobacteria into which virus vectors are introduced respectively. This method eliminates the need for creating a construct for each of plural genes when combinations of various genes are tested to find a combination for encoding a useful protein. Therefore, this method is useful in analyzing functions or the like of a large number of proteins. Further, a virus vector disclosed in Non Patent Literature 1 can realize high expression speed, can be constructed at a low cost, and can eliminate steps of a conventional gene recombination process.

It is desired that a useful protein produced in a plant can be produced efficiently and in mass scale since it is used not only for food, but also for medical products. In view of this, the inventors of the present invention have constructed a system for producing a protein by using a virus vector (see Patent Literatures 1 through 3).

As another system for producing a protein by using a virus vector, Patent Literature 4 discloses a method for increasing a production amount of a useful protein by improving efficiency of producing a transcription product. Patent Literature 4 discloses a method for expressing a target protein by inserting an intron sequence into a replication sequence of a virus vector, and introducing the virus vector thus obtained into a host cell. According to this method, in which an intron region containing a lot of adenosine (A), and thymidine (T) or uracil (U) is removed from the replication sequence of the virus vector or is substituted with an intron derived from a plant cell so that (i) decomposition of the transcription product in the plant cell can be suppressed and (ii) efficiency of producing the transcription product can be improved, it is possible to increase a production amount of a target protein.

Meanwhile, each of Non Patent Literatures 2 and 3 discloses a method for improving replication efficiency of a vector which is introduced in a host cell and which contains a base sequence of potyvirus. According to the method disclosed in Non Patent Literatures 2 and 3, an intron sequence is inserted into the base sequence of potyvirus so that a transformed sequence is obtained, and a vector containing the transformed sequence is introduced into *Escherichia coli*. In the *E. coli* to which the vector is introduced, introduction of intron suppresses expression of a virus protein encoded by the base sequence of potyvirus. This controls toxic influence of the virus on the *E. coli*, and attains better growth of the *E. coli*, thereby improving replication efficiency of the vector in the *E. coli*.

CITATION LIST

Patent Literature 1

Japanese Patent Application Publication, Tokukai, No. 2005-102652 A (Publication Date: Apr. 21, 2005)

Patent Literature 2

Japanese Patent Application Publication, Tokukai, No. 2005-245228 A (Publication Date: Sep. 15, 2005)

Patent Literature 3

Japanese Patent Application Publication, Tokukai, No. 2005-110594 A (Publication Date: Apr. 28, 2005)

Patent Literature 4

WO2005/049839 (Publication Date: Feb. 6, 2005)

Non Patent Literature 1

S. Marillonnet et al., PNAS, 101 (18): 6852-6857 (2004)

Non Patent Literature 2

I. E. Johansen, PNAS. USA, 93: 12400-12405 (1996)

Non Patent Literature 3

S. J. Yang et al., Arch Virol, 143: 2443-2451 (1998)

SUMMARY OF INVENTION

Introduction of a vector containing a virus DNA sequence into a host cell such as *E. coli* or *agrobacterium* worsens growth of the host cell, thereby completely inhibiting the growth of the host cell, or even if the host cell can grow, the host cell grows with a poorer growth rate. This causes a reduction in yield of the vector, thereby undesirably preventing a target useful protein from being efficiently produced using the vector.

According to the conventional protein producing methods described above, it is possible to increase a production amount of a target useful protein by improving a transcriptional activity in a host cell or increasing a production amount of a transcription product. However, these methods do not take into consideration growth of a host cell into which a vector containing a virus base sequence is introduced. As such, the growth of the host cell is inhibited, and this causes a reduction in yield of the vector containing the virus base sequence. This makes it difficult to efficiently carry out genetic recombination using the vector. That is, in a case where the vector is used for protein production, a reduction in yield of the vector causes a reduction in production amount of a useful protein using the vector.

The method disclosed in Non Patent Literatures 2 and 3 allows an improvement in growth of a host cell. However, expression of a virus protein is suppressed by inserting an intron into a viral sequence. This necessitates extracting an intron sequence from each molecule of a transcription product. This causes a reduction in growth rate of virus contained in a vector, thereby making it impossible to use the vector in efficiently producing a useful protein.

The present invention was attained in view of the above problems, and an object of the present invention is to provide a technique in which growth of a host cell, into which a vector containing a polynucleotide is introduced, is improved by using the polynucleotide containing a viral base sequence so that (i) replication efficiency of the vector in the host cell can be improved and (ii) efficiency of producing a protein using the vector can be improved.

In order to construct a virus vector, which contains a viral base sequence and does not causes deterioration in growth of a host cell, and loss of replication capability of the virus vector, the inventors of the present invention studied conditions required to construct such a virus vector. As a result of the study, the inventors of the present invention found that, in a case where a specific region of a base sequence of a tomato mosaic virus is modified, growth of a host cell, into which a vector containing the base sequence of the tomato mosaic virus is introduced, is not worsened, and that a yield of the vector in the host cell is increased accordingly. Based on this finding, the inventors of the present invention attained the present invention.

A polynucleotide of the present invention includes a viral base sequence, the viral base sequence containing: a first base sequence encoding a viral replication protein; and a second base sequence encoding a viral movement protein, the second base sequence being located downstream of the first base sequence and having a linking site for linking with an exogenous base sequence encoding a polypeptide to be expressed, and the linking site being located downstream of the second base sequence, the second base sequence being obtained by modifying with a base sequence in a native sequence derived from a virus by insertion, substitution, or addition.

The virus preferably belongs to a tobomovirus. Further, the virus is preferably a tobacco mosaic virus or a tomato mosaic virus.

It is preferable that the viral replication protein is: (i) polypeptides having amino acid sequences shown in SEQ ID NO: 1 and 2, respectively, or (ii) polypeptides having amino acid sequences which are mutants of the amino acid sequences shown in SEQ ID NO: 1 and 2, respectively, or which are one of the amino acid sequences shown in SEQ ID NO: 1 and 2 and a mutant of the other, wherein mutation of the mutants is deletion, substitution, or addition of one or several amino acids therein.

It is preferable that the viral movement protein is: (i) a polypeptide having an amino acid sequence shown in SEQ ID NO: 3, or (ii) polypeptide having an amino acid sequence in which one or several amino acids are deleted, substituted, or added in the amino acid sequence shown in SEQ ID NO: 3.

It is preferable that a polynucleotide having the second base sequence is: (i) a polynucleotide having the base sequence shown in any one of SEQ ID NO: 4 through 17, (ii) a polynucleotide having a base sequence in which one or several amino acids are deleted, substituted, or added in the base sequence shown in any one of SEQ ID NO: 4 through 17, (iii) a polynucleotide which hybridizes with a polynucleotide having a base sequence that is complementary to the base sequence shown in any one of SEQ ID NO: 4 through 17 under a stringent condition, and (iv) a polynucleotide having a base sequence which has at least 80% identity with the base sequence shown in any one of SEQ ID NO: 4 through 17.

It is preferable that the base sequence with which the second base sequence is modified by the insertion, substitution, or addition has a base length of 100 or more. Further, it is preferable that the second base sequence is obtained by adding the base sequence at any position from 17th base to 795th base of the base sequence shown in SEQ ID NO: 20.

A vector of the present invention contains any one of the polynucleotides.

A plant of the present invention contains any one of the polynucleotides.

A plant of the present invention contains the vector.

A transformant of the present invention contains any one of the polynucleotides.

A transformant of the present invention contains the vector.

A method of the present invention for producing a polypeptide, includes: transforming or transfecting a plant with the polynucleotide.

A method of the present invention for producing a polypeptide, includes: transforming a cell with the polynucleotide.

A kit of the present invention for producing a polypeptide, includes the polynucleotide.

A method of the present invention for producing a polypeptide, includes: transforming or transfecting a plant with the vector.

A method of the present invention for producing a polypeptide, includes: transforming a cell with the vector.

A kit of the present invention for producing a polypeptide, includes the vector.

A method of the present invention for producing a polypeptide, includes the step of: using the plant.

A method of the present invention for producing a polypeptide, includes the step of: using the transformant.

A kit of the present invention for producing a polypeptide, includes the plant.

A kit of the present invention for producing a polypeptide, includes the transformant.

For a fuller understanding of the nature and advantages of the invention; reference should be made to the ensuing detailed description taken in conjunction with the accompanying drawings.

DESCRIPTION OF EMBODIMENTS

Figure 1:
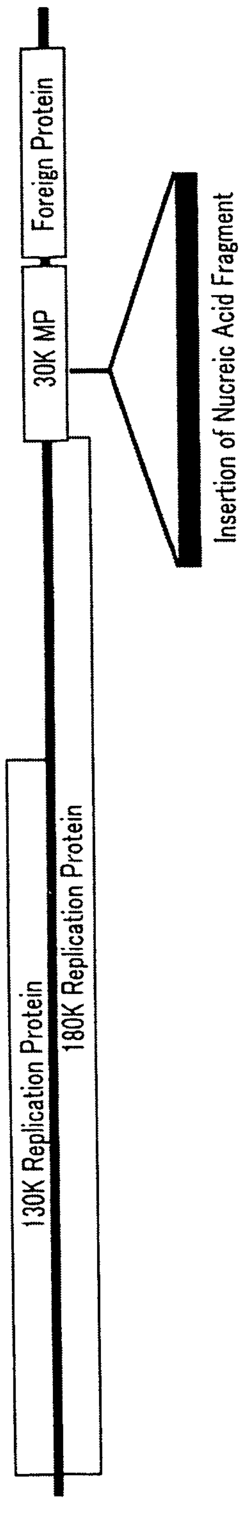
FIG. 1 is a view schematically illustrating a structure of a polynucleotide, according to the present invention, containing a viral base sequence.

Introduction of a vector containing a viral sequence into a host cell causes deterioration in growth of the host cell, and thereby causes a reduction in growth rate of the vector. This causes a reduction in amount of a protein that is produced using the vector and that is encoded by a foreign gene.

The inventors of the present invention aimed to construct an efficient protein producing system by constructing a vector which contains a viral sequence and which does not deteriorate growth of a host cell, and studied conditions required to construct such a vector.

[1. Polynucleotide Containing Viral Base Sequence, and Vector Containing the Polynucleotide]

The present invention provides a polynucleotide containing a viral base sequence which contains a first base sequence encoding a viral replication protein and a second base sequence encoding a viral movement protein.

The polynucleotide of the present invention containing the viral base sequences is a polynucleotide that is capable of functioning as a virus vector. The term "virus vector" used herein refers to a polynucleotide which contains a sequence derived from a viral genome and contains a foreign gene expressively, and preferably refers to (i) an RNA containing an RNA sequence derived from a virus, (ii) a DNA containing a cDNA sequence of an RNA derived from a virus, each of which contains a foreign gene expressively, or (ii) an RNA transcribed from this.

According to the polynucleotide of the present invention, the second base sequence is located downstream of the first base sequence. The polynucleotide of the present invention contains a part of or all of a native base sequence derived from a virus, and can be used to produce any protein in a cell.

The term "viral base sequence" used herein refers to a genome base sequence of a wild-type virus, and preferably refers to a genome RNA of an RNA virus or a cDNA obtained from the genome RNA.

The term "viral replication protein" used herein refers to a protein which is derived from a virus and which is involved in replication of a virus, and may be referred to simply as "replication protein". The protein which is involved in replication of a virus refers to a protein which replicates a virus in a cell infected with the virus. Such a protein may be a conventional replication protein, and examples of such a protein include an RNA dependent RNA polymerase (RdRp), an RNA replication enzyme, a tobacco mosaic virus 130K protein, a tobacco mosaic virus 180K protein, a tomato mosaic virus 130K protein, a tomato mosaic virus 180K protein, and the like.

A base sequence encoding the viral replication protein is preferably a native base sequence derived from a virus, but can be a base sequence which is transformed from a native base sequence derived from a virus and which encodes a protein having a replication functional activity. The term "replication functional activity" used herein refers to a functional activity of replicating a virus in a cell infected with the virus.

The term "viral movement protein" used herein refers to a protein which is derived from a virus and which is involved in intercellular movement of a virus, and may be referred to simply as "movement protein". The protein which is involved in intercellular movement of a virus refers to a protein which contributes to spread of infection of the virus by causing the virus to move from a cell infected with the virus to a neighboring cell. Such a protein may be a conventionally known movement protein, and examples of such a protein include a tobacco mosaic virus 30K protein, a tomato mosaic virus 30K protein, and the like.

A base sequence encoding the viral movement protein is preferably a native base sequence derived from a virus, but can be a base sequence which is transformed from a native base sequence derived from a virus and which encodes a protein having a movement functional activity or a base sequence which is transformed from a native base sequence derived from a virus and which encodes a protein that has lost the movement functional activity due to the transformation. The term "movement functional activity" used herein refers to a functional activity of causing a virus to move from a cell infected with the virus to a neighboring cell.

The virus is preferably a virus belonging to a tobamovirus, but is not limited to this. Examples of the virus include a tobacco mosaic virus (TMV), a tobacco mosaic virus-OM (TMV-OM), a tobacco mosaic virus-Cg (TMV-Cg), a tomato mosaic virus (ToMV), and a Sunn-hemp mosaic virus (SHMV). It should be noted that the virus is not limited to these.

The following description deals with the viral replication protein and the viral movement protein by taking a tomato mosaic virus as an example. Note that the tomato mosaic virus is a virus belonging to a tobamovirus.

Polypeptides constituting a replication protein of the tomato mosaic virus are provided as the amino acid sequences shown in SEQ ID NOs: 1 and 2, and base sequences of polynucleotide encoding the polypeptides are provided as the base sequences shown in SEQ ID NOs: 18 and 19.

In one aspect, the replication protein of the tomato mosaic virus can be (i) polypeptides respectively having the amino acid sequences shown in SEQ ID NO: 1 and 2 or (ii) polypeptides having amino acid sequences which are mutants of the amino acid sequences shown in SEQ ID NO: 1 and 2, or which are one of them and a mutant of the other one of them, each mutant polypeptide having a functional activity of replicating a virus genome.

In another aspect, the replication protein of the tomato mosaic virus can be (i) polypeptide encoded by polynucleotides respectively having the base sequences shown in SEQ ID NO: 18 and 19 or (ii) polypeptides encoded by base sequences which are mutants of the base sequences shown in SEQ ID NO: 18 and 19, or which are one of them and a mutant of the other one of them, each mutant polypeptide having a functional activity of replicating a virus genome.

That is, the replication protein of the tomato mosaic virus is constituted by two proteins, i.e., a 130K protein (referred to also as a 126K protein) having the amino acid sequence shown in SEQ ID NO: 1, and a 180K protein (referred to also as a 183K protein) having the amino acid sequence shown in SEQ ID NO: 2. The 130K protein is a direct translation product of the genome sequence of the tomato mosaic virus which is shown in SEQ ID NO: 35, and is encoded by the polynucleotide having the base sequence shown SEQ ID NO: 18. The 180K protein is a read-through translation product of the genome sequence of the tomato mosaic virus which is shown in SEQ ID NO: 35, and is encoded by a polynucleotide having the base sequence shown in SEQ ID NO: 19.

A polypeptide constituting a movement protein of the tomato mosaic virus is provided as an amino acid sequence shown in SEQ ID NO: 3, and a base sequence constituting a polynucleotide encoding the polypeptide is provided as a base sequence shown in SEQ ID NO: 20.

In one aspect, the movement protein of the tomato mosaic virus can be (i) a polypeptide having an amino acid sequence shown in SEQ ID NO: 3, (ii) a polypeptide which is a mutant of the polypeptide having an amino acid sequence shown in SEQ ID NO: 3 and which has a functional activity of causing a virus genome to move between cells, or (iii) a polypeptide which is a mutant of the polypeptide having an amino acid sequence shown in SEQ ID NO: 3 and which has lost the movement functional activity due to the mutation.

In another aspect, the movement protein of the tomato mosaic virus can be (i) a polypeptide which is encoded by a polynucleotide having a base sequence shown in SEQ ID NO: 20, (ii) a polypeptide which is encoded by a mutant of the polynucleotide having a base sequence shown in SEQ ID NO: 20 and which has a functional activity of causing a virus genome to move between cells, or (iii) a polypeptide which is encoded by a mutant of the polynucleotide having a base sequence shown in SEQ ID NO: 20 and which has lost the movement functional activity due to the mutation.

As long as it is used in association with a protein or a polypeptide, the term "mutant" used herein refers to a polypeptide which is different in amino acid sequence, but preserves an activity of a wild-type polypeptide. That is, in this specification, a mutant of a polypeptide can be a mutant having an amino acid sequence in which one or several amino acids are deleted, substituted, or added in a specific amino acid sequence.

It is known in the art that several amino acids in an amino acid sequence of a polypeptide can be easily modified without causing a significant influence on a structure or a function of the polypeptide. Further, it is also known that mutation occurs not only in an artificially modified protein, but also in a naturally existing protein without causing a significant change in structure and function of the protein. A person skilled in the art can easily modify one or several amino acids in an amino acid sequence of a polypeptide by utilizing a known art.

The above description has discussed the viral replication protein and the viral movement protein by taking the tomato mosaic virus as an example. However, a person skilled in the art will readily understand that the virus is not limited to the tomato mosaic virus.

Note that the term "protein" is exchangeable with "peptide" or "polypeptide". Further, the term "base sequence" is exchangeable with "nucleic acid sequence" or "nucleotide sequence", and is expressed as a sequence of bases, i.e., adenine (A), guanine (G), cytosine (C), and thymine (T) in deoxyribonucleotide, or adenine (A), guanine (G), cytosine (C), and uracil (U) in ribonucleotide.

The polynucleotide of the present invention has a linking site for linking with an exogenous base sequence encoding a polypeptide to be expressed, the linking site being located downstream of the second base sequence, the second base sequence being obtained by modifying with a base sequence to a native sequence derived from a virus by insertion, substitution, or addition. That is, a base sequence is added by insertion, substitution, or addition in the second base sequence which encodes the viral movement protein and which is located downstream of the first base sequence and upstream of the linking site for linking with the exogenous base sequence.

According to the polynucleotide of the present invention, the second base sequence is provided as a polynucleotide shown in SEQ ID NO: 4 through 17 or as a mutant of the polynucleotide.

As long as it is used in association with gene or polynucleotide, the term "mutant" used herein refers to a polynucleotide encoding a polypeptide which is different in base sequence but which preserves an activity inherent in polypeptide encoded by a wild-type polynucleotide. That is, in this specification, a mutant of a polynucleotide refers to (i) a polynucleotide having a base sequence in which one or several bases are deleted, substituted, or added in a specific base sequence, (ii) a polynucleotide which hybridizes with a polynucleotide having a specific base sequence or a base sequence that is complementary to the specific base sequence under a stringent condition, or (iii) a polynucleotide having a base sequence which has at least 80% identity with a specific base sequence.

The hybridization can be carried out by a known method such as a method described in "Molecular Cloning: A Laboratory Manual 3rd Edition, J. Sambrook and D. W. Russll, Cold Spring Harbor Laboratory, NY (2001)" (the contents of which are hereby incorporated by reference).

The term "stringent condition for hybridization" used herein refers to such a condition that (i) incubation is carried out overnight at 42° C. in a hybridization solution (50% formamide, 5×SSC (150 mM NaCl, 15 mM trisodium citrate), 50 mM sodium phosphate (pH7.6), 5×Denhardt's solution, 10% dextran sulfate, and 20 μg/ml of denatured and fragmented salmon sperm DNA); and then (ii) a filter is washed with 0.1×SSC at approximately 65° C.

The polynucleotide of the present invention is such that the linking site for linking with an exogenous base sequence encoding a polypeptide to be expressed is located downstream of the second base sequence which is located downstream of the first base sequence. The exogenous base sequence is linked with the linking site and a cell is transformed using the polynucleotide containing the exogenous base sequence so that a polypeptide encoded by the exogenous base sequence can be expressed in the cell. Note that the exogenous base sequence linked with the polynucleotide of the present invention does not need to be located adjacently to the second base sequence.

The linking site, of the polynucleotide of the present invention, for linking with the exogenous base sequence does not need to exist as a cassette in the base sequence of the polynucleotide of the present invention, provided that the exogenous base sequence can be inserted into or linked with the base sequence of the polynucleotide of the present invention. The polynucleotide of the present invention makes it possible to amplify a gene having the exogenous base sequence linked with the linking site, and thereby makes it possible to produce a product of the gene.

According to the polynucleotide of the present invention, the second base sequence is a mutant of a native sequence derived from a virus, wherein the mutation adds a base sequence to the native sequence by insertion, substitution, or addition. The term "native sequence derived from a virus" used herein refers to a sequence indigenous in a wild-type virus. That is, such a native sequence can be a natural sequence which is obtained from a wild-type virus and which is not mutated.

The second base sequence of the present invention may be obtained by modifying with a base sequence in a mutant base sequence of a native base sequence derived from a virus which mutant base sequence encodes a polypeptide having the movement functional activity wherein the modification modifies with a base sequence in the native base sequence by insertion, substitution, or addition. Further, the second base sequence of the present invention may be obtained by modifying with a base sequence in a mutant base sequence of a native base sequence derived from a virus which mutant base sequence encodes a polypeptide having no movement functional activity due to the mutation wherein the modification modifies with a base sequence in the native base sequence by insertion, substation, or addition.

In the polynucleotide of the present invention, the base sequence which is included in the second base sequence by insertion, substitution, or addition can be any base sequence having a certain base length, and therefore can have any sequence and can be derived from anything. In this specification, such a base sequence which is added to the second base sequence by insertion, substitution, or addition may be also referred to simply as "insertion sequence". In later described Examples of the present invention, a sequence derived from *Escherichia coli* transposon IS2 and a sequence derived from reverse complement of a GUS gene were used as the insertion sequences. These sequences were successfully used as the insertion sequences in the Examples.

In one embodiment, an insertion sequence used in the polynucleotide of the present invention may have 100 bases or more, preferably has 100-1609 bases, and more preferably has 300-1609 bases. The inclusion of such an insertion sequence having not less than 100 base length in the second base sequence of the polynucleotide of the present invention by insertion, substitution, or addition causes a further improvement in growth of a host cell into which the polynucleotide is introduced (see the Example described later). This improves efficiency of replicating a vector in the cell, thereby allowing a further increase in yield of the vector.

The insertion sequence can be inserted in any position in a native sequence derived from a virus in order to obtain the second base sequence used in the polynucleotide of the present invention. The insertion sequence is preferably inserted in a region of the second base sequence which exists between a C-terminal region of the first base sequence and a start codon region of the exogenous base sequence linked with the linking site, and is more preferably inserted between a stop codon of the first base sequence and a subgenome promoter of a base sequence encoding a coat protein. However, the position where the insertion sequence is inserted is not limited to these. Further, the second base sequence can be obtained by adding the insertion sequence to the native sequence derived from a virus or can be obtained by substituting a part of the native sequence derived from a virus with the insertion sequence. Further, the second base sequence can be obtained by deleting a part of the native sequence derived from a virus and inserting the insertion sequence in a section where the part of the native sequence was deleted.

That is, the second base sequence of the present invention is a sequence obtained by mutating, as described above, a sequence encoding a protein which preserves a function of causing a viral genome to move between cells.

In one embodiment, the insertion sequence can be inserted in any position of the second base sequence used in the polynucleotide of the present invention. The position where the insertion sequence is inserted is not limited to a specific one, but the insertion sequence is preferably inserted in any position from 17th base to 795th base of the base sequence shown in SEQ ID NO: 20, and more preferably inserted in any position from 17th base to 620th base of the base sequence shown in SEQ ID NO: 20.

Further, the second base sequence used in the polynucleotide of the present invention may be obtained by adding the insertion sequence to 5' or 3' terminal of the base sequence shown in SEQ ID NO: 20 or may be obtained by substituting a part of the base sequence shown in SEQ ID NO: 20 with the insertion sequence.

The present invention also provides a vector for producing a polypeptide as desired. The vector of the present invention can be such a vector that contains a polynucleotide containing a viral base sequence and that is capable of expressing the polynucleotide in a host cell into which the vector is incorporated, the viral base sequence containing a first base sequence encoding a viral replication protein and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition.

A vector containing a viral base sequence can be easily mutated, and therefore construction of such a vector is very difficult, or impossible in some cases depending on the type of a foreign gene to be expressed. However, the use of the polynucleotide of the present invention made it possible to construct such a vector that could not be constructed before. It can be estimated from this that a vector constructed using the polynucleotide of the present invention is a stable vector in which occurrence of mutation is suppressed.

Further, the vector of the present invention allows an improvement in growth of the host cell into which the vector is introduced, thereby improving replication efficiency in the host cell. Because of this, a useful protein, which is encoded by a foreign gene, can be efficiently produced by using a replicated vector.

The vector containing the polynucleotide of the present invention may be, for example, an expression vector (e.g. phage vector or plasmid vector), which can express the polynucleotide, such as a pBR type or a pUC type. A vector which can express the polynucleotide in a host cell into which the vector of the present invention is introduced can be appropriately selected as such a vector. Further, a vector which has a property of being incorporated into a genome of a plant cell can be a vector such as a pBI type or a pCAMBIA type, and can be a Ti plasmid vector, for example.

How to construct the polynucleotide of the present invention and the vector of the present invention is not limited particularly, and they may be constructed by a known genetic engineering method.

The vector constructed using the polynucleotide of the present invention can be suitably used in production of a protein encoded by a foreign gene. That is, transformation of a host cell by using a vector containing the polynucleotide of the present invention can efficiently replicate the vector without worsening growth of the host cell, thereby making it possible to efficiently produce, by using the replicated vector, the protein encoded by the foreign gene.

The foreign gene linked with the linking site contained in the polynucleotide of the present invention or the vector of the present invention is not limited to a specific one, and therefore can be a GFP gene, a human gamma interferon gene, an alpha interferon gene, a calmodulin gene, a myosin phosphatase inhibitor protein (CPI-17) functional domain gene (amino acid residue: 22-120), or a single chain antibody gene, for example. The use of the polynucleotide of the present invention or the vector of the present invention allows easy preparation of a vector carrying such a gene, efficient replication of such a vector and efficient production of a protein from the gene by using the replicated vector.

[2. Plant Containing Viral Base Sequence]

The present invention also provides a plant containing a viral base sequence. The term "plant" used herein refers to a plant cell or a plant individual, and examples of the plant include plants such as *Arabidopsis*, tobacco, or benthamiana, and plant cells such as a tobacco BY2 cell or an *Arabidopsis* mm2d cell.

The plant of the present invention contains a first base sequence encoding a viral replication protein and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition. With this, the polypeptide can be efficiently expressed.

In one embodiment, the plant of the present invention is obtained by introducing, into an organism, a polynucleotide containing a viral base sequence or a vector containing the polynucleotide, the viral base sequence containing a first base sequence encoding a viral replication protein and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition.

In one aspect, the plant of the present invention may be obtained by transforming a plant or a plant cell using the polynucleotide of the present invention or a vector containing the polynucleotide of the present invention. The plant of the present invention can be obtained, for example, by introducing the polynucleotide of the present invention into a plant cell by a method such as electroporation.

In another aspect, the plant of the present invention can be obtained by transfecting a plant or a plant cell with the polynucleotide of the present invention or a vector containing the polynucleotide of the present invention. The plant of the present invention can be obtained, for example, by infecting a plant or a plant cell with the polynucleotide of the present invention. Further, the plant of the present invention can also be obtained by transfecting a plant cell with a plasmid into which cDNA obtained by adding a promoter to the polynucleotide of the present invention has been introduced and transcribing the cDNA in the cell. Further, the plant of the present invention can also be obtained by transfecting a plant cell with cDNA of the polynucleotide of the present invention and transcribing the cDNA in the cell.

Further, the plant of the present invention can also be obtained by infecting a plant cell with *agrobacterium* into which a plasmid vector containing the polynucleotide of the present invention is introduced, for example. Further, the plant of the present invention can also be obtained by agroinfiltration utilizing *agrobacterium*. Specifically, the polynucleotide of the present invention is locally introduced into a plant body by infiltrating a culture solution, in which *agrobacterium* containing the polynucleotide of the present invention is incubated, into intercellular space of the plant body.

That is, the plant of the present invention may be a transformed plant which has been transformed using the polynucleotide of the present invention or the vector of the present invention, or can be an infected plant which is infected with the polynucleotide of the present invention or the vector of the present invention. In a case where the plant of the present invention is a transformed plant, it can be a transient transformant in which the polynucleotide of the present invention which is introduced into a plant does not integrate with the genome of the plant and is transiently expressed, or can be a stable transformant in which the polynucleotide of the present invention which is introduced in a plant integrates with the genome of the plant and is stably and continuously expressed. Further, in the transformed plant, polynucleotide of the present invention which is introduced into the plant may be constantly expressed or may be inducibly expressed using steroid hormone or the like. In a case where the plant of the present invention is an infected plant, the plant may be entirely infected with the polynucleotide of the present invention or may be locally infected with the polynucleotide of the present invention.

Since the plant of the present invention contains the polynucleotide of the present invention, the use of the plant of the present invention allows efficient production of a protein encoded by a foreign gene which is incorporated in the polynucleotide of the present invention or the vector of the present invention.

[3. Transformant Containing Viral Base Sequence]

The present invention also provides a transformant containing a viral base sequence. The term "transformant" includes not only cell, tissue, and organ, but also individual organism, but the transformant is preferably a cell (especially prokaryotic cell, fungus, or the like). A transformant of the present invention can be *Escherichia coli, agrobacterium*, or yeast, for example.

The transformant of the present invention contains a polynucleotide containing a first base sequence encoding a viral replication protein and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition. As such, the transformant of the present invention can be used in efficient expression of the polypeptide.

In one embodiment, the transformant of the present invention is obtained by introducing, into an organism, a polynucleotide containing a viral base sequence or a vector containing the polynucleotide, the viral base sequence containing a first base sequence encoding a viral replication protein and a second base sequence encoding a viral movement protein, the second base sequence being located downstream of the first base sequence and having a linking site for linking with an exogenous base sequence encoding a polypeptide to be expressed, the linking site being located downstream of the second base sequence, the second base sequence being obtained by modifying with a base sequence in a native sequence derived from a virus by insertion, substitution, or addition.

In one aspect, the transformant of the present invention can be obtained by transforming an organism using the polynucleotide of the present invention or the vector containing the polynucleotide of the present invention. For example, the transformant of the present invention can be obtained by introducing a plasmid, into which the polynucleotide of the present invention is incorporated, into *Escherichia coli* by a method such as a calcium chlorite method.

The use of the transformant of the present invention allows an increase in yield of the vector of the present invention which is introduced into a host cell, for example. That is, the use of the transformant of the present invention makes it possible to easily and efficiently produce a vector for producing a protein encoded by a foreign gene incorporated into the vector. Further, since growth of the transformant can be improved, the use of the transformant allows efficient production of a protein encoded by a foreign gene incorporated into the vector of the present invention.

[4. Method and Kit for Producing Polypeptide in a Cell as Desired]

The present invention also provides (i) a method for producing a polypeptide using the polynucleotide, the vector, the plant, or the transformant, and (ii) a kit for producing a polypeptide, the kit including the polynucleotide, the vector, the plant, or the transformant.

A method of the present invention for producing a polypeptide uses the polynucleotide, the vector, the plant, or the transformant. A kit of the present invention for producing a polypeptide includes the polynucleotide, the vector, the plant, or the transformant. Note that the term "kit" used herein means that at least one of the components is contained in another material (e.g. container).

The present invention provides a method and a kit for efficiently producing any polypeptide. The use of the method of the present invention for producing any polypeptide in a cell does not cause deterioration in growth of the cell even if a viral base sequence is introduced into the cell, thereby allowing efficient production of the polypeptide.

In one embodiment, the method of the present invention for producing a polypeptide uses the polynucleotide of the present invention or the vector containing the polynucleotide, the method including the step of transforming or transfecting aliving specimen with the polynucleotide of the present invention or the vector of the present invention, wherein the living specimen may or may not be a plant body or a plant cell. A polypeptide encoded by an exogenous base sequence contained in the polynucleotide of the present invention or the vector of the present invention is expressed in the organism thus transformed or transfected in the step.

In another embodiment, the method of the present invention for producing a polypeptide uses the plant of the present invention or the transformant of the present invention, the method including the step of growing or incubating the plant of the present invention or the transformant of the present invention under a condition that a polypeptide can be expressed. A polypeptide encoded by an exogenous base sequence contained in the plant or the transformant is expressed in the plant or the transformant in the step.

As described above, the use of the method of the present invention for producing a polypeptide does not cause deterioration in growth of an organism in which a predetermined polypeptide is produced, thereby making it possible to efficiently produce the polypeptide.

A method of the present invention for introducing a polypeptide or a vector into a host is not limited to a specific one, and a conventionally known method such as an *agrobacterium* method, electroporation, a calcium phosphate method, a liposome method, or a DEAE dextran method can be suitably used as such a method. Further, an organism which is transformed or transfected with the vector of the present invention is not limited to a specific one, and therefore can be a cell derived from an animal or a cell derived from a plant. Further, a microorganism such as *Bacillus subtilis, Escherichia coli*, fungus, or yeast can be used as the host.

A method of the present invention for introducing the polynucleotide of the present invention or the vector of the present invention into a plant body or a cell derived from a plant is not limited to a specific one, and a method such as the *agrobacterium* method, the agroinfiltration, a polyethylene glycol method, the electroporation, or a particle gun method can be suitably used as such a method.

The kit of the present invention for producing a polypeptide includes the polynucleotide of the present invention, the vector of the present invention, the plant of the present invention, or the transformant of the present invention. In a preferable embodiment, the kit of the present invention for producing a polypeptide, including the polynucleotide of the present invention or the vector of the present invention preferably further includes a plant body or an organism to be transformed or transfected. With this arrangement, a cell is transformed or transfected using the polynucleotide of the present invention or the vector of the present invention so that a polynucleotide encoded by an exogenous base sequence contained in the polynucleotide of the present invention or the vector of the present invention can be expressed in the plant body or the organism into which the cell has been introduced.

Note that the method and the kit for producing any polypeptide in a cell is not limited to those explained above, and a person skilled in the art who read this specification can easily understand other aspects of the method and the kit for producing a polypeptide.

The following description deals with more detailed explanation of the present invention with reference to the Examples, but the present invention is not limited to these Examples, but may be altered by a skilled person within the scope of the claims and the embodiment. An embodiment based on a proper combination of technical means disclosed in different embodiments is encompassed in the technical scope of the present invention.

EXAMPLES

Example 1

Figure 2A:
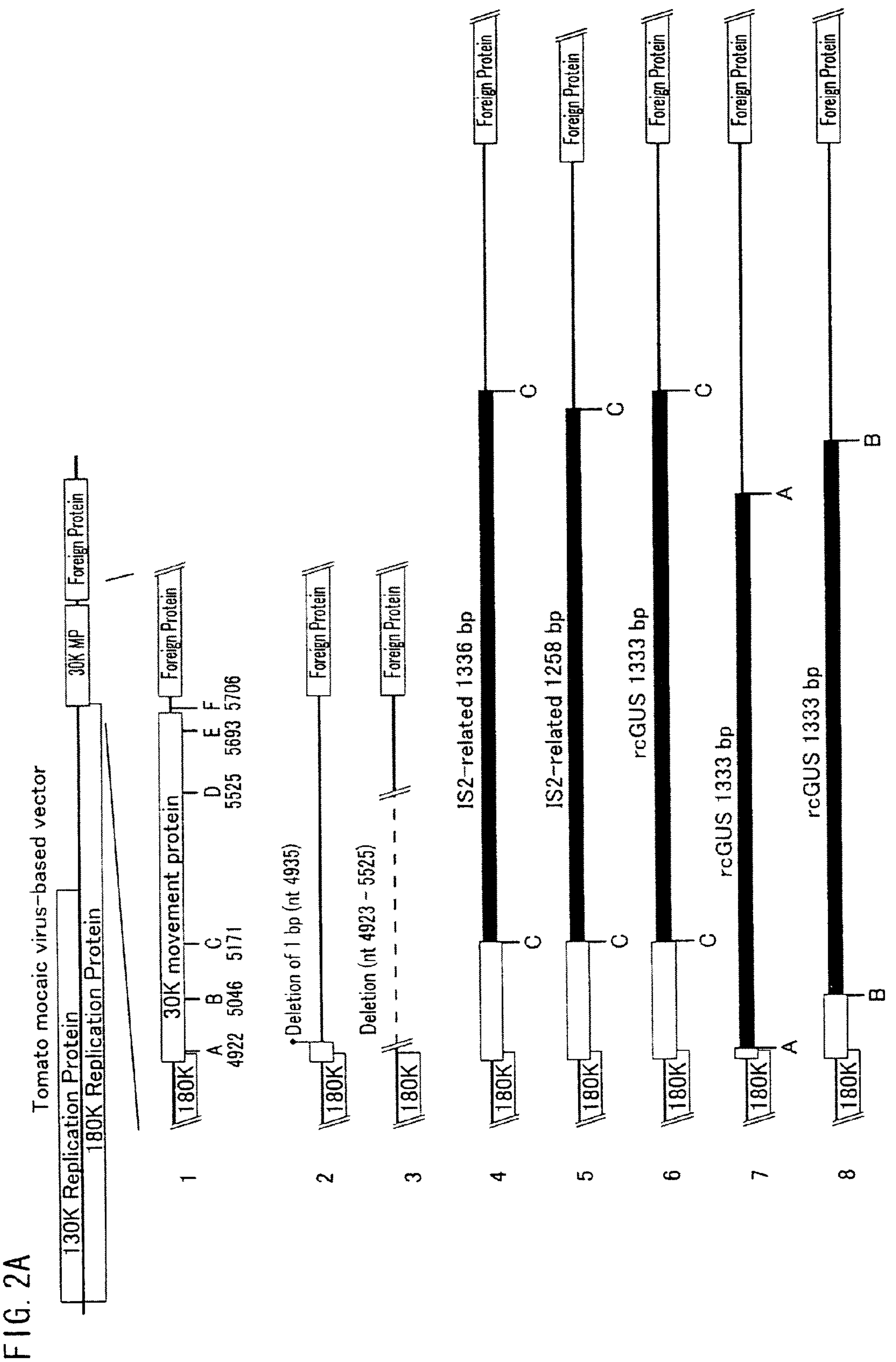
FIG. 2A is a view schematically illustrating structures of plasmid constructs constructed in an Example of the present invention.
Figure 2B:
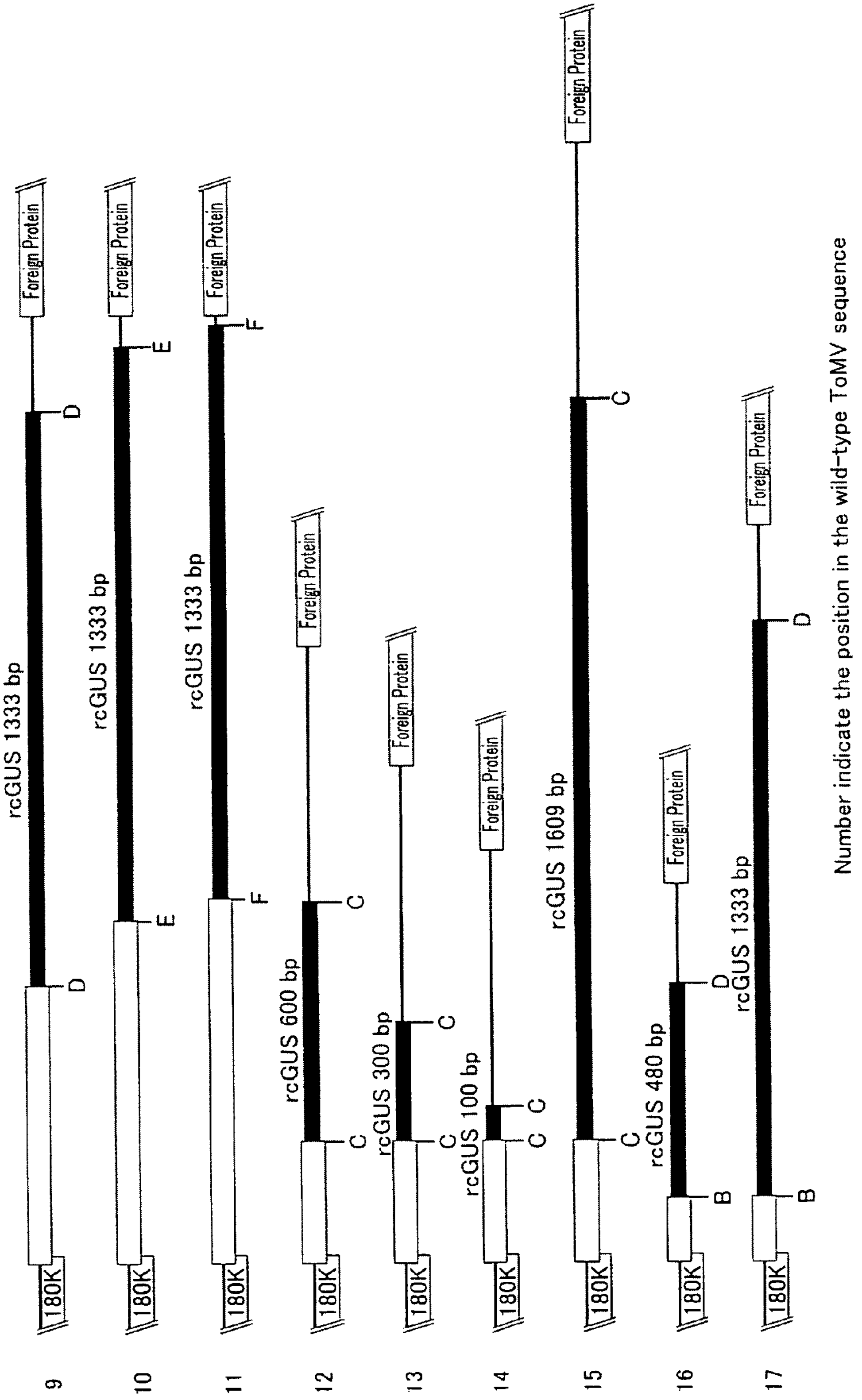
FIG. 2B is a view schematically illustrating structures of plasmid constructs constructed in the Example of the present invention.

Construction of Plasmid for Producing GFP cDNAs of a tomato mosaic virus were synthesized by inserting various base sequences (SEQ ID NO: 21 through 34) into a base sequence (SEQ ID NO: 20) of a gene encoding a movement protein. The base sequence is located between a base sequence of a gene encoding a tomato mosaic virus replication protein and a base sequence of a gene encoding a target foreign protein. The cDNAs thus synthesized were used to construct plasmid constructs, respectively (see FIG. 1), FIGS. 2A and 2B show positions of respective insertion base sequences with which the base sequence of the gene encoding the movement protein was modified by insertion, substitution, or addition. In FIGS. 2A and 2B, A through F indicate respective positions where the respective insertion base sequences were inserted, and numbers below the alphabets indicate respective positions of the respective insertion base sequences in a native sequence of the tomato mosaic virus. Note that a construct indicated by No. 16 (piLrcG11erG3SRz) was obtained by substituting a base sequence between B and D with the base sequence shown in SEQ ID NO: 33, and a construct indicated by No. 17 (piLrcG12erG3SRz) was obtained by substituting a base sequence between B and D with the base sequence shown in SEQ ID NO: 34.

In this Example, an insertion sequence added into the constructs indicated by No. 4 and No. 5 (piLIS2erG3SRz and piLIS2(-SpeI)erG3SRz) in Table 1 was a base sequence derived from *Escherichia coli* transposon IS2. Meanwhile, an insertion sequence added into each of the other constructs was a sequence derived from reverse complement of a GUS gene. Further, in this Example, a gene encoding a GFP protein was used as a gene encoding a target foreign protein.

The plasmid constructs constructed as above were used to transform *Escherichia coli*. One of colonies obtained from the transformed *E. coli* was inoculated into a 3 ml LB culture medium containing antibiotics for selection, and then was incubated at 37° C. for 20 hours with shaking. A plasmid was purified from a 1.5 ml incubation solution by an alkali SDS method. The plasmid thus purified was quantified using a DNA assay kit (Quant-it dsDNA Assay Kit (invitrogen)).

Yields of the plasmid constructs obtained in a cell was compared with a yield of a plasmid construct into which no insertion sequence was inserted, and obtained relative values are shown in Tables 1 and 2.

TABLE 1

| | Plasmid Name | Inserted Position | SEQ ID NO | Number of Inserted Bases (bp) | Yield of Plasmid (relative value) | SE |
|---|---|---|---|---|---|---|
| 1 | piLerG3SRz | — | — | — | 1.0 | 0.1 |
| 2 | piLerG3(SF3)SRz | — | — | — | 0.6 | 0.0 |
| 3 | piLΔMPerG3SRz | — | — | — | 0.6 | 0.0 |
| 4 | piLIS2erG3SRz | C | 21 | 1336 | 17.2 | 0.6 |
| 5 | piLIS2(-SpeI)erG3SRz | C | 22 | 1258 | 16.3 | 0.6 |
| 6 | piLrcG1erG3SRz | A | 23 | 1333 | 14.1 | 0.3 |
| 7 | piLrcG2erG3SRz | B | 24 | 1333 | 13.1 | 0.4 |
| 8 | piLrcG3erG3SRz | C | 25 | 1338 | 13.4 | 0.4 |
| 9 | piLrcG8erG3SRz | D | 26 | 1333 | 12.3 | 0.3 |
| 10 | piLrcG9erG3SRz | E | 27 | 1333 | 12.5 | 0.4 |
| 11 | piLrcG10erG3SRz | F | 28 | 1333 | 14.4 | 0.2 |
| 14 | piLrcG6erG3SRz | C | 31 | 100 | 2.2 | 0.1 |
| 15 | piLrcG7.5erG3SRz | C | 32 | 1604 | 13.6 | 0.7 |
| 16 | piLrcG11erG3SRz | B/D | 33 | 480 | 9.4 | 0.5 |
| 17 | piLrcG12erG3SRz | B/D | 34 | 1333 | 14.0 | 0.5 |

TABLE 2

| | Plasmid Name | Inserted Position | SEQ ID NO | Number of Inserted Bases (bp) | Yield of Plasmid (relative value) | SE |
|---|---|---|---|---|---|---|
| 1 | piLerG3SRz | — | — | — | 1.0 | 0.1 |
| 12 | piLrcG4erG3SRz | C | 29 | 600 | 5.0 | 0.1 |
| 13 | piLrcG5erG3SRz | C | 30 | 300 | 4.3 | 0.3 |

As shown in Tables 1 and 2, yields of the plasmid constructs (indicated by No. 4 through No. 17, respectively) into which the base sequences respectively shown in SED ID NO: 21 through 34 were inserted increased by 2.2 to 17.2 times compared with the plasmid construct (indicated by No. 1) containing a native base sequence into which no insertion sequence was inserted. Note that a plasmid construct in which a gene encoding the movement protein was frameshifted (plasmid construct indicated by No. 2), and a plasmid construct in which a gene encoding the movement protein was deleted (plasmid construct indicated by No. 3) did not increase in yield.

Example 2

Improvement in Growth Condition of Host Microorganism Cell

The plasmid constructs constructed in the Example 1 were used to transform *Escherichia coli* JM109 (TOYOBO). The *Escherichia coli* JM109 thus transformed was placed on an LB agar medium containing 100 μg/ml carbenicillin and was incubated at 37° C. for 18 hours. Five colonies whose growth was not affected by other colonies were randomly selected from obtained colonies, and each of the five colonies was measured in major axis.

Figure 3:
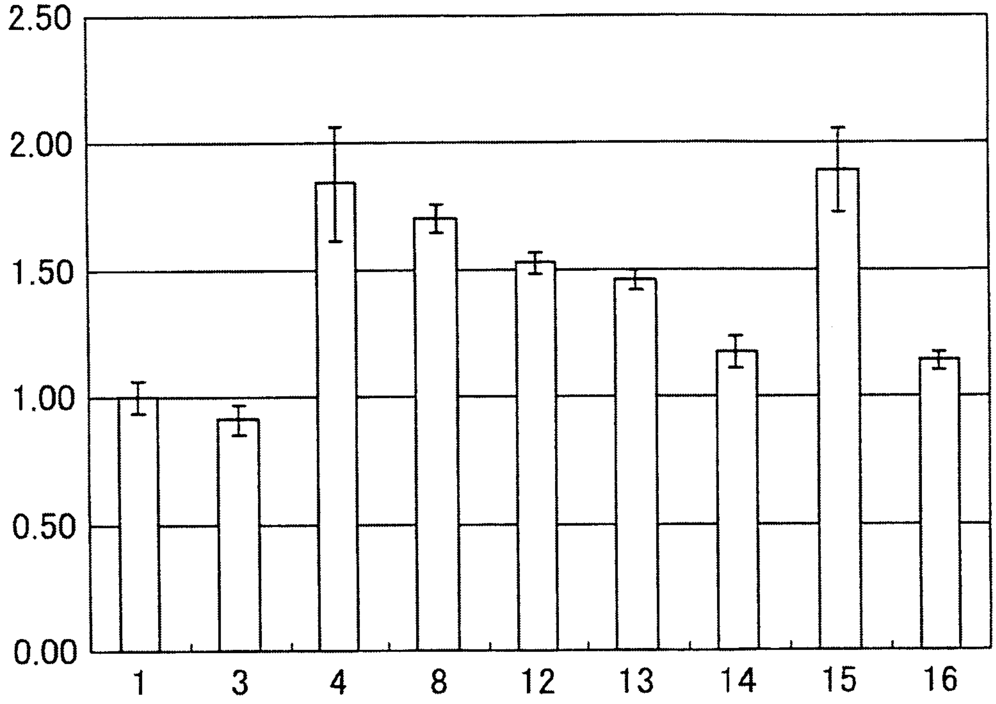
FIG. 3 is a graph showing the diameter of *Escherichia coli* colonies having respective plasmid constructs in an Example of the present invention.

A colony having a plasmid construct containing an insertion sequence and a colony having a plasmid construct containing no insertion sequence among the plasmid constructs constructed in the Example 1 were compared in major axis. Table 1 and FIG. 3 show obtained relative values of the major axis.

TABLE 3

| | Plasmid Name | Major Axis (relative value) |
|---|---|---|
| 1 | piLerG3SRz | 1.0 |
| 3 | piLΔMPerG3SRz | 0.91 |
| 4 | piLIS2erG3SRz | 1.84 |
| 8 | piLrcG3erG3SRz | 1.70 |
| 12 | piLrcG4erG3SRz | 1.53 |
| 13 | piLrcG5erG3SRz | 1.46 |
| 14 | piLrcG6erG3SRz | 1.18 |
| 15 | piLrcG7.5erG3SRz | 1.89 |
| 16 | piLrcG11erG3SRz | 1.14 |

As shown in Table 3, the major axis of an *Escherichia coli* colony having a plasmid construct containing an insertion sequence (plasmid construct indicated by 4, 8, 12, 13, 14, 15, or 16) was 1.14 to 1.89 times larger than the major axis of an *Escherichia coli* colony having a plasmid construct containing no insertion sequence (plasmid construct indicated by 1 or 3). This demonstrates that a growth condition of *Escherichia coli* into which a plasmid construct containing a viral base sequence was introduced was improved (see FIG. 3).

Example 3

Construction of Plasmid for Production of Foreign Protein

In the Example 3, plasmid constructs were constructed by using a human gamma interferon (hIFNγ) gene as a gene encoding a foreign protein.

The hIFNγ gene was amplified by the PCR method by using an AatII recognition site at the 5'-terminal side and a BstEII site at the 3'-terminal side of a GFP gene of each of the plasmid constructs constructed in the Example 1 (No. 1 (piLerG3SRz), No. 3 (piLΔMPerG3SRz), No. 4 (piLIS2erG3SRz), No. 6 (piLrcG1erG3SRz), and No. 8 (piLrcG3erG3SRz) (see Table 1)). The hIFNγ gene was then accurately substituted, so that plasmid constructs (No. 1' (piLhIFNγSRz), No. 3' (piLΔMPhIFNγSRz), No. 4' (piLIS2hIFNγSRz), No. 6' (piLrG1hIFNγSRz), and No. 8' (piLrG3hIFNγSRz)) were constructed.

Yields of the plasmid constructs in respective cells was quantitatively analyzed in the same manner as in the Example 1. The result demonstrated that a yield of a plasmid construct into which an insertion base sequence was inserted (No. 4', 6', or 8') was much larger than that of a plasmid construct in which no insertion base sequence was inserted (No. 1' or 3').

It was also possible to easily construct a plasmid construct, into which a cDNA of a virus genome RNA mutated as shown in No. 4 of FIG. 2A was introduced, the virus genome RNA being mutated by using, as a gene encoding a foreign protein, an alpha interferon gene, a myosin phosphatase inhibitor protein (CPI-17) functional domain gene (amino acid residue: 22-120), a single chain antibody gene, or a calmodulin gene in a similar manner to the above Example. The plasmid construct was obtained in good yield with good stability.

Example 4

Construction of Binary Plasmid

Further, each of the plasmid constructs constructed as above was cleaved with SpeI and AvrII, and was linked with a SpeI recognition site of pBICER8-ToMV5'-Spe (Dohi et al, 2006, Archives of Virlogy, 151: 1075-1084) in order to introduce a base sequence of a virus containing the hIFNγ gene into a binary plasmid that was to be used for inducing expression of the viral sequence therein. Although a binary plasmid into which a gene fragment derived from the plasmid construct indicated by 1' or 3' was inserted could not be obtained, a binary plasmid into which a gene fragment derived from the plasmid construct indicated by 4', 6', or 3' was inserted could be easily obtained. This revealed that a plasmid construct which contains a foreign gene and whose construction is difficult can be constructed by inserting, substituting or adding an insertion sequence in a base sequence encoding a viral movement protein.

It was also possible to easily construct a binary plasmid, into which a cDNA of a virus genome RNA mutated as shown in No. 4 of FIG. 2A was introduced, the virus genome RNA being mutated by using, as a gene encoding a foreign protein, an alpha interferon gene, a CPI-17 protein functional domain gene, a single chain antibody gene, or a calmodulin gene in a similar manner to the above Example. The binary plasmid was obtained in good yield with good stability.

Example 5

Expression of Protein in Protoplast

As shown in No. 4 through No. 15 of FIGS. 2A and 2B, an insertion sequence was inserted, substituted, or added in a virus genome RNA that was synthesized in a test tube with the use of T7RNA polymerase. Thus, a mutant of the virus genome RNA was created. The virus genome RNA thus created was inoculated into a protoplast, which was prepared from a tobacco BY2 cell, by electroporation (as for an experimental method, see Watanabe et al, FEBS Letters, 219:65-69). A transformant of the protoplast thus obtained was incubated at 26° C. for 24 hours, and then was sampled.

In a protoplast which contains a virus genome RNA into which a GFP gene was introduced as a foreign gene, proliferation of the virus genome RNA was confirmed by northern blotting. In protoplasts which respectively contain virus genome RNAs shown in No. 4 through No. 15, respectively, proliferation of the virus genome RNAs was confirmed. Further, proliferation of a sub genome GFP messenger RNA was confirmed in each of protoplasts respectively containing virus genome RNAs having respective insertion sequences shown in No. 4 through No. 9 and No. 12 through No. 15, respectively. Meanwhile, accumulation of the sub genome GFP messenger RNA could not be detected in each of protoplasts respectively containing virus genome RNAs shown in No. 10 and No. 11, respectively.

In the protoplasts, expression of a GFP gene was confirmed with the use of a fluorescent microscope. Note that expression of a GFP gene was confirmed in each of the protoplasts respectively containing the virus genome RNAs shown in No. 4 through No. 9 and No. 12 through No. 15, but expression of a GFP gene was not confirmed in each of the protoplasts respectively containing the virus genome RNAs shown in No. 10 and No. 11.

It can be estimated that the reason why the sub genome GFP messenger RNA was not accumulated in each of the protoplasts respectively containing the virus genome RNAs having insertion sequences shown in No. 10 and No. 11 lies in that a viral sub genome RNA promoter region was modified due to insertion or addition of the insertion sequences. This follows that the GFP gene can be expressed also in these virus genome RNAs by further adding a native sub genome RNA promoter sequence.

Further, in a protoplast which contains a virus genome RNA into which the hIFNγ gene was introduced as a foreign gene, proliferation capability of the virus genome RNA was confirmed by northern blotting, and expression of the hIFNγ gene was confirmed by western blotting. In protoplasts which respectively contain the virus genome RNAs having insertion sequences shown in No. 6, No. 7, and No. 12 through No. 14, proliferation of the virus genome RNAs and proliferation of a sub genome hIFNγ messenger RNA was confirmed, and expression of the hIFNγ gene was confirmed since a hIFNγ protein was detected.

Similarly, proliferation of a genome RNA and a sub genome messenger RNA was confirmed in a protoplast containing a mutant of a virus genome into which a cDNA of a virus genome RNA mutated as shown in No. 4 of FIG. 2A was introduced, the virus genome RNA being mutated by using, as a gene encoding a foreign protein, an alpha interferon gene, a CPI-17 protein functional domain gene, a single chain antibody gene, or a calmodulin gene in a similar manner to the above Example.

Example 6

Expression of Protein in Tobacco BY2 Cell

A cDNA of a virus genome RNA into which a GFP gene or a hIFNγ gene was introduced as a foreign gene (see No. 4 of FIG. 2A) was used to transform a tobacco BY2 cell (Dohi et al., Archives of Virology, 151, 1075-1084) in which a transcription factor XVE that was activated by estrogen was expressed with the use of the *agrobacterium* method. Estrogen was added to a culture medium containing the tobacco BY2 cell thus transformed, and three days later, a sample was taken (as for an experimental method, see Dohi et al., Archives of Virology, 151, 1075-1084).

In a transformed tobacco BY2 cell containing the GFP gene, proliferation of a virus genome RNA and a sub genome GFP messenger RNA was confirmed (northern blotting), and expression of the GFP gene was confirmed (fluorescence microscope observation and SDS-PAGE).

Also in a transformed tobacco BY2 cell containing the hIFNγ gene, proliferation of a virus genome RNA and a sub genome hIFNγ messenger RNA was confirmed (northern blotting), and accumulation of a hIFNγ protein was confirmed (western blotting).

Further, proliferation of a virus genome RNA and a sub genome messenger RNA was confirmed, and accumulation of a protein was confirmed in a transformed tobacco BY2 cell into which a cDNA of a virus genome RNA mutated as shown in No. 4 of FIG. 2A was introduced, the virus genome RNA being mutated by using, as a gene encoding a foreign protein, a CPI-17 protein functional domain gene or a single chain antibody gene in a similar manner to the above Example.

Example 7

Figure 4:
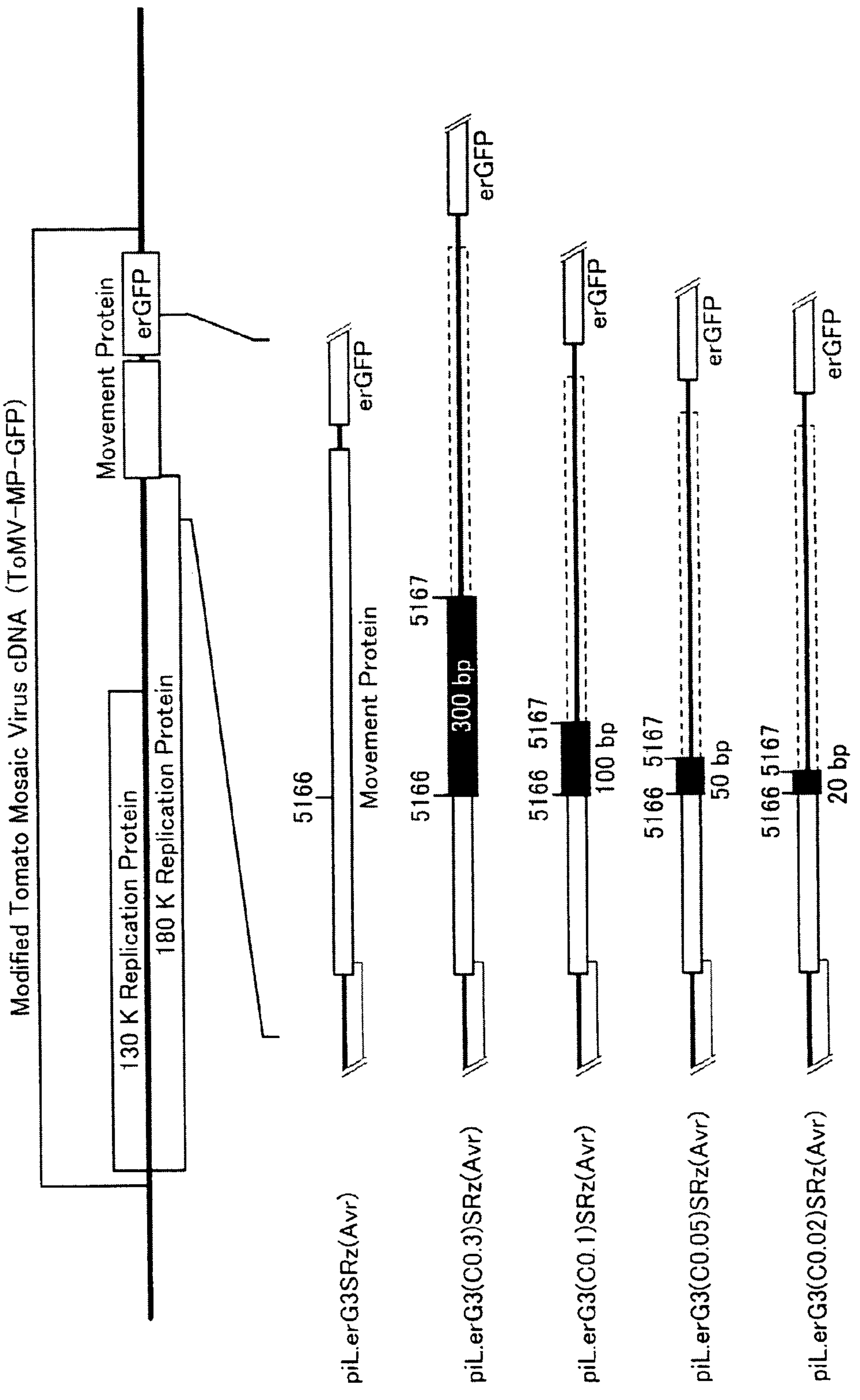
FIG. 4 is a view schematically illustrating structures of plasmid constructs constructed in an Example of the present invention.

Study on Base Length of Insertion Sequence cDNAs of a modified tomato mosaic virus were synthesized by inserting base sequences having base length of 300 base pairs, 100 base pairs, 50 base pairs, and 20 base pairs (SEQ ID NO: 36 through 39) at a position of 5166 bases from the 5' terminal of a base sequence (SEQ ID NO: 20) of a gene encoding a movement protein of a tomato mosaic virus. A cDNA of a modified tomato mosaic virus encoded by a plasmid vector piL.erG3SRz(Avr) was substituted with the cDNAs thus synthesized so that plasmid constructs were constructed (see FIG. 4). In FIG. 4, a plasmid construct into which no insertion sequence was inserted is indicated by piL.erG3SRz(Avr), and plasmid constructs into which insertion sequences of 300 base length, 100 base length, 50 base length, and 20 base length were inserted are indicated by piL.erG3(C0.3)SRz(Avr), piL.erG3(C0.1)SRz(Avr), piL-.erG3(C0.05)SRz(Avr), piL.erG3(C0.02)SRz(Avr), respectively.

The plasmid constructs thus constructed were used to transform *Escherichia coli* JM109 (TOYOBO). The *Escherichia coli* JM109 thus transformed was placed on an LB agar medium containing 100 μg/ml carbenicillin and was incubated at 37° C. for 26 hours. Five colonies whose growth was not affected by other colonies were randomly selected from obtained colonies, and the diameter of each of the five colonies was measured.

The diameter of a colony of *Escherichia coli* having a plasmid containing an insertion sequence was compared with the diameter of a colony of *Escherichia coli* having a plasmid containing no insertion sequence. Table 4 shows obtained relative values and standard errors (n=5). In Table 4, "*" indicates that the t-test revealed that there is a significant difference in colony diameter between a plasmid containing an insertion sequence and piL.erG3SRz(Avr) containing no insertion sequence.

TABLE 4

| Plasmid Name | Number of Inserted Bases (bp) | Colony Diameter (relative value ± S.E.) | Yield of Plasmid (relative value ± S.E.) |
|---|---|---|---|
| piL.erG3SRz(Avr) | — | 1.00 ± 0.05 | 1.00 ± 0.06 |
| piL.erG3(C0.3)SRz(Avr) | 300 | 1.59 ± 0.05* | 3.87 ± 0.36* |
| piL.erG3(C0.1)SRz(Avr) | 100 | 1.17 ± 0.03* | 1.53 ± 0.10* |
| piL.erG3(C0.05)SRz(Avr) | 50 | 1.10 ± 0.02 | 1.27 ± 0.08 |
| piL.erG3(C0.02)SRz(Avr) | 20 | 1.10 ± 0.04 | 1.33 ± 0.15 |

As shown in Table 4, the colony diameter of *Escherichia coli* having piL.erG3(C0.3)SRz(Avr) into which an insertion sequence of 300 base length was inserted or piL.erG3(C0.1)SRz(Avr) into which an insertion sequence of 100 base length was inserted is significantly larger than that of *Escherichia coli* having piL.erG3SRz(Avr) into which no insertion sequence was inserted. That is, an improvement could be observed in growth of *Escherichia coli* having piL.erG3(C0.3)SRz(Avr) and piL.erG3(C0.1)SRz(Avr). Meanwhile, the colony diameter of *Escherichia coli* having piL.erG3(C0.05)SRz(Avr) into which an insertion sequence of 50 base length was inserted or piL.erG3(C0.02)SRz(Avr) into which an insertion sequence of 10 base length was inserted is larger than that of *Escherichia coli* having piL.erG3SRz(Avr) into which no insertion sequence was inserted, but the difference was not significant.

Further, the plasmid constructs were used to transform *Escherichia coli* JM109. One of colonies obtained from the transformed *E. coli* was inoculated into a 3 ml LB culture medium containing antibiotics for selection, and then was incubated at 37° C. for 24 hours with shaking. A plasmid was purified from a 1.5 ml incubation solution by an alkali SDS method. The plasmid thus purified was quantified using a DNA assay kit (Quant-it dsDNA Assay Kit (invitrogen)). A yield of each of the plasmid constructs into which an insertion sequence was inserted was compared to that of a plasmid construct into which no insertion sequence was inserted. Table 4 shows obtained relative values and standard errors (n=3).

As shown in Table 4, a yield of *Escherichia coli* having piL.erG3(C0.3)SRz(Avr) into which an insertion sequence of 300 base length was inserted or piL.erG3(C0.1)SRz(Avr) into which an insertion sequence of 100 base length was inserted was significantly larger than that of *Escherichia coli* having piL.erG3SRz(Avr) into which no insertion sequence was inserted. This means that these plasmids showed good stability. Meanwhile, a yield of *Escherichia coil* having piL.erG3(C0.05)SRz(Avr) into which an insertion sequence of 50 base length was inserted or piL.erG3(C0.02)SRz(Avr) into which an insertion sequence of 10 base length was inserted was larger than that of *Escherichia coli* having piL.erG3SRz(Avr) into which no insertion sequence was inserted, but the difference was not significant.

The use of the present invention allows an improvement in growth of a host cell into which a vector containing a polynucleotide containing a viral base sequence is introduced, thereby improving efficiency of replicating the vector in the cell. As a result, it becomes possible to efficiently produce a useful protein with the use of a vector that is efficiently replicated.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The use of the present invention makes it possible to efficiently produce any protein, and a protein produced with the use of the present invention can be effectively applied to various fields such as plant biotechnology industry, pharmaceutical industry, and food industry.

The invention claimed is:

1. A polynucleotide comprising a tobamoviral nucleotide sequence, the tobamoviral nucleotide sequence comprising:

a first nucleotide sequence encoding a tobamoviral replication protein;

a second nucleotide sequence encoding a tobamoviral movement protein, the second nucleotide sequence being located downstream of the first nucleotide sequence; and a linking site for linking with an exogenous nucleotide sequence encoding a polypeptide to be expressed, wherein the linking site is located downstream of the second nucleotide sequence, and wherein the second nucleotide sequence comprises a mutation relative to the wild-type nucleotide sequence encoding the tobamoviral movement protein, wherein the mutation comprises an insertion of 300 or more contiguous nucleotides, and wherein the insertion is a sequence other than an intron.

2. The polynucleotide according to claim 1, wherein the second nucleotide sequence comprises the mutation at any position from 17 to 795 of the nucleotide sequence shown in SEQ ID NO: 20.

3. The polynucleotide according to claim 1, wherein the first nucleotide sequence encoding a tobamoviral replication protein is:

(i) a polynucleotide encoding a polypeptide having at least 80% identity to SEQ ID NO: 1; or (ii) a polynucleotide encoding a polypeptide having at least 80% identity to SEQ ID NO: 2.

4. The polynucleotide according to claim 1, wherein the second nucleotide sequence is selected from the group consisting of polynucleotides having at least 80% identity to SEQ ID NO: 13 and a polynucleotide which hybridizes with a polynucleotide having a sequence that is complementary to SEQ ID NO: 13 under a stringent condition for hybridization.

5. The polynucleotide according to claim 1, wherein the tobamoviral replication protein and the tobamoviral movement protein are derived from a tobacco mosaic virus or a tomato mosaic virus.

6. A vector comprising the polynucleotide recited in claim 1.

7. A plant comprising the polynucleotide recited in claim 1.

8. A plant comprising the vector recited in claim 6.

9. A transformant comprising the polynucleotide recited in claim 1.

10. A transformant comprising the vector recited in claim 6.

11. A method for producing a polypeptide, comprising:

transforming or transfecting a plant with the polynucleotide recited in claim 1.

12. A method for producing a polypeptide, comprising the step of:

transforming a cell with the polynucleotide recited in claim 1.

13. A kit for producing a polypeptide, comprising the polynucleotide recited in claim 1.

14. A method for producing a polypeptide, comprising the step of:

transforming or transfecting a plant with the vector recited in claim 6.

15. A method for producing a polypeptide, comprising the step of:

transforming a cell with the vector recited in claim 6.

16. A kit for producing a polypeptide, comprising the vector recited in claim 6.

17. A method for producing a polypeptide, comprising the step of:

using the plant recited in claim 7.

18. A method for producing a polypeptide, comprising the step of:

using the transformant recited in claim 9.

19. A kit for producing a polypeptide, comprising the plant recited in claim 7.

20. A kit for producing a polypeptide, comprising the transformant recited in claim 9.

21. A polynucleotide comprising a tobamoviral nucleotide sequence, the tobamoviral nucleotide sequence comprising:

a first nucleotide sequence encoding a tobamoviral replication protein;

a second nucleotide sequence encoding a tobamoviral movement protein, the second nucleotide sequence being located downstream of the first nucleotide sequence; and a linking site for linking with an exogenous nucleotide sequence encoding a polypeptide to be expressed, wherein the linking site is located downstream of the second nucleotide sequence, and wherein the second nucleotide sequence comprises a mutation relative to the wild-type nucleotide sequence encoding the tobamoviral movement protein, wherein the mutation comprises an insertion of 1258 or more contiguous nucleotides.

* * * * *